(12) United States Patent
Briner et al.

(10) Patent No.: US 7,045,545 B1
(45) Date of Patent: May 16, 2006

(54) AMINOALKYLBENZOFURANS AS SEROTONIN (5-HT(2C)) AGONISTS

(75) Inventors: Karin Briner, Indianapolis, IN (US); Joseph Paul Burkhart, Plainfield, IN (US); Timothy Paul Burkholder, Carmel, IN (US); Matthew Joseph Fisher, Mooresville, IN (US); William Harlan Gritton, Zionsville, IN (US); Daniel Timothy Kohlman, Camby, IN (US); Sidney Xi Liang, Fishers, IN (US); Shawn Christopher Miller, Noblesville, IN (US); Jeffrey Thomas Mullaney, Indianapolis, IN (US); Yao-Chang Xu, Fishers, IN (US); Yanping Xu, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/890,311

(22) PCT Filed: Jan. 19, 2000

(86) PCT No.: PCT/US00/01342

§ 371 (c)(1), (2), (4) Date: Dec. 2, 2002

(87) PCT Pub. No.: WO00/44737

PCT Pub. Date: Aug. 3, 2000

Related U.S. Application Data

(60) Provisional application No. 60/117,385, filed on Jan. 27, 1999.

(51) Int. Cl.
*A61K 31/36* (2006.01)

(52) U.S. Cl. .............. 514/465; 514/466; 514/337; 549/467; 546/284.1

(58) Field of Classification Search .......... 514/337, 514/465, 466; 546/284.1; 549/467
See application file for complete search history.

(56) References Cited

FOREIGN PATENT DOCUMENTS

| WO | WO 94 29290 A | 12/1994 |
|---|---|---|
| WO | WO 97 08167 A | 3/1997 |
| WO | WO 97 43272 A | 11/1997 |

OTHER PUBLICATIONS

Schulze-Alexandru, M. et al 'Quasi-atomistic receptor surrogates for the 5-HT2A receptor: a 3D-QSAR study on hallucinogenic substances' CA 132:202636 (2000).*
Ellis, F. et al 'Benzofurans and benzopyrans as chronobiological agents' CA 128:22811 (1997).*
Royer, R. et al 'Benzofurans. L. Access to furoisoquinolines' CA 78:71948 (1973).*
Wolff, M C et al The discriminative stimulus properties of LY233708, a selective seratonin reuptake inhibitor, in the pigeon, Psychopharmacology, (1999) 146:275-279.*
H. Ishii, et al. "Total Synthesis of Lemaireocereine" Chem. Pharm. vol. 40, No. 8, 1992, pgs 1993-1996, XP00887200 p. 1994.
R. Royer, et al. "Recherches Sur le benzofuranne. L.—Étude de voies d'accés aux furoisoquinoléines" Bull. Soc. Chim. Fr., No. 11, 1972,m pp. 4201-4208, XP000088692 table VI.
Schulze-Alexandru, M., et al., n "Quasi-atomistic receptor surrogates for the 5-HT2A receptor: a 3D-QSAR study on hallucinogenic substances" CA 132:202636 (2000).
Ellis, F., et al. "Benzofurans and benzopyrans as chronobiological agents" CA 128:22811 (1997).
Royer, R., et al. "Benzofurans, L. Access to furoisoquinolines" CA 78:71948 (1973).

* cited by examiner

*Primary Examiner*—Amelia A. Owens
(74) *Attorney, Agent, or Firm*—R. Craig Tucker

(57) ABSTRACT

The present invention provides serotonergic aminoalkylbenzofurans of Formula (I): where R, $R^1$, $R^2$, $R^3$, $R^4$, $R^{4'}$, $R^5$, $R^{5'}$, and $R^{12}$ are as described in the specification.

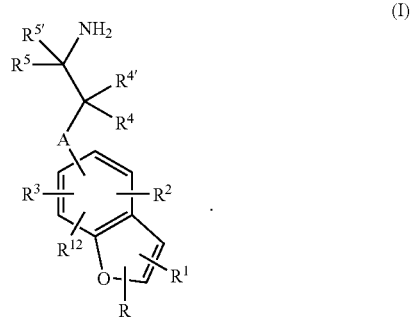

6 Claims, No Drawings

AMINOALKYLBENZOFURANS AS SEROTONIN (5-HT(2C)) AGONISTS

This U.S. national stage application of International Application PCT/US00/01342, filed Jan. 19, 2000, claims priority to U.S. provisional application Ser. No. 60/117,385, filed Jan. 27, 1999.

The neurotransmitter serotonin (5-hydroxytryptamine, 5-HT) has a rich pharmacology arising from a heterogeneous population of at least seven receptor classes. The serotonin 5-HT$_2$ class is further subdivided into at least three subtypes, designated 5-HT$_{2a}$, 5-HT$_{2b}$, and 5-HT$_{2c}$. The 5-HT$_{2C}$ receptor has been isolated and characterized (Julius, et al., U.S. Pat. No. 4,985,352), and transgenic mice lacking the 5-HT$_{2C}$ receptor have been reported to exhibit seizures and an eating disorder resulting in increased consumption of food (Julius, et al., U.S. Pat. No. 5,698,766). Compounds selective for the 5-HT$_{2c}$ receptor would provide useful therapies for the treatment of seizure and eating disorders without the side effects associated with current therapies.

The present invention provides aminoalkylbenzofurans of Formula I:

where:

A is —CHR$^{13}$— or a bond;

R is hydrogen, halo, cyano, —C(O)NR$^6$R$^7$, C$_1$–C$_6$ alkyl, C$_1$–C$_4$ alkoxycarbonyl, carboxy, or phenyl optionally substituted with one or two substituents selected from the group consisting of halo, C$_1$–C$_4$ alkyl, and C$_1$–C$_4$ alkoxy;

R$^1$ is hydrogen, halo, cyano, carboxamido, formyl, trimethylsilyl, trifluoromethyl, pentafluoroethyl, or C$_1$–C$_6$ alkyl;

R$^2$ and R$^3$ are independently hydrogen, halo, amino, nitro, C$_1$–C$_4$ alkoxy, cyano, carboxamido, —C(O)NR$^8$R$^9$, —NR$^{10}$R$^{11}$, —NHC(O)NHR$^{14}$, C$_1$–C$_4$ alkoxycarbonyl, carboxyl, trifluoromethyl, or C$_1$–C$_6$ alkyl optionally substituted with a substituent selected from the group consisting of C$_1$–C$_4$ alkoxy, hydroxy, phenoxy, and phenyl;

R$^4$ and R$^{4'}$ are independently hydrogen, C$_1$–C$_4$ alkyl, or benzyl; or R$^4$ and R$^{4'}$ together with the carbon atom to which they are attached form a cyclopropyl moiety;

R$^5$ is hydrogen, C$_1$–C$_4$ alkyl, or benzyl;

R$^{5'}$ is hydrogen, or R$^5$ and R$^{5'}$ together with the carbon atom to which they are attached form a cyclopropyl moiety;

R$^6$ and R$^7$ are independently hydrogen or C$_1$–C$_4$ alkyl;

R$^8$ is hydrogen or C$_1$–C$_4$ alkyl;

R$^9$ is C$_1$–C$_8$ alkyl where the alkyl chain is optionally substituted with a substituent selected from the group consisting of carboxy, phenyl, or pyridyl, said phenyl or pyridyl substituent optionally substituted with one or two substituents selected from the group consisting of halo, C$_1$–C$_4$ alkyl, or C$_1$–C$_4$ alkoxy;

R$^{10}$ is hydrogen or C$_1$–C$_4$ alkyl;

R$^{11}$ is C$_1$–C$_4$ alkyl or C$_1$–C$_4$ acyl;

R$^{12}$ is hydrogen, halo, or C$_1$–C$_4$ alkyl;

R$^{13}$ is hydrogen, C$_1$–C$_4$ alkyl, or benzyl;

R$^{14}$ is hydrogen, C$_1$–C$_4$ alkyl, or phenyl optionally substituted with a substituent selected from the group consisting of halo, C$_1$–C$_4$ alkyl, and C$_1$–C$_4$ alkoxy;

or pharmaceutically acceptable acid addition salts thereof.

This invention also provides a pharmaceutical formulation which comprises, in association with a pharmaceutically acceptable carrier, diluent or excipient, a compound of Formula I.

The present invention provides a method for increasing activation of the 5-HT$_{2C}$ receptor in mammals by administering to a mammal in need of such activation a pharmaceutically effective amount of a compound of Formula I.

A further embodiment of this invention is a method for increasing activation of the 5-HT$_{2C}$ receptor for treating a variety of disorders which have been linked to decreased neurotransmission of serotonin in mammals. Included among these disorders are depression, obesity, bulimia, premenstrual syndrome or late luteal phase syndrome, alcoholism, tobacco abuse, panic disorder, anxiety, post-traumatic syndrome, memory loss, dementia of aging, social phobia, attention deficit hyperactivity disorder, disruptive behavior disorders, impulse control disorders, borderline personality disorder, obsessive compulsive disorder, chronic fatigue syndrome, premature ejaculation, erectile difficulty, anorexia nervosa, disorders of sleep, autism, anxiety, seizure disorders, and mutism. Any of these methods employ a compound of Formula I.

This invention also provides the use of a compound of Formula I for the manufacture of a medicament for the treatment of obesity. Additionally, this invention provides a pharmaceutical formulation adapted for the treatment of obesity containing a compound of Formula I. Furthermore, this invention includes a method for the treatment of obesity which comprises administering an effective amount of a compound of Formula I.

The general chemical terms used in the formulae above have their usual meanings. For example, the term "alkyl" includes such groups as methyl, ethyl, n-propyl, isopropyl, n-butyl, isobutyl, sec-butyl, tert-butyl, and the like. The term "alkoxy" includes methoxy, ethoxy, propoxy, isopropoxy, butoxy and the like. The term "acyl" includes such groups as formyl, acetyl, propionyl, butyryl, 2-methylpropionyl, and the like. The term "halo" includes fluoro, chloro, bromo and iodo.

Since the compounds of this invention are amines, they are basic in nature and accordingly react with any of a number of inorganic and organic acids to form pharmaceutically acceptable acid addition salts. Since some of the free amines of the compounds of this invention are typically oils at room temperature, it is preferable to convert the free amines to their pharmaceutically acceptable acid addition salts for ease of handling and administration, since the latter are routinely solid at room temperature. Acids commonly employed to form such salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogen-phosphate, dihydrogenphosphate, metaphosphate, pyro-phosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like. Preferred pharmaceutically acceptable salts are those formed with hydrochloric acid.

The skilled artisan will appreciate that certain of the compounds of the present invention have at least one chiral carbon, and may therefore exist as a racemate, as individual enantiomers or diastereomers, and as mixtures of individual enantiomers or diastereomers. For example, individual enantiomers of compounds of the invention where $R^{4'}$ and $R^{5'}$ are hydrogen and one of $R^4$ and $R^5$ are hydrogen, are illustrated by the following structures:

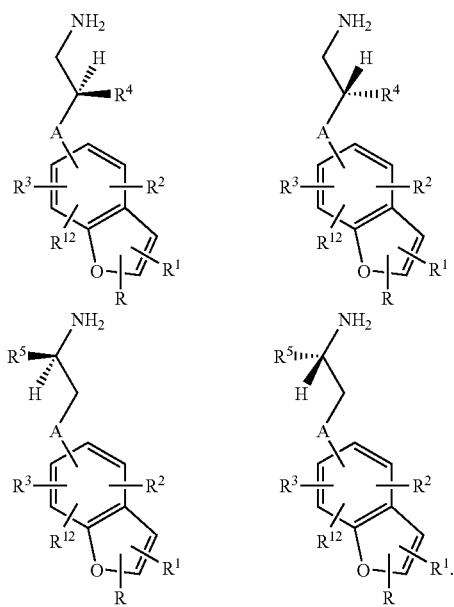

Individual diastereomers, for example those compounds of the present invention where $R^{4'}$ and $R^{5'}$ are hydrogen and both $R^4$ and $R^5$ are other than hydrogen, are illustrated by the following structures:

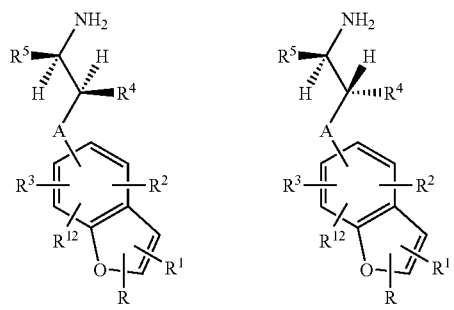

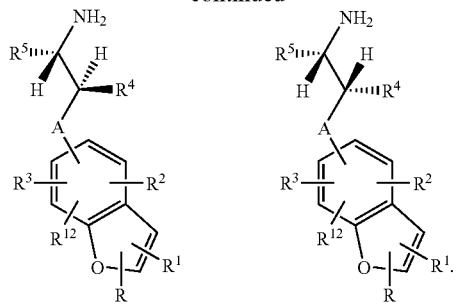

The skilled artisan will appreciate that those compounds of the invention where variable A is —CHR$^{13}$— and R$^{13}$ is other than hydrogen, and those compounds of the invention where $R^{4'}$ and $R^4$ are not the same, introduce additional asymmetric centers into the molecule which create additional optical isomers as described above.

While it is a preferred embodiment of the invention that the compounds of the invention exist, are formulated, and are used as single enantiomers or diastereomers, the present invention also contemplates the compounds of the invention existing in racemic form and as mixtures of the individual enantiomers and diastereomers. The methods and formulations of the invention also contemplate the use and formulation of the compounds of the invention in their racemic form and as mixtures of the individual enantiomers and diastereomers.

The individual enantiomers and diastereomers may be prepared by chiral chromatography of the racemic or enantiomerically or diastereomerically enriched free amine, or fractional crystallization of salts prepared from racemic or enantiomerically or diastereomerically enriched free amine and a chiral acid. Alternatively, the free amine may be reacted with a chiral auxiliary and the enantiomers or diastereomers separated by chromatography followed by removal of the chiral auxiliary to regenerate the free amine. Furthermore, separation of enantiomers or diastereomers may be performed at any convenient point in the synthesis of the compounds of the invention. The compounds of the invention may also be prepared by the use of chiral syntheses.

While all of the aminoalkylbenzofurans of Formula I are useful 5-HT$_{2c}$ agonists, certain classes of the compounds are preferred. The following paragraphs describe such preferred classes.

aa) A is a bond;
ab) A is attached at the 4-position of the benzofuran ring;
ac) A is attached at the 5-position of the benzofuran ring;
ad) A is attached at the 6-position of the benzofuran ring;
ae) A is attached at the 7-position of the benzofuran ring;
af) R is hydrogen;
ag) R is halo;
ah) R is cyano;
ai) R is —C(O)NR$^6$R$^7$;
aj) R is C$_1$–C$_6$ alkyl;
ak) R is C$_1$–C$_4$ alkoxycarbonyl;
al) R is carboxy;
am) R is phenyl optionally substituted with one or two substituents selected from the group consisting of halo, C$_1$–C$_4$ alkyl, and C$_1$–C$_4$ alkoxy;
an) R$^1$ is hydrogen;
ao) R$^1$ is halo;

ap) $R^1$ is cyano;
aq) $R^1$ is carboxamido;
ar) $R^1$ is trifluoromethyl;
as) $R^1$ is $C_1$–$C_4$ alkyl;
at) $R^2$ is hydrogen;
au) $R^2$ is halo;
av) $R^2$ is fluoro;
aw) $R^2$ is amino;
ax) $R^2$ is $C_1$–$C_4$ alkoxy;
ay) $R^2$ is $C_1$–$C_4$ alkyl optionally substituted with a substituent selected from the group consisting of $C_1$–$C_4$ alkoxy, hydroxy, phenoxy, and phenyl;
az) $R^2$ is —C(O)NR$^8$R$^9$;
ba) $R^2$ is —NR$^{10}$R$^{11}$;
bb) $R^2$ is trifluoromethyl;
bc) $R^3$ is hydrogen;
bd) $R^3$ is halo;
be) $R^3$ is fluoro;
bf) $R^3$ is trifluoromethyl;
bg) $R^3$ is $C_1$–$C_4$ alkyl optionally substituted with a substituent selected from the group consisting of $C_1$–$C_4$ alkoxy, hydroxy, phenoxy, phenyl;
bh) $R^3$ is —NR$^{10}$R$^{11}$;
bi) $R^4$ is hydrogen;
bj) $R^4$ is $C_1$–$C_4$ alkyl;
bk) $R^4$ is methyl;
bl) $R^{4'}$ is hydrogen;
bm) $R^{4'}$ is $C_1$–$C_4$ alkyl;
bn) $R^{4'}$ is methyl;
bo) $R^4$ and $R^{4'}$ taken together with the carbon to which they are attached form a cyclopropyl moiety;
bp) $R^5$ is hydrogen;
bq) $R^5$ is $C_1$–$C_4$ alkyl;
br) $R^5$ is methyl;
bs) $R^{5'}$ is hydrogen;
bt) $R^6$ is hydrogen;
bu) $R^6$ is $C_1$–$C_4$ alkyl;
by) $R^6$ is methyl;
bw) $R^7$ is hydrogen;
bx) $R^7$ is $C_1$–$C_4$ alkyl;
by) $R^7$ is methyl;
bz) $R^8$ is hydrogen;
ca) $R^8$ is $C_1$–$C_4$ alkyl;
cb) $R^8$ is methyl;
cc) $R^{10}$ is hydrogen;
cd) $R^{10}$ is $C_1$–$C_4$ alkyl;
ce) $R^{10}$ is methyl;
cf) $R^{11}$ is $C_1$–$C_4$ alkyl;
cg) $R^{11}$ is methyl;
ch) $R^{11}$ is $C_1$–$C_4$ acyl;
ci) $R^{12}$ is hydrogen;
cj) $R^{12}$ is $C_1$–$C_4$ alkyl;
ck) $R^{12}$ is methyl;
cl) $R^{12}$ is halo;
cm) $R^{12}$ is chloro;
cn) $R^{12}$ is fluoro;
co) The compound is a free base;
cp) The compound is a salt;
cq) The compound is the hydrochloride salt;
cr) The compound is a racemate;
cs) The compound is a single enantiomer;
ct) The compound has one chiral center and is in the (R) configuration;
cu) The compound has one chiral center and is in the (S) configuration;
cv) The compound is a single diastereomer;
cw) The compound has two chiral centers which are both in the (R) configuration;
cx) The compound has two chiral centers one of which is in the (R) configuration and the other is in the (S) configuration;
cy) The compound has two chiral centers which are both in the (S) configuration;
cz) A is attached at the 7-position of the benzofuryl moiety and only one of $R^2$, $R^3$, or $R^{12}$ are other than hydrogen;
da) A is attached at the 7-position of the benzofuryl moiety and only two of $R^2$, $R^3$, and $R^{12}$ are other than hydrogen;
db) A is attached at the 7-position of the benzofuryl moiety and all three of $R^2$, $R^3$, and $R^{12}$ are other than hydrogen.

It will be understood that the above classes may be combined to form additional preferred classes.

The present invention also provides a method for increasing activation of the 5-HT$_{2C}$ receptor in mammals by administering to a mammal in need of such activation a pharmaceutically effective amount of a compound of Formula I. The preferred mammal is human.

The following group is illustrative of aminoalkylbenzofurans contemplated within the scope of the invention:

1-(2-pentafluoroethyl-5-fluorobenzofur-7-yl)-2-aminopropane;

1-(2-(3-fluorophenyl)-5-chlorobenzofur-7-yl)-2-aminopropane;

1-(3-(4-isopropylphenyl)benzofur-5-yl)-2-aminopropane methanesulfonate;

(R)-1-(3-(2-methoxyphenyl)-7-trifluoromethylbenzofur-6-yl)-2-aminopropane;

1-(4-(1-phenyleth-2-yl)benzofur-7-yl)-2-aminopropane 2-naphthalenesulfonate;

1-(5-(4-phenoxypent-1-yl)benzofur-4-yl)-2-aminopropane benzoate;

3-(5-fluorobenzofur-7-yl)-1-aminobutane hydrochloride;

3-(4-trifluoromethylbenzofur-6-yl)-1-aminobutane hydrobromide;

3-(7-methylbenzofur-4-yl)-1-aminobutane maleate;

(S)-1-(5-([N'-methyl-N'-(1-(2-chlorophenyl)eth-2-yl)]-carboxamido)benzofur-7-yl)-2-aminopropane;

1-(5-([N'-(5-(2,4-dimethoxyphenyl)pent-1-yl)]-carboxamido)benzofur-7-yl)-2-aminopropane;

1-(5-([N'-(5-(3-chloro-4-methylphenyl)hex-2-yl)]-carboxamido)benzofur-7-yl)-2-aminopropane fumarate;

1-(5-([N'-isopropyl-N'-(4-(3-bromopyridin-2-yl)but-1-yl)]carboxamido)benzofur-7-yl)-2-aminopropane propionate;

1-(4-([N'-(3-(4-methoxypyridin-3-yl)hept-2-yl)]-carboxamido)benzofur-7-yl)-2-aminopropane succinate;

1-(5-([N'-(3-(2-chloro-6-methoxypyridin-4-yl)prop-1-yl)]carboxamido)benzofur-7-yl)-2-aminopropane 4-chlorobenzoate;

1-(2-aminoethyl)-1-(5-fluorobenzofur-7-yl)cyclopropane;

1-amino-1-(5-chloro-6-trifluoromethylbenzofur-4-yl)-cyclopropane benzoate.

The compounds of the invention where variable A is a bond are prepared beginning with an appropriately substituted benzofuran as illustrated in the following scheme where variables R, $R^1$, $R^2$, $R^3$, $R^4$, $R^{4'}$, and $R^5$ are as previously defined:

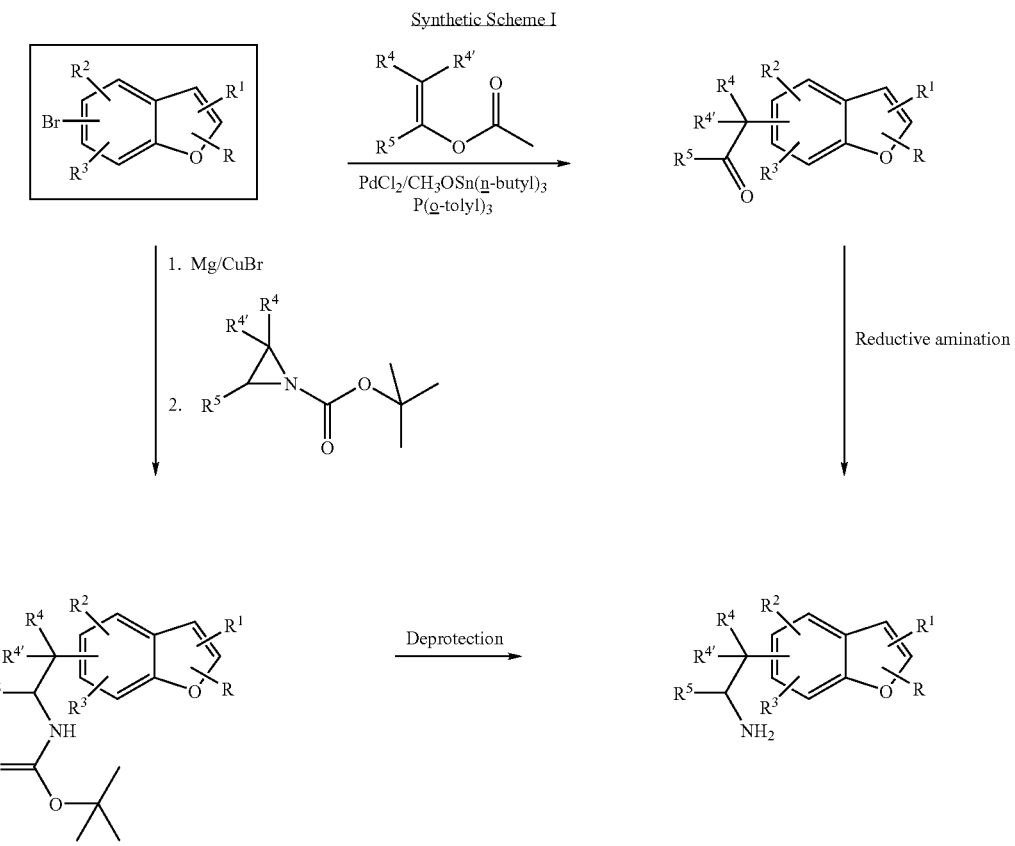

Synthetic Scheme I

The bromobenzofuran is coupled with an appropriate enol acetate in the presence of palladium(II) chloride, tri(o-tolyl) phosphine, and tributyl tin methoxide to provide the corresponding ketone. This ketone is then reductively aminated under standard conditions, such as treatment of the ketone with ammonium acetate and sodium cyanoborohydride in the presence of acid, to provide the primary amines of the present invention.

Alternatively, the bromobenzofuran may be treated with magnesium to prepare the corresponding Grignard reagent. This compound is then reacted with copper(I) bromide followed by an appropriate N-protected aziridine to provide the corresponding N-protected amine. Deprotection of the amine then provides the compounds of the present invention. The skilled artisan will appreciate that the nature of the substituents on the benzofuran ring dictate those protecting groups which may be conveniently removed. Commonly the protecting group employed is the tert-butoxycarbonyl group, which is then removed by treatment with acid, typically hydrochloric acid.

Compounds of the invention where variable A is —CHR$^{13}$— are prepared as described in the following scheme where variables R, R$^1$, R$^2$, R$^3$, R$^4$, R$^5$, R$^{12}$, and R$^{13}$ are as previously defined:

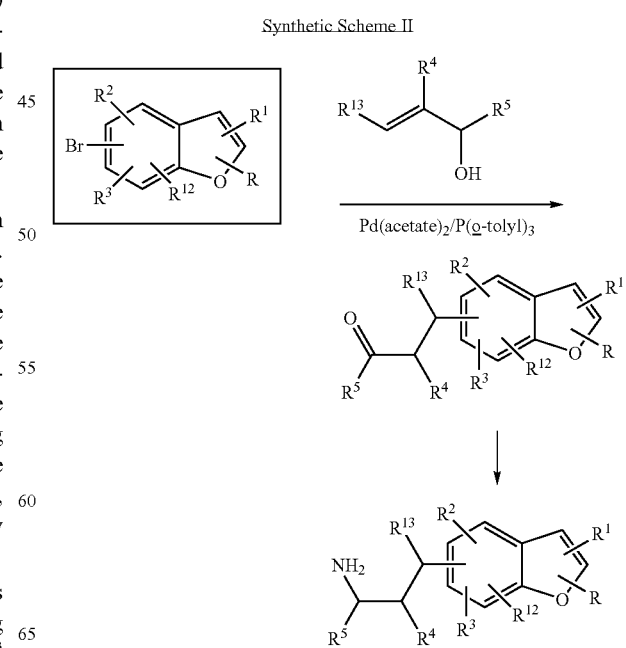

Synthetic Scheme II

The bromobenzofuran is coupled with an appropriate allylic alcohol in the presence of palladium(II) acetate and an appropriate triarylphosphine such as triphenylphosphine or tri(o-tolyl)phosphine to provide the corresponding ketone. This ketone is then reductively aminated under standard conditions to provide the compounds of the present invention. The skilled artisan will appreciate that the R$^{4t}$ moiety may be introduced by reacting the ketone prepared above with an appropriate alkylating agent under standard conditions.

The requisite benzofuran intermediates are either commercially available or may be prepared from an appropriately substituted phenol by methods well known in the art as illustrated in the following scheme where variables R$^2$, R$^3$, and R$^{12}$ are as previously defined:

such as chlorobenzene. Suitable acids include concentrated sulfuric acid, polyphosphoric acid, and acidic resins such as Amberlyst 15™.

Alternatively, the phenoxide solution is treated with an allyl bromide or allyl chloride to provide, after standard isolation and purification procedures, the corresponding allyl ether. This purified ether is heated at a temperature sufficient to effect an ortho-Claisen rearrangement to provide the corresponding o-allylphenol. It is critical that the allyl ether employed in this rearrangement is substantially free of residual dimethylformamide. The skilled artisan will appreciate that, depending upon the location and nature of the R$^2$ and R$^3$ substituents, the rearrangement can provide a mixture of two isomeric products. These isomers may be separated at this stage or later in the synthetic sequence as

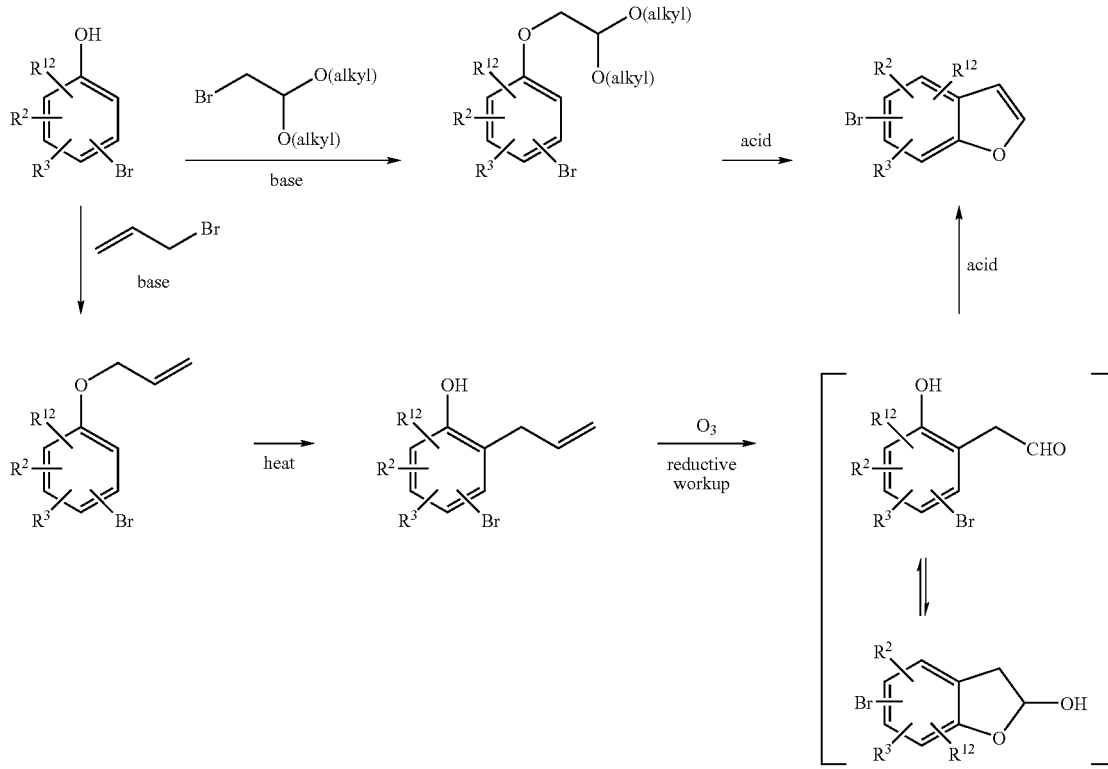

Synthetic Scheme III

A solution of an appropriately substituted phenol in a suitable solvent, typically dimethylformamide, is treated with a base, to generate the corresponding phenoxide. Bases useful for this reaction include hydride sources, such as sodium or potassium hydride, or carbonates, such as sodium or potassium carbonate. The phenoxide solution is then reacted with a chloro- or bromoacetaldehyde which is protected as a cyclic or dialkyl acetal. Bromoacetaldehyde diethyl acetal is particularly useful for this reaction. The phenoxyacetaldehyde acetal prepared by this procedure is reacted with a source of acid in a suitable solvent to provide the desired benzofuran. Suitable solvents include aromatic solvents such as toluene, xylene, benzene, and halobenzenes is convenient or desired. The separation may be effected by chromatography, distilla-tion, or crystallization. The o-allylphenol is then treated with an excess of ozone in an appropriate solvent, dichloromethane and methanol are useful solvents for this step. The reaction mixture is then purged of ozone and the ozonide is treated under reducing conditions, typically by treatment with triphenylphosphine or dimethylsulfide, to provide the corresponding phenylacetaldehyde. The skilled artisan will appreciate that the orientation of the aldehyde with the respect to the phenolic hydroxyl group gives rise to the formation of a cyclic hemiacetal which exists in some equilibrium mixture with the free hydroxyaldehyde. A solution of this equilibrium mixture in a suitable solvent, such as toluene, is treated with a catalytic amount of an appropriate acid, such as sulfuric acid, to provide the desired benzofuran.

The skilled artisan will appreciate that benzofurans substituted in the 2- and/or 3-position may be prepared by modification of the chemistry described in Synthetic Scheme III. For example, the phenol may be alkylated with a suitable haloketone and then cyclized to provide a substituted benzofuran. Alternatively, the benzofuran moiety may be substituted in the 2- or 3-position at any convenient point in the synthesis of the compounds of the present invention by methods known to those skilled in the art.

The requisite benzofurans may also be prepared from an appropriately substituted phenol as illustrated in the following scheme where variables $R^2$, $R^3$, and $R^{12}$ are as previously defined:

Synthetic Scheme IV

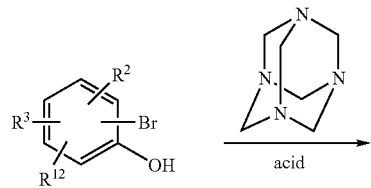

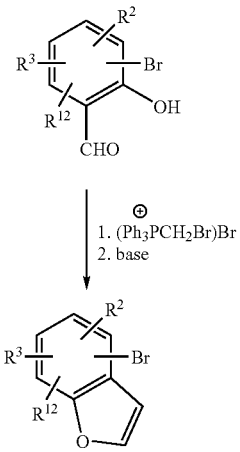

A mixture of an appropriate phenol and hexamethylenetetramine are treated with an appropriate acid, such as trifluoroacetic acid, to provide upon aqueous workup the corresponding o-formylphenol. This o-formylphenol is then treated with (bromomethyl)triphenylphosphonium bromide followed by an appropriate base such as potassium tert-butoxide to provide the desired benzofuran.

Compounds of the invention where $R^4$, $R^{4'}$ and $R^5$ are other than hydrogen may also be prepared as described in Synthetic Scheme V where variables $R^2$, $R^3$, and $R^{12}$ are as previously defined:

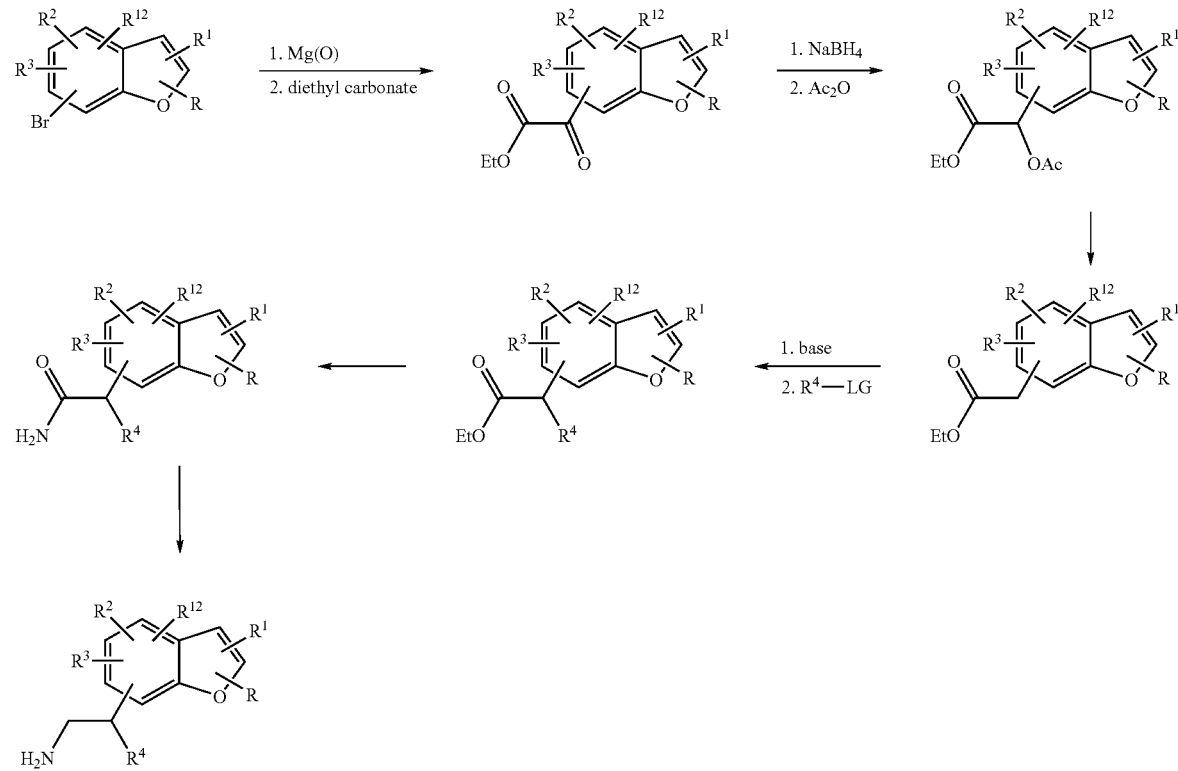

An appropriate bromobenzofuran is treated with elemental magnesium to prepare the corresponding Grignard reagent. The Grignard reagent is quenched with diethyl carbonate and the resulting adduct is treated sequentially with sodium borohydride and acetic anhydride. The α-acetoxyester is then treated with samarium iodide to provide the ethyl α-benzofurylacetate. The anion is generated and then quenched with an appropriate alkylating agent ($R^4$-LG). The resulting α-alkylester is converted to the α-alkylamine by standard methods for such functional group transformations. The skilled artisan will appreciate that a second substituent could be added to the molecule by generating the anion of the α-alkylester and quenching with the same or a different alkylating agent prior to converting the ester to the corresponding amine.

Compounds of the invention where $R^4$ and $R^{4'}$ taken together with the carbon atom to which they are attached form a cyclopropyl moiety may be prepared as illustrated in Synthetic Scheme VI, where R. $R^1$, $R^2$. $R^3$, and $R^{12}$ are as previously described.

An appropriately substituted bromobenzofuran is treated with either magnesium metal to provide the corresponding Grignard reagent, or with an alkyllithium at low temperature to effect halogen metal exchange. Either of these reagents is then reacted with an appropriate reagent, for example dimethylformamide, to provide the corresponding formylbenzofuran. This formylbenzofuran is reduced under standard hydride reducing conditions, for example sodium borohydride in ethanol, to provide the corresponding alcohol. The alcohol is then converted to the corresponding nitrile by either converting first to the corresponding halide and displacing with a source of cyanide anion, or by directly converting the alcohol to the nitrile by reaction with trimethylsilylchloride and sodium cyanide in a mixture of dimethylformamide and acetonitrile in the presence of catalytic sodium iodide as described by Dans et al. (*Journal of Organic Chemistry*, 46, 2985 (1981)).

The requisite nitrile may also be prepared beginning with an appropriate benzofurylacetate ester, such as ethyl benzofurylacetate. The benzofurylacetate ester is reacted with formamide in the presence of an appropriate base, such as Synthetic Scheme VI

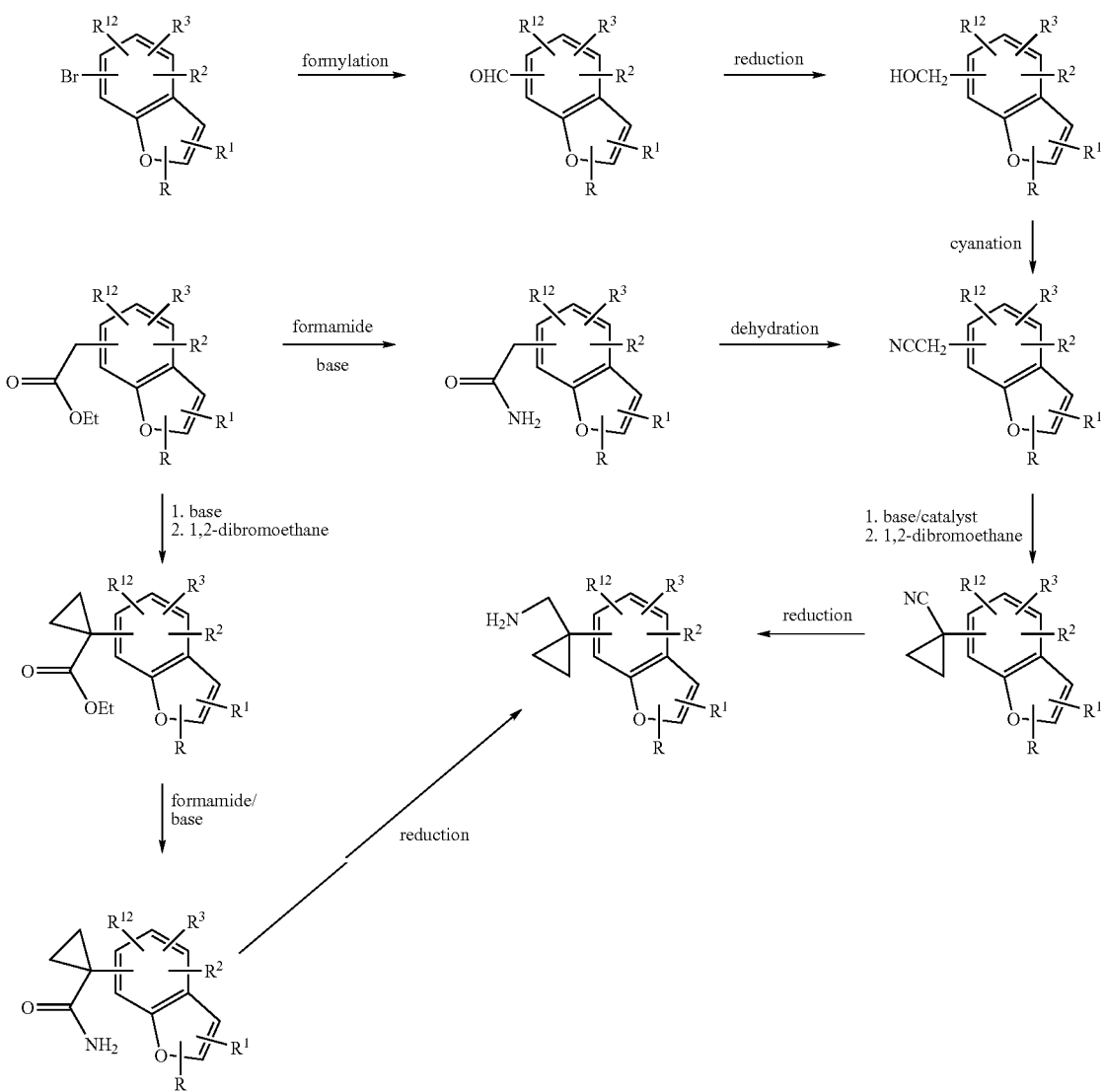

sodium methoxide, to prepare the corresponding benzofurylacetamide. This acetamide is then dehydrated to provide the desired nitrile by reaction with an appropriate dehydrating agent, such as trifluoroacetic anhydride in the presence of pyridine as described by Campagna, et al. (*Tetrahedron Letters*, 1813 (1977)).

The cyclopropyl moiety is introduced by reacting this nitrile with 1,2-dibromoethane and aqueous sodium hydroxide in the presence of a phase-transfer catalyst such as benzyltriethylammonium chloride under the conditions described by Sychkova and Shabarov (*Zh. Org. Khim.*, 16, 2086 (1980)). Reduction of the corresponding cyclopropylamide with an appropriate hydride reducing agent, for example lithium aluminum hydride or borane dimethylsulfide complex, provides the compound of the present invention.

Alternatively, the benzofurylacetate ester may be reacted with 1,2-dibromoethane in the presence of an excess of an appropriate base, such as lithium diisopropylamide, to provide the corresponding ester of 1-benzofuryl-1-carboxycyclopropane. The ester moiety is then converted to the requisite aminomethyl moiety by the functional group transformations previously described.

Compounds of the invention where $R^5$ and $R^{5'}$ taken together with the carbon atom to which they are attached form a cyclopropyl moiety may be prepared as illustrated in Synthetic Scheme VII, where R. $R^1$, $R^2$. $R^3$, and $R^{12}$ are as previously described and BOC is tert-butoxycarbonyl.

Synthetic Scheme VII

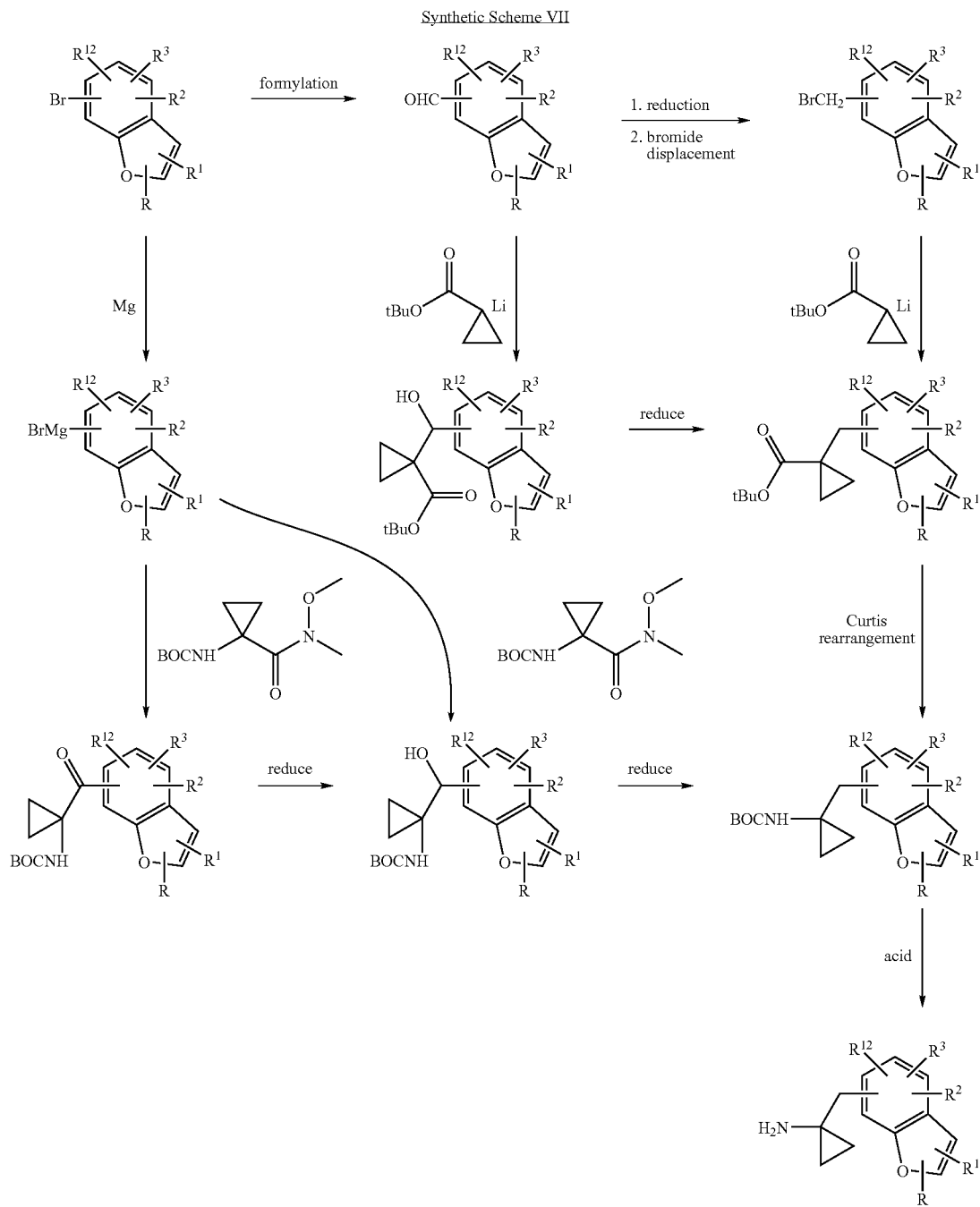

An appropriately substituted bromobenzofuran is converted to the corresponding aldehyde as described supra. This aldehyde is then reacted with 1-tert-butoxycarbonyl-cyclopropyllithium essentially as described by Haener et al. (*Helvetica Chimica Acta,* 69, 1655–65 (1986)) to provide the corresponding 1-tert-butoxycarbonyl-1-(benzofuryl)hydroxymethylcyclopropane. The alcohol is reduced to methylene by treating the corresponding acetate with samarium (II) iodide as described supra. The resulting tertbutyl ester is subjected to standard Curtius rearrangement conditions to provide the corresponding N-tert-butoxycarbonyl 1-amino-1-(benzofuryl)methylcyclopropane. This compound is deprotected by treatment with acid to provide the compounds of the present invention. If necessary or desired, the starting aldehyde may be reduced to the corresponding alcohol and then converted to the corresponding bromomethylbenzofuran. This reagent is then reacted with 1-tert-butoxycarbonylcyclopropyllithium essentially as described by Haener, to provide 1-tert-butoxycarbonyl-1-(benzofuryl) methylcyclopropane which is then subjected to the Curtius rearrangement/deprotection sequence described supra to provide the compounds of the present invention.

Alternatively, the starting bromobenzofuran may be reacted with magnesium metal under standard conditions to prepare the corresponding Grignard reagent, benzofuryl-magnesium bromide. This Grignard reagent is then reacted with the Weinreb amide, N-methyl N-methoxy 1-(tert-butoxycarbonylamino)cyclopropane-1-carboxamide, to provide 1-(tert-butoxycarbonylamino)-1-(benzofurylcarbonyl) cyclopropane. This ketone is then reduced under standard conditions, typically with sodium borohydride in methanol or ethanol, to provide 1-(tert-butoxycarbonylamino)-1-(benzofuryl(hydroxymethyl))cyclopropane. This alcohol is then converted to the corresponding acetate and reduced to the corresponding methylene by treatment with samarium iodide as previously described. The resulting 1-(tert-butoxycarbon-yl)-1-(benzofurylmethyl)cyclopropane is treated with acid under standard conditions to provide the compounds of the present invention. If necessary or desired, the Weinreb amide may be reduced by reaction with lithium aluminum hydride to provide the corresponding aldehyde essentially as described by Fehrentz and Castro (*Synthesis,* 676 (1983)). This aldehyde is then reacted with the Grignard reagent previously described to prepare 1-(tert-butoxycarbonylamino)-1-(benzofuryl(hydroxymethyl))cyclopropane, which is then subjected to the reaction conditions previously described to prepare the compounds of the present invention. The requisite Weinreb amide, N-methyl N-methoxy 1-(tert-butoxycarbonylamino)cyclopropane-1-carboxamide, may be prepared from the commercially available 1-amino-1-carboxycyclopropane by standard methods well known in the art.

The skilled artisan will appreciate that not all substituents are compatible with the reaction conditions employed to prepare the compounds of the invention. Those substituents incompatible with these conditions may be introduced at a more convenient point in the synthesis, or may be prepared by functional group transformations well known to one of ordinary skill in the art. Furthermore, many of the compounds of the present invention, while useful 5-HT$_{2C}$ agonists in their own right, are useful intermediates to prepare other compounds of the invention. Those compounds of the invention bearing an ester functionality, for example, may be hydrolyzed under standard conditions to provide the corresponding carboxylic acids. These acids may then be reacted with amines under standard peptide coupling conditions to provide the corresponding amides. Alternatively, the esters may be reduced to provide the corresponding alcohols. Furthermore, alkoxy groups may be cleaved to provide the corresponding phenols, and primary amines may be diazotized and displaced to provide the corresponding halogenated compounds.

The following Preparations and Examples are illustrative of methods useful for the synthesis of the compounds of the present invention.

Preparation I 5-fluoro-7-bromobenzofuran 2-(2-bromo-4-fluorophenoxy)acetaldehyde diethyl acetal To a solution of 20 gm (105 mMol) 2-bromo-4-fluorophenol in 211 mL dimethylformamide were added 15.8 mL (105 mMol) bromoacetaldehyde diethyl acetal followed by 14.5 gm (105 mMol) anhydrous potassium carbonate. This mixture was then heated at reflux for about 18 hours under a nitrogen atmosphere. The reaction mixture was then concentrated under reduced pressure and the resulting residue partitioned between 200 mL of ethyl acetate and 200 mL 1N sodium hydroxide. The phases were separated and the ethyl acetate phase was washed with 200 mL of water, giving rise to an emulsion. An additional 100 mL ethyl acetate and 20 mL of water were added to the emulsion. The separated ethyl acetate phase and emulsion were removed and saved. The ethyl acetate phase was washed again with 200 mL of water. This new emulsion was combined with the original emulsion and aqueous phase. The mixture was partitioned between 700 mL ethyl acetate and 780 mL of water. The emulsion and aqueous layer (1600 mL) were removed. The organic phase was dried over magnesium sulfate and concentrated under reduced pressure to provide 26.4 gm (82%) of the desired material as an amber oil. The reserved emulsion and aqueous phase was washed with 1 L of toluene. The phases were separated and organic phase was dried over magnesium sulfate and concentrated under reduced pressure to provide an additional 4.67 gm of the desired compound as an amber oil. Total recovery of desired product was 31.1 gm (96.7%).

Cyclization

A mixture of 109.4 gm Amberlyst-15 in 707 mL chlorobenzene was heated at reflux to remove water by azeotropic distillation. Distillate was removed until the volume remaining in the pot was about 500 mL. To this mixture was then added dropwise over 2 hours a solution of 109.4 gm (356 mMol) 2-(2-bromo-4-fluorophenoxy)acetaldehyde diethyl acetal in 4060 mL chlorobenzene. The mixture was stirred at reflux with constant water removal. When no more water was observed in the azeotrope distillate, the reaction mixture was cooled to room temperature. The filter cake was washed with 400 mL dichloromethane and the combined filtrates were concentrated under reduced pressure to provide 102 gm of a colorless oil. This oil was diluted with 500 mL hexane and subjected to silica gel chromatography, eluting with hexane. Fractions containing the desired product were combined and concentrated under reduced pressure to provide 39.6 gm (52%) of the title compound.

$^1$H-NMR(CDCl$_3$): δ 7.75 (d, J=2.1 Hz, 1H), 7.27 (dd, JH,H=2.5 Hz, JH,F=8.8 Hz, 1H), 7.25 (dd, JH,H=2.5 Hz, JH,F=8.3 Hz, 1H), 6.85 (d, J=2.2 Hz, 1H).

Preparation II 4-methoxy-7-bromobenzofuran 2-bromo-5-methoxyphenol and
4-bromo-5-methoxyphenol A solution of 40.0 gm (322.2 mMol) 3-methoxyphenol in 1 L acetonitrile was cooled to 0° C. under a nitrogen atmosphere. To this cooled solution was added a solution of 57.35 gm (322.2 mMol) N-bromosuccinimide in 500 mL acetonitrile dropwise at a rate to maintain the temperature of the reaction mixture at 0° C. (approximately 2 hours). The reaction mixture was stirred at 0° C. for about 1 hour after the addition was complete and was then concentrated under reduced pressure. The residue was treated with carbon tetrachloride and the solid which formed was removed by filtration. The filtrate was concentrated under reduced pressure to provide a mixture of bromination isomers as a red oil.

This oil was subjected to silica gel chromatography, eluting with a gradient system of hexane containing from 0–30% ethyl acetate. Fractions containing the fastest eluting compound were combined and concentrated under reduced pressure to provide 18.1 gm (28%) of 2-bromo-5-methoxyphenol as a clear liquid.

$^1$H-NMR(CDCl$_3$): δ 7.31 (d, 1H), 6.6 (d, 1H), 6.41 (dd, 1H), 5.5 (s, 1H), 3.77 (s, 3H).

Fractions containing the later eluting components were combined and concentrated under reduced pressure. This residue was subjected to silica gel chromatography, eluting with dichloromethane. Fractions containing substantially pure 4-bromo-5-methoxyphenol were combined and concentrated under reduced pressure to provide 24.1 gm (37%) of a white crystalline solid (m.p.=68–69° C.).

$^1$H-NMR(CDCl$_3$): δ 7.34 (d, 1H), 6.45 (d, 1H), 6.33 (dd, 1H), 4.9 (br s, 1H), 3.85 (s, 3H).

2-(2-bromo-5-methoxyphenoxy)acetaldehyde
diethyl acetal

A mixture of 16.0 gm (78.8 mMol) 2-bromo-5-methoxyphenol, 10.9 gm (78.8 mMol) potassium carbonate, and 15.5 gm (78.8 mMol) bromoacetaldehyde diethyl acetal in 300 mL dimethylformamide was heated at 142° C. for 16 hours. The reaction mixture was then cooled to room temperature and diluted with 100 mL 2N sodium hydroxide followed by 500 mL ethyl acetate. This mixture was washed twice with 1 L of water. The combined aqueous washes were extracted twice with 300 mL portions of ethyl acetate. All organic phases were combined, washed with 1 L of water, washed with 1 L of saturated aqueous sodium chloride, dried over magnesium sulfate and concentrated under reduced pressure to provide the desired compound as a dark amber oil.

Cyclization

A mixture of 17 gm polyphosphoric acid in 500 mL chlorobenzene was heated to 80° C. with stirring. To this mixture was added dropwise over 30 minutes a solution of 16 gm (50.13 mMol) 2-(2-bromo-5-methoxyphenoxy)acetaldehyde diethyl acetal in 100 mL chlorobenzene. The resulting mixture was stirred for 5 hours at 80° C. and 2 hours at 120° C. The reaction mixture was cooled to room temperature and the chlorobenzene solution was decanted from the polyphosphoric acid phase. The remaining residue was washed with five 200 mL portions of diethyl ether. All of the organic phases were combined and concentrated under reduced pressure to provide a dark amber oil. This oil was subjected to silica gel chromatography, eluting with a gradient of hexane containing from 0–5% ethyl acetate. Fractions containing product were combined and concentrated under reduced pressure to provide 11.3 gm (99%) of the title compound as a white, crystalline solid (m.p.=60–62° C.).

EA: Calculated for C$_9$H$_7$BrO$_2$: Theory: C, 47.61; H, 3.11. Found: C, 47.40; H, 3.37.

Preparation III 5-bromo-6-methoxybenzofuran

Beginning with 23 gm (113.3 mMol) 4-bromo-5-methoxyphenol, 16.2 gm of the title compound were prepared as a white crystalline solid essentially by the procedure of Preparation II.

Preparation IV 4-bromobenzofuran and 6-bromobenzofuran 2-(3-bromophenoxy)acetaldehyde diethyl acetal A solution of 10 gm (57.8 mMol) 3-bromophenol in 25 mL dimethylformamide was added dropwise to a mixture of 2.8 gm (70 mMol) sodium hydride (60% suspension in mineral oil) in 30 mL dimethylformamide. The reaction mixture was stirred for one hour after the addition was complete. To the reaction mixture was then added 9.7 mL (64.5 mMol) bromoacetaldehyde diethyl acetal and the resulting mixture was stirred at 153° C. for 2 hours. The reaction mixture was then allowed to cool to room temperature and was diluted with 300 mL diethyl ether. This mixture was then washed with two 150 ml portions of water, washed with 50 mL saturated aqueous sodium chloride, dried over magesium sulfate and concentrated under reduced pressure to provide about 17 gm of the desired compound.

$^1$H-NMR(CDCl$_3$): δ 7.15–7.05 (m, 2H), 6.85 (dd, 1H), 4.8 (t, 1H), 3.95 (d, 2H), 3.8–3.55 (m, 4H), 1.25 (t, 6H).

Cyclization

A mixture of 17 gm (57.8 mMol) 2-(3-bromophenoxy)acetaldehyde diethyl acetal and 17.5 gm polyphosphoric acid in 400 mL chlorobenzene was heated to 80° C. for 2 hours. The reaction mixture was cooled to room temperature and the chlorobenzene was decanted from the polyphosphoric acid. The polyphosphoric acid was washed with two 150 mL portions of diethyl ether. All or the organic phases were combined and concentrated under reduced pressure. The residue was redissolved in diethyl ether and the organic phases were washed with saturated aqueous sodium bicarbonate, water, and saturated aqueous sodium chloride, dried over magnesium sulfate and concentrated under reduced pressure. The residual oil was subjected to silica gel chromatography, eluting with hexane.

Fractions containing the faster eluting isomer were combined and concentrated under reduced pressure to provide 1.7 gm (15%) 4-bromobenzofuran.

EA: Calculated for C$_8$H$_5$BrO: Theory: C, 48.77; H, 2.56. Found: C, 48.89; H, 2.72.

Fractions containing the slower eluting isomer were combined and concentrated under reduced pressure to provide 2.5 gm (22%) 6-bromobenzofuran.

EA: Calculated for C$_8$H$_5$BrO: Theory: C, 48.77; H, 2.56. Found: C, 48.89; H, 2.67.

Preparation V

5-bromobenzofuran

Beginning with 10 gm (57.8 mMol) 4-bromophenol, 4.2 gm (38%) of the title compound were prepared essentially by the procedure described in Preparation IV.

EA: Calculated for $C_8H_5BrO$: Theory: C, 48.77; H, 2.56. Found: C, 48.51; H, 2.46.

Preparation VI

7-bromobenzofuran

Beginning with 10 gm (57.8 mMol) 2-bromophenol, 5 gm (45%) of the title compound were prepared essentially by the procedure described in Preparation IV.

EA: Calculated for $C_8H_5BrO$: Theory: C, 48.77; H, 2.56. Found: C, 49.02; H, 2.82.

Preparation VII

5-methoxy-7-bromobenzofuran

2-bromo-4-methoxyphenol

A solution of 2.6 mL (100 mMol) bromine in 10 mL carbon disulfide was added dropwise over 30 minutes to a solution of 12.4 gm (100 mMol) 4-methoxyphenol in 20 mL carbon disulfide at 0° C. After 30 minutes an additional 1 mL of bromine in 10 mL carbon disulfide are added dropwise. The reaction mixture was then concentrated under reduced pressure and the residue was dissolved in diethyl ether. This solution was washed sequentially with 100 mL water and 100 mL saturated aqueous sodium chloride, dried over magnesium sulfate and concentrated under reduced pressure. The residue was subjected to silica gel chromatography, eluting with a gradient of hexane containing from 0 to 20% ethyl acetate. Fractions containing product were combined and concentrated under reduced pressure to provide 11.6 gm (57%) of the desired compound as a crystalline solid.

$^1$H-NMR(CDCl$_3$): δ 7.0 (d, 1H), 6.95 (d, 1H), 6.8 (dd, 1H), 5.15 (s, 1H), 3.75 (s, 3H).

Beginning with 11.5 gm (56.9 mMol) 2-bromo-4-methoxyphenol, 4.5 gm (35%) of the title compound were prepared essentially by the procedure described in Preparation IV.

EA: Calculated for $C_9H_7BrO_2$: Theory: C, 47.61; H, 3.11. Found: C, 47.79; H, 3.13.

Preparation VIII

6-methoxy-7-bromobenzofuran

2-bromo-3-methoxyphenol

A solution of 22 gm (177.4 mMol) 3-methoxyphenol in 30 mL dihydropyran was added dropwise to a solution of 100 mg (0.525 mMol) p-toluenesulfonic acid monohydrate in 10 mL dihydropyran while cooling in an ice/water bath. After stirring for 1 hour the reaction mixture was diluted with 300 mL diethyl ether and then washed sequentially with 100 mL 0.1 N sodium hydroxide and 100 mL saturated aqueous sodium chloride. The remaining organic phase was dried over magnesium sulfate and concentrated under reduced pressure. The resulting oil was distilled. The fraction distilling at 110–130° C. was collected and then partitioned between 5 N sodium hydroxide and diethyl ether. The organic phase was separated, washed sequentially with water and saturated aqueous sodium chloride, dried over magnesium sulfate and concentrated under reduced pressure to provide 27.1 gm (73%) of tetrahydropyran-2-yl 3-methoxyphenyl ether.

$^1$H-NMR(CDCl$_3$): δ 7.18 (t, 1H), 6.65–6.60 (m, 2H), 6.50 (dd, 1H), 5.4 (t, 1H), 3.95–3.90 (m, 1H), 3.80 (s, 3H), 3.62–3.55 (m, 1H), 2.0–1.6 (m, 6H).

33 mL (52.8 mMol) n-butyllithium (1.6 M in hexane) were added dropwise to a solution 10 gm (48.1 mMol) tetrahydropyran-2-yl 3-methoxyphenyl ether in 100 mL tetrahydrofuran over 15 minutes. After stirring for 2.5 hours at room temperature, the reaction mixture was cooled to 0° C. and then 4.6 mL (53.2 mMol) 1,2-dibromoethane were added dropwise. The reaction mixture was then allowed to stir at room temperature for about 14 hours. The reaction mixture was then diluted with 50 mL 1 N hydrochloric acid and was stirred for 1 hour. The aqueous phase was extracted with three 100 mL portions of diethyl ether. The organic phases were combined and extracted well with 5 N sodium hydroxide. These basic aqueous extracts were combined and cooled in an ice/water bath. The pH of this aqueous solution was adjusted to about 1 with 5 N hydrochloric acid and then extracted with three 100 mL portions of diethyl ether. These ether extracts were combined and washed with saturated aqueous sodium chloride, dried over magnesium sulfate and concentrated under reduced pressure. The resulting residue was subjected to silica gel chromatography, eluting with a gradient of hexane containing from 0 to 10% ethyl acetate. Fractions containing the desired compound were combined and concentrated under reduced pressure to provide 2.91 gm (30%) of a residue which crystallized upon standing.

EA: Calculated for $C_7H_7BrO_2$: Theory: C, 41.41; H, 3.48. Found: C, 41.81; H, 3.46.

Beginning with 6.9 gm (34 mMol) 2-bromo-3-methoxyphenol, 3.2 gm (41%) of the title compound were prepared as a white fluffy solid essentially by the procedure described in Preparation IV.

High Resolution MS: Calculated for $C_9H_7BrO_2$: Theory: 225.9629. Found: 225.9626.

Preparation IX

4-fluoro-7-bromobenzofuran

Beginning with 5 gm (26 mMol) 2-bromo-5-fluorophenol and 6.5 gm (39 mMol) bromoacetaldehyde ethylene glycol acetal, 3.3 gm (59%) of the title compound were prepared essentially by the procedure described in Preparation IV.

EA: Calculated for $C_8H_4BrFO$: Theory: C, 44.69; H, 1.88. Found: C, 44.44; H, 1.91.

Preparation X

5-bromo-7-fluorobenzofuran

Beginning with 20.5 gm (108 mMol) 2-fluoro-4-bromophenol, 3.0 gm (13%) of the title compound were prepared essentially by the procedure described in Preparation I.

$^1$H-NMR(CDCl$_3$): δ 7.65 (d, J=2.4 Hz, 1H), 7.50 (d, J=1.5 Hz, 1H), 7.19 (dd, $J_H$=1.5 Hz, $J_F$=8.3 Hz, 1H), 6.76 (m, 1H).

Preparation XI

6-fluoro-7-bromobenzofuran

Beginning with 7.5 gm (39.3 mMol) 2-bromo-3-fluorophenol, 10.83 gm (90%) 2-(2-bromo-3-fluorophenoxy)-acetaldehyde diethyl acetal was prepared essentially as described in Preparation IV.

Beginning with 5.0 gm (16.3 mMol) of 2-(2-bromo-3-fluorophenoxy)acetaldehyde diethyl acetal, 2.2 gm (63%) of the title compound were prepared essentially as described in Preparation IV.

Preparation XII

5-chloro-7-bromobenzofuran

Beginning with 25 gm (120.5 mMol) 2-bromo-4-chlorophenol, 41.16 gm crude 2-(2-bromo-4-chlorophenoxy)-acetaldehyde diethyl acetal was prepared essentially as described in Preparation IV. A sample of this crude material was subjected to silica gel chromatography to provide an analytical sample.

EA: Calculated for $C_{12}H_{16}BrClO_3$: Theory: C, 44.54; H, 4.98. Found: C, 44.75; H, 4.97.

Beginning with 20 gm (61.8 mMol) of 2-(2-bromo-4-chlorophenoxy)acetaldehyde diethyl acetal, 4.48 gm (31%) of the title compound were prepared as a crystalline solid essentially as described in Preparation I.

EA: Calculated for $C_8H_4BrClO$: Theory: C, 41.51; H, 1.74. Found: C, 41.67; H, 1.78.

Preparation XIII

4,5-difluoro-7-bromobenzofuran

Beginning with 5 gm (23.9 mMol) 2-bromo-4,5-difluorophenol, 7.05 gm (91%) 2-(2-bromo-4,5-difluorophenoxy)-acetaldehyde diethyl acetal were prepared essentially as described in Preparation IV.

EA: Calculated for $C_{12}H_{15}BrF_2O_3$: Theory: C, 44.33; H, 4.65. Found: C, 44.34; H, 4.41.

Beginning with 6.60 gm (20.3 mMol) of 2-(2-bromo-4,5-difluorophenoxy)acetaldehyde diethyl acetal, 0.42 gm (9%) of the title compound were prepared as a crystalline solid essentially as described in Preparation I.

EA: Calculated for $C_8H_3BrF_2O$: Theory: C, 41.24; H, 1.30. Found: C, 41.20; H, 1.51.

Preparation XIV

3-methyl-5-fluoro-7-bromobenzofuran 1-(2-bromo-4-fluorophenoxy)-2-propanone

A mixture of 1.9 gm (10 mMol) 2-bromo-4-fluorophenol, 0.92 gm (10 mMol) chloroacetone, 0.1 gm potassium iodide, and 1.4 gm (10 mMol) potassium carbonate in 100 mL tetrahydrofuran was heated at reflux for 4 hours. The mixture was concentrated under reduced pressure and the residue partitioned between dichloromethane and 1 N sodium hydroxide. The phases were separated and the aqueous phase extracted well with dichloromethane. The organic phases were combined, washed with 1 N sodium hydroxide, dried over sodium sulfate and concentrated under reduced pressure. The residual was subjected to silica gel chromatography, eluting with hexane containing 20% ethyl acetate. Fractions containing product were combined and concentrated under reduced pressure to provide 2.7 gm (100%) of the desired compound as a white solid.

Cyclization

Beginning with 2.7 gm (10 mMol) 1-(2-bromo-4-fluorophenoxy)-2-propanone and 15 gm polyphosphoric acid, 2.03 gm (81%) of the title compound were prepared as a yellow crystalline solid essentially as described in Preparation II.

Preparation XV

2-methyl-5-fluoro-7-bromobenzofuran

Ethyl 2-(2-bromo-4-fluorophenoxy)propionate

A mixture of 15 gm (78.5 mMol) 2-bromo-4-fluorophenol, 11.2 mL (86.4 mMol) ethyl 2-bromopropionate, and 13 gm (94.2 mMol) potassium carbonate was heated at reflux for 3 hours. At this point 0.1 gm potassium iodide were added and reflux continued for another 2 hours. The reaction mixture was partitioned between water and ethyl acetate. The phases were separated and the aqueous phase was extracted well with ethyl acetate. The organic phases were combined, washed with saturated aqueous sodium chloride, dried over sodium sulfate, and concentrated under reduced pressure. The residue was subjected to silica gel chromatography, eluting with hexane containing 5% ethyl acetate. Fractions containing product were combined and concentrated under reduced pressure to provide 19.8 gm (87%) of the desired compound as a clear oil.

2-(2-bromo-4-fluorophenoxy)propionaldehyde

A solution of 19.4 gm (66.7 mMol) ethyl 2-(2-bromo-4-fluorophenoxy)propionate in 400 mL toluene was cooled to −78° C. at which point 100 mL (100 mMol) diisobutylaluminum hydride (1 M in toluene) were added dropwise over 35 minutes. The reaction mixture was stirred at −78° C. for an additional 20 minutes after the addition was complete and then the reaction was quenched by the addition of methanol. The reaction mixture was warmed to room temperature and then treated with saturated aqueous sodium potassium carbonate. The mixture was stirred for 30 minutes and was then extracted well with ethyl acetate. The organic phases were combined, dried over sodium sulfate, and concentrated under reduced pressure to provide 16.9 gm of crude desired compound.

Cyclization

Beginning with 16.5 gm of the crude aldehyde, 5.2 gm (34% for the reduction and cyclization) of the title compound were prepared essentially as described in Preparation II.

Preparation XVI

5-nitro-7-bromobenzofuran

Potassium 5-nitro-7-bromobenzofuran-2-carboxylate

A mixture of 11.0 gm (44.7 mMol) 2-hydroxy-3-bromo-5-nitrobenzaldehyde, 5.56 gm (40.24 mMol) potassium carbonate, and 8.0 mL (46.95 mMol) diethyl bromomalonate in 55 mL 2-butanone was heated at reflux for 5 hours. The reaction mixture was cooled to room temperature and concentrated under reduced pressure. The residue was partitioned between 450 mL diethyl ether and 250 mL water and the aqueous phase was adjusted to pH of about 1 by the addition of dilute sulfuric acid. The phases were separated and the aqueous phase was extracted with two 150 mL portions of diethyl ether. The organic phases were combined, washed with 50 mL saturated aqueous sodium chloride, dried over magnesium sulfate and concentrated under reduced pressure. The residual solid was dissolved in 200 mL ethanol to which were added 4.8 gm (85.5 mMoL) potassium hydroxide. The resulting suspension was warmed on a steam bath for 1 hour. The suspension was then cooled to room temperature. After about 18 hours the mixture was filtered and dried under reduced pressure to provide 14.1 gm (98%) of the desired compound as an orange solid.

$^{13}$C-NMR(DMSO-d$_6$): δ 160.3, 159.8, 154.0, 143.9, 129.7, 122.2, 117.7, 108.0, 103.8.

5-nitro-7-bromobenzofuran-2-carboxylic acid

A mixture of 11.5 gm (35.5 mMol) potassium 5-nitro-7-bromobenzofuran-2-carboxylate and 36 gm Dowex 50WX8-200 resin in 1.6 L methanol was stirred for 1 hour at room temperature. The mixture was filtered and the filtrate concentrated under reduced pressure. The residue was diluted with about 80 mL of methanol and heated on the steam bath with stirring. The mixture was cooled to room temperature and filtered. The residual solid was dried under vacuum to provide 6.7 gm (66%) of the desired compound as a gold solid.

m.p.=257° C. (dec.)

MS(FD): m/e=285, 287 (M$^+$)

EA: Calculated for C$_9$H$_4$NO$_5$Br: Theory: C, 37.79; H, 1.41; N, 4.90. Found: C, 37.81; H, 1.55; N, 4.77.

Decarboxylation

A sonicated mixture of 0.42 gm (1.47 mMol) 5-nitro-7-bromobenzofuran-2-carboxylic acid and 0.085 gm copper powder in 10 mL freshly distilled quinoline was heated at 185° C. under nitrogen for 7 minutes. The reaction mixture was cooled to room temperature and filtered. The solid recovered was washed with two 20 mL portions of dichloromethane and these washes were combined with the filtrate. The filtrate was then diluted with 70 mL dichloromethane and was washed sequentially with two 100 mL portions of 1 N hydrochloric acid, and 50 mL 4:1 saturated aqueous sodium chloride:5 N sodium hydroxide. The remaining organics were dried over sodium sulfate and concentrated under reduced pressure. The residue was subjected to silica gel chromatography, eluting with hexane containing 10% ethyl acetate. Fractions containing product were combined and concentrated under reduced pressure. The residual solid was crystallized from hexane to provide 0.15 gm (42%) of the title compound as fine, light orange needles.

m.p.=90–92° C.

MS(FD): m/e=241, 243 (M$^+$)

EA: Calculated for C$_8$H$_4$NO$_3$Br: Theory: C, 39.70; H, 1.67; N, 5.79. Found: C, 40.05; H, 2.03; N, 5.67.

Preparation XVII

N-tert-butoxycarbonyl-2-methylaziridine

A mixture containing 11 mL (0.142 mMol) 2-methylaziridine in 300 mL dichloromethane and 300 mL saturated aqueous sodium bicarbonate was cooled to 0° C. To the mixture were added 30.9 gm (0.142 mMol) di-tert-butyldicarbonate and stirring was continued for 18 hours as the temperature was allowed to gradually increase to room temperature. The phases were separated and the organic phase was washed with 200 mL of water, dried over magnesium sulfate, and concentrated under reduced pressure to provide 22.6 gm of the title compound.

$^1$H-NMR(CDCl$_3$): δ 2.45–2.35 (m, 1H), 2.20 (d, J=5.9 Hz, 1H), 1.84 (d, J=3.7 Hz, 1H), 1.42 (s, 9H), 1.23 (d, J=5.9 Hz, 3H).

Preparation XVIII (R)-N-tert-butoxycarbonyl-2-methylaziridine (R)-N-tert-butoxycarbonyl-2-amino-1-propanol A solution of 10 gm (133 mMol) (R)-2-amino-1-propanol and 14.8 gm (146.5 mMol) triethylamine in 500 mL tetrahydrofuran was cooled to 0° C. To this solution was added all at once 30 gm (133 mMol) di-tert-butyl dicarbonate. The reaction mixture was allowed to stir for about 18 hours at room temperature. The reaction mixture was then concentrated under reduced pressure and the resulting residue was dissolved in 300 mL ethyl acetate. This solution was washed twice with 200 mL of water, once with 200 mL of saturated aqueous sodium chloride, dried over magnesium sulfate and concentrated under reduced pressure to provide 22 gm (94%) of the desired compound as a yellow oil.

$^1$H-NMR(CDCl$_3$): δ 4.71 (m, 1H), 3.72 (m, 1H), 3.59–3.46 (m, 2H), 2.86 (m, 1H).

(R)-N-tert-butoxycarbonyl-O-methanesulfonyl-2-amino-1-propanol

A solution of 22.0 gm (125.6 mMol) (R)-N-tert-butoxycarbonyl-2-amino-1-propanol and 19.5 gm (150.7 mmol) diisopropylethylamine in 450 mL dichloromethane was cooled to 0° C. To this solution was added dropwise 10.7 mL (138.2 mMol) methanesulfonyl chloride at a rate to maintain the temperature of the reaction mixture at from 0° C. to 10° C. Once the addition was complete the reaction mixture was stirred at 0° C. for about one hour. The reaction mixture was washed twice with 200 mL portions of water, once with 200 mL saturated aqueous sodium chloride, dried over magnesium sulfate and concentrated under reduced pressure. The residue was subjected to silica gel chromatography, eluting with 1:1 hexane:ethyl acetate. Fractions containing product were combined and concentrated under reduced pressure. The residue was crystallized from hexane and ethyl acetate to provide 19.4 gm (61%) of the desired compound in two crops (m.p.=65–68° C.)

$^1$H-NMR(CDCl$_3$): δ 4.59 (m, 1H), 4.20 (m, 1H), 4.14, 4.12 (dd, 1H), 3.95 (m, 1H), 3.01 (s, 3H), 1.42 (s, 9H), 1.21 (d, 3H), 1.41 (s, 9H), 1.08 (d, 2H).

Cyclization

A solution of 5 gm (19.7 mMol)(R)-N-tert-butoxycarbonyl-O-methanesulfonyl-2-amino-1-propanol in 100 mL tetrahydrofuran was cooled to −78° C. under a nitrogen atmosphere. To this solution was added dropwise 19.94 mL (19.94 mMol) lithium bis(trimethylsilyl)amide (1.0 N in tetrahydrofuran). The reaction mixture was to warm gradually to room temperature over about 18 hours. The reaction mixture was diluted with diethyl ether and the resulting solution was washed with water, washed with saturated aqueous sodium chloride, dried over magesium sulfate, and concentrated under reduced pressure to provide the title compound as a yellow oil.

OR: $[\alpha]_D^{20}$=−22.86° (c=1.03, CHCl$_3$)

Preparation XIX (S)-N-tert-butoxycarbonyl-2-methylaziridine

Beginning with (S)-2-amino-1-propanol, the title compound was prepared essentially as described in Preparation XVIII.

OR: $[\alpha]_D^{20}$=+34.95° (c=1.03, $CH_2Cl_2$)

Preparation XX 3-trifluoromethyl-5-fluoro-7-bromobenzofuran

A solution of 2.10 gm (16.7 mMol) 1-trifluoromethyl-prop-1-en-3-ol, 3.19 gm (16.7 mMol) 2-bromo-4-fluorophenol, and 4.81 gm (18.4 mMol) triphenylphosphine in 25 mL dichloromethane was cooled to 0° C. and then 2.9 mL (18.4 mMol) diethyl azodicarboxylate were added. The reaction mixture was stirred for 1 hour at room temperature and then the reaction mixture was directly subjected to flash silica gel chromatography, eluting with 20:1 hexane:ethyl acetate. Fractions containing product were combined and concentrated under reduced pressure to provide 6 gm of crude 1-(1-trifluoromethylprop-1-en-3-yloxy)-2-bromo-4-fluorobenzene.

1.0 gm (3.34 mmol) 1-(1-trifluoromethylprop-1-en-3-yloxy)-2-bromo-4-fluorobenzene was heated at 250° C. for 3 hours. The reaction mixture, containing primarily 2-(3-trifluoromethylprop-1-en-3-yl)-4-fluoro-6-bromophenol, was diluted with dichloromethane and the solution cooled to −78° C. This solution was then treated with excess ozone and was stirred at −78° C. until the 2-(3-trifluoromethyl-prop-1-en-3-yl)-4-fluoro-6-bromophenol was consumed as measured by thin layer chromatography. At this point the ozone was purged from the reaction with oxygen and then 0.88 gm (3.34 mMol) triphenylphosphine were added. The mixture was stored at −20° C. for about 64 hours. The reaction mixture was then concentrated under reduced pressure and the residue subjected to flash silica gel chromatography, eluting with hexane containing 10% ethyl acetate. Fractions containing the desired compound were combined and concentrated under reduced pressure to provide 2-hydroxy-3-trifluoromethyl-5-fluoro-7-bromo-2,3-dihydrobenzofuran. A solution of this dihydrobenzofuran in 10 mL toluene was treated with 4 drops of sulfuric acid and was stirred at reflux for 10 minutes. The reaction mixture was cooled to room temperature and was then washed with saturated aqueous sodium bicarbonate. The organic phase was separated and concentrated under reduced pressure. The residue was subjected to flash silica gel chromatography, eluting with hexane. Fractions containing product were combined and concentrated under reduced pressure to provide the title compound.

Preparation XXI 5-methoxycarbonyl-7-bromobenzofuran

Beginning with methyl 3-bromo-4-allyloxybenzoate, the title compound was prepared essentially as described in Preparation XX.

Preparation XXII

N-tert-butoxycarbonyl 1-(5-carboxybenzofur-7-yl)-2-aminopropane

A mixture of 0.341 gm (1.02 mMol) N-tert-butoxycarbonyl 1-(5-methoxycarbonylbenzofur-7-yl)-2-aminopropane (EXAMPLE 41) and 0.204 gm (5.1 mMol) sodium hydroxide in 2 mL ethanol and 0.5 mL water was stirred at room temperature for 18 hours. The reaction mixture was concentrated under reduced pressure and the residue dissolved in water. This aqueous solution was washed with ethyl acetate and the organic phase discarded. The remaining aqueous phase was made acidic by the addition of aqueous potassium hydrogen sulfate. The aqueous phase was again extracted with ethyl acetate. This organic phase was dried over magnesium sulfate and concentrated under reduced pressure. The residue was crystallized from a mixture of chloroform and hexane to provide 0.300 gm (92%) of the title compound as a white crystalline solid in two crops.

EA: Calculated for $C_{17}H_{21}NO_5$: Theory: C, 63.94; H, 6.63; N, 4.39. Found: C, 63.78; H, 6.75; N, 4.34.

Preparation XXIII 3-ethyl-5-fluoro-7-bromobenzofuran

Beginning with pent-2-en-1-yl 2-bromo-4-fluorophenyl ether, the title compound was prepared essentially as described in Preparation XX.

Preparation XXIV 3-isopropyl-5-fluoro-7-bromobenzofuran

Beginning with 4-methylpent-2-en-1-yl 2-bromo-4-fluorophenyl ether, the title compound was prepared essentially as described in Preparation XX.

Preparation XXV 3,4-dimethyl-5-fluoro-7-bromobenzofuran

Beginning with but-2-en-1-yl 2-bromo-4-fluoro-5-methylphenyl ether, the title compound was prepared essentially as described in Preparation XX.

Preparation XXVI 4-chloro-5-fluoro-7-bromobenzofuran

Bromination

A mixture of 5 gm (34.1 mMol) 3-chloro-4-fluorophenol and 1.76 mL (34.1 mMol) bromine in 20 mL carbon disulfide was stirred at room temperature for 18 hours. The reaction mixture was concentrated under reduced pressure and the residue was dissolved in dichloromethane, washed with water, dried over sodium sulfate and concentrated under reduced pressure to provide a mixture of 2-bromo-4-fluoro-5-chlorophenol and 2-bromo-3-chloro-4-fluorophenol.

Ether Formation

This mixture of bromination isomers was combined with 12 gm allyl bromide and 13.6 gm potassium carbonate in 90 mL dimethylformamide. After stirring at room temperature for 2.5 hours, the mixture was partitioned between dichloromethane and water. The organic phases were combined, dried over sodium sulfate and concentrated under reduced pressure to provide 9.7 gm of a mixture of allyl ether isomers.

Rearrangement/Ozonolysis/Dehydration

The mixture of allyl ethers was reacted as described in Preparation XX to provide 0.49 gm of the title compound as a white crystalline solid.

m.p.=84–85° C.

¹H-NMR(300 MHz, CDCl₃): δ 7.73 (d, J=2.1 Hz, 1H, 7.29 (d, J=8.8 Hz, 1H); 6.92 (d, J=2.1 Hz, 1H).

Preparation XXVII 4-trifluoromethyl-7-bromobenzofuran

Beginning with 4-trifluoromethylphenol, the title compound was prepared essentially as described in Preparation XXVI.

Preparation XXVIII 5-trifluoromethyl-7-bromobenzofuran

Beginning with 5-trifluoromethylphenol, the title compound was prepared essentially as described in Preparation XXVI.

Preparation XXIX 4,5,6-trifluoro-7-bromobenzofuran

Beginning with 3,4,5-trifluorophenol, the title compound was prepared essentially as described in Preparation XXVI.

Preparation XXX 4,6-dimethyl-5-chloro-7-bromobenzofuran

Beginning with 3,5-dimethyl-4-chlorophenol, the title compound was prepared essentially as described in Preparation XXVI.

Preparation XXXI

Alternate Synthesis of
4,5-difluoro-7-bromobenzofuran 2-bromo-4,5-difluorophenyl allyl ether A mixture of 79.4 gm (0.38 mole) 2-bromo-4,5-difluorophenol and 79 gm (0.57 mole) potassium carbonate in 200 mL dimethylformamide was stirred at room temperature for 30 minutes. At this point 33 mL (0.38 mMol) allyl bromide were added and the resulting mixture was stirred for 18 hours at room temperature. The reaction mixture was then diluted with diethyl ether and washed with water followed by saturated aqueous sodium chloride. The remaining organics were dried over magnesium sulfate and concentrated under reduced pressure to provide 90 gm (96%) of the desired compound.

2-allyl-3,4-difluoro-6-bromophenol 15 gm (60.5 mMol) 2-bromo-4,5-difluorophenyl allyl ether was heated at 200° C. for 2 hours under a nitrogen atmosphere. The reaction mixture was cooled to room temperature and filtered through a pad of celite. The celite pad was washed with 500 mL hexane and the filtrate concentrated under reduced pressure. The residue was subjected to flash silica gel chromatography, eluting with hexane. Fractions containing product were combined and concentrated under reduced pressure to provide 9.7 gm (65%) of the desired compound.

(2-hydroxy-3-bromo-5,6-difluorophenyl)acetaldehyde

A solution of 7.8 gm (31.45 mMol) 2-allyl-3,4-difluoro-6-bromophenol in 100 mL dichloromethane and 20 mL methanol was cooled to −78° C. and was then saturated with ozone. After 20 minutes the reaction mixture was purged with nitrogen for 10 minutes and was then treated with 5 mL dimethylsulfide. The reaction mixture was allowed to warm gradually to room temperature. After 15 hours the reaction mixture was concentrated under reduced pressure to provide the title compound.

Cyclization

A mixture of 7.5 gm Amberlyst 15™ resin in 150 mL chlorobenzene was heated at 160° C. and the solvent distilled to remove water. The reaction mixture was cooled to 120° C. and then a solution of 31.45 mMol (2-hydroxy-3-bromo-5,6-difluorophenyl)acetaldehyde in chlorobenzene was added dropwise. The temperature was again increased to 160° C. and solvent distilled. After 1.5 hours, the reaction mixture was filtered and the filtrate concentrated under reduced pressure. The residue was subjected to silica gel chromatography, eluting with hexane. Fractions containing product were combined and concentrated under reduced pressure to provide 3.9 gm (53%) of the title compound as a white solid.

m.p.=46.5–48° C.

Preparation XXXII 5-hydroxymethyl-7-bromobenzofuran

A solution of 0.63 gm (2.46 mmol) 5-methoxycarbonyl-7-bromobenzofuran in 10 mL toluene was cooled to −78° C. When material precipitated, 5 mL dichloromethane were added to effect solution. To this solution were then slowly added 1.5 mL (8.6 mmol) diisobutylaluminum hydride and the reaction mixture was allowed to warm gradually to room temperature. After 10 minutes the reaction was quenched by the addition of methanol followed by 1.5 gm sodium fluoride and 50 mL water and then Rochelle's salt solution. The mixture was diluted with additional dichloromethane and was stirred vigorously for about 1 hour. The phases were separated and the aqueous phase extracted well with ethyl acetate. The organic phases were combined and concentrated under reduced pressure. The residue was crystallized from hexane and dichloromethane to provide 0.46 gm (82%) of the title compound as a white crystalline solid.

Preparation XXXIII 5-methoxymethyl-7-bromobenzofuran

A solution of 0.372 gm (0.40 mMol) 5-hydroxymethyl-7-bromobenzofuran in tetrahydrofuran was added to a mixture of 1.80 mMol sodium hydride (60% suspension in mineral oil) in 2 mL tetrahydrofuran. After stirring at room temperature for 1 hour, 204 µL iodomethane were added and stirring was continued for 2.5 hours. The reaction mixture was quenched by the addition of water and the resulting mixture was extracted well with ethyl acetate. The organic phase was concentrated under reduced pressure to provide a nearly quantitative yield of the title compound.

Preparation XXXIV

5-[N,N-dimethyl]carboxamido-7-bromobenzofuran

A solution of 0.52 gm (2.03 mMol) 5-methoxycarbonyl-7-bromobenzofuran and 0.41 gm (10.13 mMol) sodium hydroxide in 4 mL ethanol was stirred at room temperature until all of the starting material had been consumed. The reaction mixture was concentrated under reduced pressure and the residue dissolved in water. This solution was then made basic by the addition of 1N sodium hydroxide and was extracted well with ethyl acetate. The remaining aqueous phase was made acidic (pH about 2) by treatment with potassium hydrogen sulfate and the resulting solid removed by filtration. The aqueous phase was extracted well with ethyl acetate and the organics were combined and concentrated under reduced pressure to provide 0.40 gm (82%) of 5-carboxy-7-bromobenzofuran as an off-white solid.

MS(FD): m/e=240 (M−1)

A mixture of 0.22 gm (0.92 mMol) 5-carboxy-7-bromobenzofuran, 0.19 gm (1.01 mMol) 1-(3-dimethylaminopropyl)-3-ethylcarbodiimide hydrochloride, 0.074 gm (0.92 mMol) dimethylamine hydrochloride, and 0.38 µL (2.75 mMol) triethylamine in 1 mL dichloromethane was stirred at room temperature for 18 hours. The reaction mixture was diluted with ethyl acetate and quenched with dilute aqueous sodium hydroxide. The phases were separated and the aqueous phase extracted well with ethyl acetate. The organic phases were combined, washed sequentially with water and saturated aqueous sodium chloride, dried over sodium sulfate and concentrated under reduced pressure. The residue was subjected to silica gel chromatography, eluting with hexane containing 20% ethyl acetate. Fractions containing product were combined and concentrated under reduced pressure to provide the title compound.

Preparation XXXV

4-bromo-5-fluoro-, and 5-fluoro-6-bromobenzofuran

O-acetyl 3-bromo-4-fluorophenol

A solution of 1.09 gm (5 mMol) 3-bromo-4-fluoroacetophenone and 3.45 gm (20 mMol) m-chloroperbenzoic acid (70%) in 15 mL dichloromethane was heated at reflux for 18 hours. An additional 3.45 gm m-chloroperbenzoic acid were added and reflux continued for about 12 hours. At this point an additional 1.4 gm m-chloroperbenzoic acid were added and reflux continued for 18 hours. The reaction mixture was cooled to room temperature and was then diluted with 50 mL diethyl ether. The resulting mixture was cooled to 0° C. and was then treated with 15 mL 20% aqueous sodium thiosulfate. The resulting slurry was stirred for about 1 hour and then the phases separated. The organic phase was washed sequentially with 3×20 mL 20% aqueous sodium thiosulfate followed by 3×20 mL saturated aqueous sodium chloride. The organic phase was then dried over sodium sulfate and concentrated under reduced pressure. The residue was subjected to silica gel chromatography, eluting with 10:1 hexane:diethyl ether. Fractions containing product were combined and concentrated under reduced pressure to provide 68% of the desired compound.

3-bromo-4-fluorophenol

A solution of 0.80 gm (3.43 mMol) O-acetyl 3-bromo-4-fluorophenol in 10 mL 6% diisopropylethylamine in methanol was stirred at room temperature for 8 hours. The reaction mixture was concentrated under reduced pressure at 0° C. to provide the desired compound.

3-bromo-4-fluorophenyl allyl ether

A mixture of 0.65 gm (3.43 mMol) 3-bromo-4-fluorophenol, 0.60 mL (6.86 mMol) allyl bromide, and 0.71 gm (5.15 mMol) potassium carbonate in 6 mL acetone was stirred at reflux for 13 hours. The reaction mixture was concentrated under reduced pressure and the residue subjected to silica gel chromatography, eluting with hexane. Fractions containing product were combined and concentrated under reduced pressure to provide 61% of the desired compound.

Claisen Rearrangement 3-bromo-4-fluorophenyl allyl ether was placed in a sealed tube and was deoxygenated by bubbling nitrogen through the liquid. The tube was sealed and then heated at 230° C. for 3 hours. After cooling to room temperature, the mixture is subjected to silica gel chromatography, eluting with 8:1 hexane:diethyl ether. The faster eluting product isomer was 2-allyl-4-fluoro-5-bromophenol. The slower eluting isomer was 2-allyl-3-bromo-4-fluorophenol. The isomers were isolated in a ratio of 3:2 respectively.

4-bromo-5-fluorobenzofuran

Beginning with 3 gm (13 mMol) 2-allyl-3-bromo-4-fluorophenol, the title compound was prepared in 98% yield essentially by the procedure described in Preparation XXXI with the exception that the cyclization/dehydration step was performed using sulfuric acid in toluene.

5-fluoro-6-bromobenzofuran

Beginning with 3.5 gm (15 mMol) 2-allyl-4-fluoro-5-bromophenol, the title compound was prepared in 90% yield essentially by the procedure described in Preparation XXXI with the exception that the cyclization/dehydration step was performed using sulfuric acid in toluene.

Preparation XXXVI

Alternate Synthesis of 4-chloro-5-fluoro-7-bromobenzofuran

A mixture of 90.4 gm (0.40 mole) 2-bromo-4-fluoro-5-chlorophenol (containing 10% 2-bromo-3-chloro-4-fluorophenol) and 64 gm (0.45 mole) hexamethylenetetramine was cooled in an ice bath. To this cooled mixture were added 306 mL trifluoroacetic acid. After stirring at about 0° C. for 15 minutes, the reaction mixture was heated at reflux for 1.5 hours. The reaction mixture was then cooled in an ice bath and treated with 439 mL of water followed by 220 mL 50% sulfuric acid. The reaction mixture was stirred without cooling for two hours. The reaction mixture was then diluted with 500 mL water and the resulting solid collected by filtration. The solid was washed with water until the wash was neutral (pH about 7). The solid was dried under reduced pressure and was then subjected to silica gel chromatography, eluting with a gradient of hexane containing from 0–2% ethyl acetate. Fractions containing the desired compound were combined and concentrated under reduced pressure to provide 57 gm (62%) 2-hydroxy-3-bromo-5-fluoro-6-chlorobenzaldehyde.

A suspension of 49.2 gm (0.19 mole) 2-hydroxy-3-bromo-5-fluoro-6-chlorobenzaldehyde and 127 gm (0.29 mole) (bromomethyl)triphenylphosphonium bromide in 230 mL tetrahydrofuran was cooled to 0° C. under a nitrogen atmosphere. To this were added dropwise 330 mL (0.33 mole) potassium tert-butoxide (1M in tetrahydrofuran) over 3 hours. An additional 90 mL (0.09 mole) potassium tert-butoxide (1M in tetrahydrofuran) were then added to react remaining starting material. The reaction mixture was diluted with 700 mL of hexane and the resulting precipitate removed by filtration. The recovered solid was slurried in 300 mL hexane and filtered 4 times. The combined filtrates were washed with 2×500 mL water followed by 500 mL saturated aqueous sodium chloride. The remaining organics were dried over sodium sulfate and concentrated under reduced pressure to provide a residual solid. This solid was slurried and filtered with 4×300 mL diethyl ether to remove triphenylphosphine oxide. The filtrates were concentrated and the residue subjected to silica gel chromatography, eluting with hexane. Fractions containing product were combined and concentrated under reduced pressure to provide 40 gm (83%) of the title compound as a white solid.

Preparation XXXVII 4,6-difluoro-7-bromobenzofuran

A solution of 2.6 gm (20 mmol) 3,5-difluorophenol in 20 mL carbon disulfide was cooled to 0° C. and then a solution of 1.02 mL (20 mMol) bromine in 10 mL carbon disulfide was added dropwise over 30 minutes. After stirring for an additional 30 minutes, the reaction mixture was warmed to room temperature and stirred for 1.5 hours. The reaction mixture was diluted with 200 mL diethyl ether and was washed sequentially with aqueous sodium metabisulfite and saturated aqueous sodium chloride. The organic phase was then dried over sodium sulfate and concentrated under reduced pressure. The residue was vacuum distilled to provide 2.5 gm (60%) of 2-bromo-3,5-difluorophenol (b.p.=65° C. (5 mm Hg)).

Beginning with 2-bromo-3,5-difluorophenol, the title compound was prepared essentially as described in Preparation XXII.

HRMS: Calculated for $C_8H_3OBrF_2$: 231.9335. Found: 231.9342.

EXAMPLE 1

1-(benzofur-5-yl)-2-aminopropane hydrochloride 1-(benzofur-5-yl)-2-propanone

A mixture of 1.90 gm (10 mmol) 5-bromobenzofuran, 183 mg (0.6 mmol) tri(o-tolyl)phosphine, 4.3 mL (15 mMol) tributyl tin methoxide, and 1.7 mL (15.4 mMol) isopropenyl acetate in 55 mL toluene was sparged with nitrogen for 15 minutes. To this mixture were then added 54 mg (0.3 mMol) palladium(II) chloride and the mixture was heated to 100° C. for 3 hours. The reaction mixture was cooled to room temperature and concentrated under reduced pressure. The residue was filtered through a bed of 100 gm silica gel, eluting with 1 liter of 1:1 hexane:ethyl acetate. Fractions containing crude product were combined and concentrated under reduced pressure. The residue was subjected to silica gel chromatography, eluting with a gradient of hexane containing from 0–20% ethyl acetate. Fractions containing product were combined and concentrated under reduced pressure to provide about 1.8 gm of the desired compound as an oil which gradually crystallized.

High Resolution MS: Calculated for $C_{11}H_{11}O_2$: Theory: 175.0759. Found: 175.0756.

Reductive Amination

A mixture of 1 gm (5.7 mMol) 1-(benzofur-5-yl)-2-propanone, 8.9 gm (115 mMol) ammonium acetate, and 2.8 gm powdered 3A molecular sieves in 60 mL methanol was stirred at room temperature for 1 hour. To this mixture were then added 5.8 mL (5.8 mMol) sodium cyanoborohydride (1.0 M in tetrahydrofuran) and the mixture was stirred for an additional 5 hours at room temperature under a nitrogen atmosphere. The reaction mixture was then filtered over a pad of celite and the pad was rinsed with 200 mL methanol and 200 mL dichloromethane. The combined filtrates were concentrated under reduced pressure and the resultant residue was partitioned between 200 mL dichloromethane and 20 mL water. The mixture was washed with two 25 mL portions of 5 N sodium hydroxide. The combined aqueous extracts were extracted with three 100 mL portions of dichloromethane. All of the organic phases were combined, washed with 25 mL 0.1 N sodium hydroxide followed by 25 mL water, dried over magnesium sulfate and concentrated under reduced pressure. The residue was subjected to silica gel chromatography, eluting with a gradient of dichloromethane containing 6% methanol to dichloromethane containing 9% methanol and 9% concentrated ammonium hydroxide. Fractions containing product were combined and concentrated under reduced pressure to provide 0.498 gm (49%) of 1-(benzofur-5-yl)-2-aminopropane.

This amine was dissolved in 20 mL ethyl acetate and then a 1 N solution of hydrogen chloride in diethyl ether was added dropwise. The resulting slurry was filtered, the solid washed with 3 mL ethyl acetate, and the solid dried under vacuum to provide 0.548 gm (91%) of the title compound.

m.p.=166–168° C.

EA: Calculated for $C_{11}H_{13}NO—HCl$: C, 62.41; H, 6.67; N, 6.62. Found: C, 62.19; H, 6.49; N, 6.60.

EXAMPLE 2

1-(benzofur-4-yl)-2-aminopropane hydrochloride

Beginning with 1.50 gm (7.65 mMol) 4-bromobenzofuran, 0.898 gm (67%) of 1-(benzofur-4-yl)-2-propanone were prepared essentially as described in Example 1.

High Resolution MS: Calculated for $C_{11}H_{11}O_2$: Theory: 175.0759. Found: 175.0756.

This ketone was converted to 0.637 gm (48%) 1-(benzofur-4-yl)-2-aminopropane essentially as described in Example 1. This amine was converted to the hydrochloride salt to provide the title compound.

EA: Calculated for $C_{11}H_{13}NO—HCl$: C, 62.41; H, 6.67; N, 6.62. Found: C, 62.11; H, 6.47; N, 6.58.

EXAMPLE 3

1-(benzofur-6-yl)-2-aminopropane hydrochloride

Beginning with 1.96 gm (10 mMol) 6-bromobenzofuran, 1.48 gm (85%) 1-(benzofur-6-yl)-2-propanone were prepared essentially as described in Example 1.

High Resolution MS: Calculated for $C_{11}H_{10}O_2$: Theory: 175.0759. Found: 175.0756.

1.0 gm (5.7 mMol) of this ketone was converted to 0.32 gm (37%) of 1-(benzofur-6-yl)-2-aminopropane essentially as described in Example 1. This amine was converted to the hydrochloride salt to provide the title compound.

EA: Calculated for $C_{11}H_{13}NO \cdot HCl$: C, 62.41; H, 6.67; N, 6.62. Found: C, 62.49; H, 6.65; N, 6.63.

EXAMPLE 4

1-(benzofur-7-yl)-2-aminopropane hydrochloride

Beginning with 1.96 gm (10 mMol) 7-bromobenzofuran, 1.80 gm (100%) 1-(benzofur-7-yl)-2-propanone were prepared essentially as described in Example 1.

High Resolution MS: Calculated for $C_{11}H_{11}O_2$: Theory: 175.0759. Found: 175.0760.

This ketone was converted to 0.83 gm (47%) of 1-(benzofur-7-yl)-2-aminopropane essentially as described in Example 1. This amine was converted to the hydrochloride salt to provide the title compound.

EA: Calculated for $C_{11}H_{13}NO \cdot HCl$: C, 62.41; H, 6.67; N, 6.62. Found: C, 62.19; H, 6.63; N, 6.93.

EXAMPLE 5

1-(4-methoxybenzofur-7-yl)-2-aminopropane hydrochloride

Beginning with 0.27 gm (1.18 mmol) 4-methoxy-7-bromobenzofuran, 0.18 gm (76%) 1-(4-methoxybenzofur-7-yl)-2-propanone were prepared essentially as described in Example 1.

m.p.=82–83° C.

EA: Calculated for $C_{12}H_{12}O_3$: Theory: C, 70.58; H, 5.92. Found: C, 70.70; H, 5.77.

0.15 gm (0.74 mMol) of this ketone was converted to 0.074 gm (49%) of 1-(4-methoxybenzofur-7-yl)-2-aminopropane essentially as described in Example 1. This amine was converted to the hydrochloride salt to provide the title compound.

EA: Calculated for $C_{12}H_{15}NO_2 \cdot HCl$: C, 59.63; H, 6.67; N, 5.79. Found: C, 59.53; H, 6.41; N, 5.54.

EXAMPLE 6

1-(5-methoxybenzofur-7-yl)-2-aminopropane hydrochloride

Beginning with 2.26 gm (10 mMol) 5-methoxy-7-bromobenzofuran, 1.75 gm (86%) 1-(5-methoxybenzofur-7-yl)-2-propanone were prepared essentially as described in Example 1. 1.0 gm (4.9 mmol) of this ketone was converted to 0.55 gm (54%) of 1-(5-methoxybenzofur-7-yl)-2-aminopropane essentially as described in Example 1. This amine was converted to the hydrochloride salt to provide the title compound.

m.p.=166–168° C.

EA: Calculated for $C_{12}H_{15}NO_2 \cdot HCl$: C, 59.63; H, 6.67; N, 5.79. Found: C, 59.84; H, 6.62; N, 5.77.

EXAMPLE 7

1-(6-methoxybenzofur-7-yl)-2-aminopropane hydrochloride

Beginning with 1.0 gm (4.4 mMol) 6-methoxy-7-bromobenzofuran, 0.86 gm (95%) 1-(6-methoxybenzofur-7-yl)-2-propanone were prepared essentially as described in Example 1.

High Resolution MS: Calculated for $C_{12}H_{13}O_3$: Theory: 205.0865. Found: 205.0866.

0.82 gm (4.0 mMol) of this ketone was converted to 0.62 gm (75%) of 1-(6-methoxybenzofur-7-yl)-2-aminopropane essentially as described in Example 1. This amine was converted to the hydrochloride salt to provide the title compound.

m.p.=144–146° C.

EA: Calculated for $C_{12}H_{15}NO_2 \cdot HCl$: C, 59.63; H, 6.67; N, 5.79. Found: C, 59.44; H, 6.50; N, 6.02.

EXAMPLE 8

1-(6-methoxybenzofur-5-yl)-2-aminopropane hydrochloride

Beginning with 1.0 gm (4.4 mMol) 5-bromo-6-methoxybenzofuran, 0.81 gm (90%) 1-(6-methoxybenzofur-5-yl)-2-propanone were prepared essentially as described in Example 1.

High Resolution MS: Calculated for $C_{12}H_{13}O_3$: Theory: 205.0865. Found: 205.0862.

0.85 gm (4.2 mMol) of this ketone was converted to 0.43 gm (50%) of 1-(6-methoxybenzofur-5-yl)-2-aminopropane essentially as described in Example 1. This amine was converted to the hydrochloride salt to provide the title compound.

EXAMPLE 9

1-(4-fluorobenzofur-7-yl)-2-aminopropane oxalate

Beginning with 0.30 gm (1.4 mMol) 4-fluoro-7-bromobenzofuran, 0.14 gm (50%) 1-(4-fluorobenzofur-7-yl)-2-propanone were prepared essentially as described in Example 1.

This ketone was converted to 0.73 gm (54%) of 1-(4-fluorobenzofur-7-yl)-2-aminopropane essentially as described in Example 1. This amine was converted to the oxalate salt to provide the title compound.

m.p.=172–174° C.

MS(FD) m/e=194 (M+1)

EXAMPLE 10

1-(5-fluorobenzofur-7-yl)-2-aminopropane hydrochloride

N-tert-butoxycarbonyl 1-(5-fluorobenzofur-7-yl)-2-aminopropane

A mixture of 19 gm (88.8 mMol) 5-fluoro-7-bromobenzofuran and 4.7 gm (193.3 mMol) magnesium turnings in 300 mL diethyl ether was stirred at 40° C. while 7.6 mL (88.2 mMol) 1,2-dibromoethane were added dropwise over 15 minutes. Thirty minutes after the addition was complete, the reaction mixture was cooled to −10° C. To this cooled mixture were then added 6.76 gm (32.8 mMol) copper(I) bromide-dimethylsulfide complex all at once followed by the dropwise addition of 13 gm (82.8 mmol) of N-tert-butoxycarbonyl-2-methylaziridine and 20 mL diethyl ether. The resulting mixture was stirred for 2 hours at −10–0° C. The reaction mixture was then diluted 1.5 L ethyl acetate and 150 mL of water. The resulting slurry was filtered through a pad of celite and the celite pad was washed with two 150 ml portions of ethyl acetate. The filtrate was separated and the organic phase was extracted with two 200 mL portions of water and one 200 mL portion of saturated aqueous sodium chloride. The remaining organic phase was then dried over magnesium sulfate and concentrated under reduced pressure. The residue was crystallized from hexane containing 20% ethyl acetate. This solid was subjected to silica gel chromatography, eluting with a gradient of hexane containing from 0–20% ethyl acetate. Fractions containing product were combined and concentrated under reduced pressure. The residue was crystallized from hexane to provide 13.5 gm (56%) of the desired compound.

$^1$H-NMR(CDCl$_3$): δ7.63 (d, J=2.2 Hz, 1H), 7.10 (dd, J=2.6 Hz, J=8.1 Hz, 1H), 6.83 (dd, J=2.6 Hz, J=9.9 Hz, 1H), 6.71 (d, J=2.2 Hz, 1H), 4.44 (bs, 1H), 4.07 (bs, 1H), 2.99 (m, 2H), 1.37 (s, 9H), 1.11 (d, J=6.6 Hz, 3H).

Deprotection

A mixture of 0.50 gm (1.7 mMol) N-tert-butoxycarbonyl 1-(5-fluorobenzofur-7-yl)-2-aminopropane in 6 mL 4N hydrogen chloride in dioxane was stirred for 1 hour at room temperature. The reaction mixture was concentrated under reduced pressure and the residue was suspended in 70 mL diethyl ether. The suspension was stirred for 16 hours at room temperature and was filtered to provide 0.37 gm (95%) of the title compound.

EA: Calculated for C$_{11}$H$_{12}$NOF—HCl: C, 57.52; H, 5.71; N, 6.10. Found: C, 57.40; H, 5.66; N, 5.92.

EXAMPLE 11

(S)-1-(5-fluorobenzofur-7-yl)-2-aminopropane hydrochloride (S)-N-tert-butoxycarbonyl 1-(5-fluorobenzofur-7-yl)-2-aminopropane Beginning with 0.94 gm (4.4 mMol) 5-fluoro-7-bromobenzofuran and 0.63 mg (4 mMol) (S)-(+)-N-tert-butoxycarbonyl-2-methylaziridine, 0.534 gm (46%) of the desired compound were prepared essentially as described in Example 10.

m.p.=120–121° C.

$^1$H-NMR(CDCl$_3$): δ7.63 (d, J=2.2 Hz, 1H), 7.10 (dd, J=2.6 Hz, J=8.1 Hz, 1H), 6.83 (dd, J=2.6 Hz, J=9.9 Hz, 1H), 6.71 (d, J=2.2 Hz, 1H), 4.44 (bs, 1H), 4.07 (bs, 1H), 2.99 (m, 2H), 1.37 (s, 9H), 1.11 (d, J=6.6 Hz, 3H).

MS(FD): m/e=294 (M+1)

EA: Calculated for C$_{16}$H$_{20}$NO$_3$F: C, 65.51; H, 6.87; N, 4.77. Found: C, 65.75; H, 7.10; N, 4.84.

OR: [α]$_D^{20}$=+24.79° (c=1.03, CH$_2$Cl$_2$)

Deprotection

Beginning with 0.50 gm (1.7 mMol) (S)-N-tert-butoxycarbonyl 1-(5-fluorobenzofur-7-yl)-2-aminopropane, 0.37 gm (95%) of the title compound were prepared essentially as described in Example 10.

EA: Calculated for C$_{11}$H$_{12}$NOF—HCl: C, 57.52; H, 5.71; N, 6.10. Found: C, 57.44; H, 5.42; N, 6.28.

OR: [α]$_D^{20}$=+11.64° (c=1.03, CH$_3$OH)

EXAMPLE 12

(R)-1-(5-fluorobenzofur-7-yl)-2-aminopropane hydrochloride (R)-N-tert-butoxycarbonyl 1-(5-fluorobenzofur-7-yl)-2-aminopropane Beginning with 5.7 gm (26.6 mMol) 5-fluoro-7-bromobenzofuran and 3.9 gm (24.8 mMol) (R)-(−)-N-tert-butoxycarbonyl- 2-methylaziridine, 3.22 gm (44%) of the desired compound were prepared essentially as described in Example 10.

MS(FD): m/e=294 (M+1)

OR: [α]$_D^{20}$=−28.99° (c=1.03, CH$_3$OH)

Deprotection

Beginning with 0.50 gm (1.7 mMol) (R)-N-tert-butoxycarbonyl 1-(5-fluorobenzofur-7-yl)-2-aminopropane, 0.37 gm (95%) of the title compound were prepared essentially as described in Example 10.

EA: Calculated for C$_{11}$H$_{12}$NOF—HCl: C, 57.52; H, 5.71; N, 6.10. Found: C, 57.75; H, 5.50; N, 6.26.

EXAMPLE 13

1-(7-fluorobenzofur-5-yl)-2-aminopropane hydrochloride

Beginning with 0.28 gm (1.3 mMol) 5-bromo-7-fluorobenzofuran, 0.26 gm (100%) 1-(7-fluorobenzofur-5-yl)-2-propanone were prepared essentially as described in Example 1.

$^1$H-NMR(CDCl$_3$): δ 7.64 (d, J=2.1 Hz, 1H), 7.18 (s, 1H), 6.89 (d, J=11.3 Hz, 1H), 6.76 (m, 1H), 3.75 (s, 2H), 2.17 (s, 3H).

This ketone was converted to 0.082 gm (32%) of 1-(7-fluorobenzofur-5-yl)-2-aminopropane essentially as described in Example 1. This amine was converted to the hydrochloride salt to provide the title compound.

$^1$H-NMR(DMSO-d$_6$): δ 8.07 (s, 1H), 7.94 (br s, 2H), 7.33 (s, 1H), 7.15 (d, J=11.8 Hz, 1H), 7.02 (s, 1H), 3.44 (m, 1H), 2.99 (dd, J=6.2, 13.4 Hz, 1H), 2.77 (dd, J=8.1, 13.2 Hz, 1H), 1.11 (d, J=6.2 Hz, 1H).

EXAMPLE 14

1-(6-fluorobenzofur-7-yl)-2-aminopropane oxalate

Beginning with 0.44 gm (2.05 mMol) 6-fluoro-7-bromobenzofuran, 1-(6-fluorobenzofur-7-yl)-2-propanone were prepared essentially as described in Example 1. This ketone was converted to 0.18 gm (37%) of 1-(6-fluorobenzofur-7-yl)-2-aminopropane essentially as described in Example 1. This amine was converted to the oxalate salt to provide the title compound.

m.p.=200–202° C.

MS(FD): m/e=194.3 (M+1)

EA: Calculated for C$_{11}$H$_{12}$NOF—C$_2$H$_2$O$_4$: C, 55.12; H, 4.98; N, 4.94. Found: C, 55.40; H, 5.17; N, 5.05.

EXAMPLE 15

1-(5-chlorobenzofur-7-yl)-2-aminopropane hydrochloride

Beginning with 1.00 gm (4.32 mMol) 5-chloro-7-fluorobenzofuran, 0.81 gm (90%) 1-(5-chlorobenzofur-7-yl)-2-propanone were prepared essentially as described in Example 1.

High Resolution MS: Calculated for C$_{11}$H$_{10}$O$_2$Cl: Theory: 209.0369. Found: 209.0367.

This ketone (0.70 gm, 3.35 mMol) was converted to 0.69 gm (99%) of 1-(5-chlorobenzofur-7-yl)-2-aminopropane essentially as described in Example 1. This amine was converted to the hydrochloride salt to provide the title compound.

EA: Calculated for $C_{11}H_{12}NOCl$—HCl: C, 53.68; H, 5.32; N, 5.69. Found: C, 53.92; H, 5.34; N, 5.62.

EXAMPLE 16

1-(2-bromo-5-fluorobenzofur-7-yl)-2-aminopropane hydrochloride

N-tert-butoxycarbonyl 1-(2-bromo-5-fluorobenzofur-7-yl)-2-aminopropane

To a solution of 0.50 gm (1.71 mMol) N-tert-butoxycarbonyl 1-(5-fluorobenzofur-7-yl)-2-aminopropane in 17 mL tetrahydrofuran at −78° C. were added 2.4 mL (3.84 mMol) n-butyllithium (1.6 M in hexane) dropwise. The resulting mixture was stirred for 1.5 hour and then 0.16 mL (1.86 mMol) dibromoethane were added. After stirring for an additional hour the reaction mixture was poured into a mixture of 25 mL saturated aqueous sodium bicarbonate and 50 mL diethyl ether. The phases were separated and the organic phase was washed with saturated aqueous sodium chloride. All aqueous phases were combined and extracted with 50 mL diethyl ether. All organic phases were combined, washed with saturated aqueous sodium chloride, dried over magnesium sulfate and concentrated under reduced pressure. The residue was subjected to silica gel chromatography, eluting with a gradient of hexane containing from 0 to 15% ethyl acetate. Fractions containing product were combined and concentrated under reduced pressure to provide 0.53 gm (89%) of the desired compound.

EA: Calculated for $C_{16}H_{19}BrFNO_3$: Theory: C, 51.63; H, 5.14; N, 3.76. Found: C, 51.51; H, 4.96; N, 3.70.

Deprotection

Beginning with 0.35 gm (0.94 mMol) N-tert-butoxycarbonyl 1-(2-bromo-5-fluorobenzofur-7-yl)-2-aminopropane, 0.15 gm (59%) of the title compound were prepared essentially as described in EXAMPLE 10.

MS(FD): m/e=272, 274 (M+1)

EA: Calculated for $C_{11}H_{11}NOBrF$—HCl: C, 42.82; H, 3.92; N, 4.54. Found: C, 43.11; H, 4.09; N, 4.47.

EXAMPLE 17

(S)-1-(2-bromo-5-fluorobenzofur-7-yl)-2-aminopropane hydrochloride (S)-N-tert-butoxycarbonyl 1-(2-bromo-5-fluorobenzofur-7-yl)-2-aminopropane Beginning with 0.29 gm (1.0 mMol) (S)-N-tert-butoxycarbonyl 1-(5-fluorobenzofur-7-yl)-2-aminopropane, 0.18 gm (48%) of the desired compound were prepared essentially as described in EXAMPLE 16.

EA: Calculated for $C_{16}H_{19}BrFNO_3$: Theory: C, 51.63; H, 5.14; N, 3.76. Found: C, 51.83; H, 5.19; N, 3.81.

Deprotection

Beginning with 0.18 gm (0.48 mMol) (S)-N-tert-butoxycarbonyl 1-(2-bromo-5-fluorobenzofur-7-yl)-2-aminopropane, 0.12 gm (82%) of the title compound were prepared essentially as described in EXAMPLE 10.

m.p.=202–205

MS(FD): m/e=272, 274 (M+1)

EA: Calculated for $C_{11}H_{11}NOBrF$—HCl: C, 42.82; H, 3.92; N, 4.54. Found: C, 44.28; H, 4.24; N, 4.34.

EXAMPLE 18

1-(3-bromo-5-fluorobenzofur-7-yl)-2-aminopropane hydrochloride

N-tert-butoxycarbonyl 1-(2,3-dibromo-2,3-dihydro-5-fluorobenzofur-7-yl)-2-aminopropane To a solution of 0.50 gm (1.7 mMol) N-tert-butoxycarbonyl 1-(5-fluorobenzofur-7-yl)-2-aminopropane in 17 mL carbon disulfide were added 50 μL (0.97 mmol) bromine and the reaction mixture was stirred for 4 hours at room temperature. A additional 50 μL of bromine were added and stirring was continued for 16 hours. The reaction mixture was concentrated under reduced pressure to provide 0.75 gm (98%) of the desired compound.

N-tert-butoxycarbonyl 1-(3-bromo-5-fluorobenzofur-7-yl)-2-aminopropane

This dibrominated material was dissolved in 15 mL dimethylsulfoxide and then 0.51 mL (3.41 mMol) 1,8-diazabicyclo[5.4.0]undec-7-ene were added dropwise. After stirring for 4 hours at room temperature under a nitrogen atmosphere, the reaction mixture was diluted with 200 mL ethyl acetate and extracted with two 25 mL portions of 0.1 N hydrochloric acid. The organic phase was washed with sequentially with saturated aqueous sodium bicarbonate and saturated aqueous sodium chloride, dried over sodium sulfate and concentrated under reduced pressure. The residue was subjected to silica gel chromatography, eluting with chloroform containing 1% diethyl ether. Fractions containing primarily the desired compound were combined and concentrated under reduced pressure. The residue was crystallized from hexane to provide the desired compound as a crystalline solid.

Alternatively, a solution of 4.09 mMol of the dibromide in 50 mL ethanol was cooled to 0° C. To this solution was added 6.54 mL (6.54 mMoL) potassium hydroxide (1M in ethanol) dropwise. The reaction mixture was allowed to warm gradually to room temperature. The desired compound was recovered by concentration of the reaction mixture under reduced pressure.

$^1$H-NMR(CDCl$_3$): δ 7.70 (s, 1H), 7.08 (dd, 1H), 6.95 (dd, 1H), 4.4 (br s, 1H), 4.05 (br m, 1H), 3.05 (m, 2H), 1.4 (s, 9H), 1.15 (d, 3H).

Deprotection

Beginning with 0.37 gm (0.98 mMol) N-tert-butoxycarbonyl 1-(3-bromo-5-fluorobenzofur-7-yl)-2-aminopropane, 0.16 gm (53%) of the title compound were prepared essentially as described in EXAMPLE 10.

EA: Calculated for $C_{11}H_{11}NOBrF$—HCl: C, 42.82; H, 3.92; N, 4.54. Found: C, 42.60; H, 3.92; N, 4.60.

EXAMPLE 19

1-(2-chloro-5-fluorobenzofur-7-yl)-2-aminopropane hydrochloride

N-tert-butoxycarbonyl 1-(2-chloro-5-fluorobenzofur-7-yl)-2-aminopropane

Beginning with 0.29 gm (1.0 mMol) N-tert-butoxycarbonyl 1-(5-fluorobenzofur-7-yl)-2-aminopropane and 0.16 gm (1.20 mMol) N-chlorosuccinimide, 0.14 gm (43%) of the desired compound were prepared essentially as described in EXAMPLE 16.

m.p.=133–135° C.

MS(FD): m/e=327, 329 (M+)

EA: Calculated for $C_{16}H_{19}ClFNO_3$: Theory: C, 58.63; H, 5.84; N, 4.27. Found: C, 58.80; H, 5.94; N, 4.28.

Deprotection

Beginning with 0.12 gm (0.38 mMol) N-tert-butoxycarbonyl 1-(2-chloro-5-fluorobenzofur-7-yl)-2-aminopropane, 0.088 gm (88%) of the title compound were prepared essentially as described in EXAMPLE 10.

m.p.=188° C.

EA: Calculated for $C_{11}H_{11}NOClF$—HCl: C, 50.02; H, 4.58; N, 5.30. Found: C, 49.83; H, 4.53; N, 5.13.

EXAMPLE 20

1-(3-chloro-5-fluorobenzofur-7-yl)-2-aminopropane hydrochloride

N-tert-butoxycarbonyl 1-(2,3-dichloro-2,3-dihydro-5-fluorobenzofur-7-yl)-2-aminopropane To a stirred solution of 0.50 gm (1.70 mMol) N-tert-butoxycarbonyl 1-(5-fluorobenzofur-7-yl)-2-aminopropane in 10 mL diethyl ether at 0° C. under a nitrogen atmosphere were added 4.6 mL (1.8 mMol) chlorine (0.4 M in diethyl ether) and this mixture was stirred at 0° C. for 1 hour. An additional 2 mL (0.8 mMol) of the chlorine solution were added and the reaction mixture was stirred for an additional 30 minutes at room temperature. A further 2 mL (0.8 mMol) of the chlorine solution were added and stirring was continued for an additional hour. A final 4 mL (1.6 mMol) portion of the chlorine solution were added and the mixture was stirred for 16 hours at 0° C. The reaction mixture was then diluted with 40 mL diethyl ether and washed with 30 mL 1N sodium thiosulfate followed by 10 mL saturated aqueous sodium chloride. The reaction mixture was dried over sodium sulfate and concentrated under reduced pressure. The residue was subjected to silica gel chromatography, eluting with hexane containing 7% ethyl acetate. Fractions containing product were combined and concentrated under reduced pressure to provide 0.30 gm (48%) of the desired compound as a white solid. This material is unstable and must be used immediately.

N-tert-butoxycarbonyl 1-(3-chloro-5-fluorobenzofur-7-yl)-2-aminopropane

A mixture of 0.30 gm (0.82 mMol) N-tert-butoxycarbonyl 1-(2,3-dichloro-2,3-dihydro-5-fluorobenzofur-7-yl)-2-aminopropane and 0.135 gm 18-crown-6 in 6.5 mL 1M potassium tert-butoxide in tert-butanol was stirred at 35° C. for 1 hour. The reaction mixture was diluted with 4 mL tert-butanol was continued for an additional 2.5 hours. The reaction mixture was cooled to room temperature and diluted with 50 mL diethyl ether followed by 5 mL water and 20 mL saturated aqueous ammonium chloride. The phases were separated and the aqueous phase was extracted with 25 mL diethyl ether. The organic phases were combined, dried over sodium sulfate and concentrated under reduced pressure to provide an off-white solid. This solid residue was subjected to silica gel chromatography, eluting with hexane containing 7% ethyl acetate. Fractions containing the desired compound were combined and concentrated under reduced pressure to provide 0.151 gm (56%) of the desired compound as a white solid.

m.p.=127–129° C.

MS(FD): m/e=327, 329 (M+)

EA: Calculated for $C_{16}H_{19}NO_3ClF$: C, 58.63; H, 5.84; N, 4.27. Found: C, 58.83; H, 5.54; N, 4.10.

Deprotection

Beginning with 0.14 gm (0.42 mMol) N-tert-butoxycarbonyl 1-(3-chloro-5-fluorobenzofur-7-yl)-2-aminopropane, 0.10 gm (90%) of the title compound were prepared essentially as described in EXAMPLE 10.

m.p.=172–174° C.

EA: Calculated for $C_{11}H_{11}NOClF$—HCl: C, 50.02; H, 4.58; N, 5.30. Found: C, 50.19; H, 4.79; N, 5.32.

EXAMPLE 21

1-(4,5-difluorobenzofur-7-yl)-2-aminopropane hydrochloride

Beginning with 0.38 gm (1.61 mMol) 4,5-difluoro-7-bromobenzofuran, 0.31 gm (92%) 1-(4,5-difluorobenzofur-7-yl)-2-propanone were prepared essentially as described in Example 1.

High Resolution MS: Calculated for $C_{11}H_9O_2F_2$: Theory: 211.0571. Found: 211.0573.

Beginning with 0.26 gm (1.25 mMol) 1-(4,5-difluorobenzofur-7-yl)-2-propanone, 0.14 gm (51%) of 1-(4,5-difluorobenzofur-5-yl)-2-aminopropane were prepared essentially as described in Example 1. This amine was converted to the hydrochloride salt to provide the title compound.

EA: Calculated for $C_{11}H_{11}NOF_2$—HCl: C, 53.35; H, 4.88; N, 5.66. Found: C, 53.18; H, 4.77; N, 5.60.

EXAMPLE 22

1-(3-methyl-5-fluorobenzofur-7-yl)-2-aminopropane oxalate

Beginning with 1.0 gm (4.37 mMol) 3-methyl-5-fluoro-7-bromobenzofuran, 1.1 gm crude 1-(3-methyl-5-fluorobenzofur-7-yl)-2-propanone were prepared essentially as described in Example 1.

Beginning with 1.0 gm (4.85 mMol) 1-(3-methyl-4-fluorobenzofur-7-yl)-2-propanone, 0.37 gm (37%) of 1-(3-methyl-5-fluorobenzofur-7-yl)-2-aminopropane were prepared essentially as described in Example 1. This amine was converted to the oxalate salt to provide the title compound.

m.p.=201–202° C.

MS(FD): m/e=208 (M+1)

EA: Calculated for $C_{12}H_{14}NOF$—$C_2H_2O_4$: C, 56.56; H, 5.43; N, 4.71. Found: C, 56.57; H, 4.66; N, 4.96.

EXAMPLE 23

1-(2-methyl-5-fluorobenzofur-7-yl)-2-aminopropane oxalate

Beginning with 0.75 gm (3.27 mMol) 2-methyl-5-fluoro-7-bromobenzofuran, 0.76 gm crude 1-(2-methyl-5-fluorobenzofur-7-yl)-2-propanone were prepared essentially as described in Example 1.

Beginning with 0.67 gm (3.25 mMol) 1-(2-methyl-4-fluorobenzofur-7-yl)-2-propanone, 0.31 gm (47%) of 1-(2-methyl-5-fluorobenzofur-7-yl)-2-aminopropane were prepared essentially as described in Example 1. This amine was converted to the oxalate salt to provide the title compound.

EXAMPLE 24

1-(3-cyano-5-fluorobenzofur-7-yl)-2-aminopropane hydrochloride

N-tert-butoxycarbonyl 1-(3-cyano-5-fluorobenzofur-7-yl)-2-aminopropane

A mixture of 0.20 gm (0.54 mMol) N-tert-butoxycarbonyl 1-(3-bromo-5-fluorobenzofur-7-yl)-2-aminopropane, 0.95 gm (5 mMol) copper(I) iodide, and 0.43 gm (4.78 mMol) copper(I) cyanide in 10 mL dimethylformamide was purged with nitrogen for 15 minutes. The mixture was then heated at 120° C. An additional equivalent of copper(I) iodide and copper(I) cyanide were added and the reaction continued at 120° C. for about 16 hours. After cooling to room temperature the reaction mixture was diluted with dichloromethane and then silica gel was added. The solvents were removed under reduced pressure and the dry silica gel remaining was loaded on the top of a silica gel column. The column was then eluted with a gradient of hexane containing from 17% to 20% ethyl acetate. Fractions containing product were combined and concentrated under reduced pressure to provide 0.010 gm (6%) of the desired compound.

High Resolution MS: Calculated for $C_{17}H_{20}N_2O_3F$: Theory: 319.1458. Found: 319.1461.

Deprotection

Beginning with 0.010 gm (0.03 mMol) N-tert-butoxycarbonyl 1-(3-cyano-5-fluorobenzofur-7-yl)-2-aminopropane, 0.0075 gm (98%) of the title compound were prepared essentially as described in EXAMPLE 10.

High Resolution MS: Calculated for $C_{12}H_{11}N_2O_3F$: Theory: 219.0933. Found: 219.0434.

EXAMPLE 25

1-(2-carboxamido-5-fluorobenzofur-7-yl)-2-aminopropane hydrochloride

N-tert-butoxycarbonyl 1-(3-carboxy-5-fluorobenzofur-7-yl)-2-aminopropane

A solution of 0.20 gm (0.68 mMol) N-tert-butoxycarbonyl 1-(5-fluorobenzofur-7-yl)-2-aminopropane in 35 mL tetrahydrofuran was cooled to −78° C. under a nitrogen atmosphere. To this solution were then added 0.96 mL (1.53 mMoL) n-butyllithium (1.6 M in hexane) dropwise, resulting in an orange solution. After 15 minutes carbon dioxide gas was bubbled into the reaction mixture, immediately discharging the orange color. The reaction mixture was diluted with 200 mL ethyl acetate, washed sequentially with 100 mL of water and 100 mL saturated aqueous sodium chloride, dried over magnesium sulfate and concentrated under reduced pressure. The residual solid was slurried in diethyl ether and filtered, providing 0.14 gm (60%) of the desired compound in two crops.

EA: Calculated for $C_{17}H_{20}NO_5F$: C, 60.53; H, 5.98; N, 4.15. Found: C, 60.47; H, 5.84; N, 4.02.

N-tert-butoxycarbonyl 1-(2-carboxamido-5-fluorobenzofur-7-yl)-2-aminopropane

To a solution of 0.20 gm (0.59 mMol) N-tert-butoxycarbonyl 1-(2-carboxy-5-fluorobenzofur-7-yl)-2-aminopropane in 30 mL tetrahydrofuran and 10 mL dichloromethane were added sequentially 0.09 gm (0.65 mMol) 1-hydroxybenzotriazole and 0.11 mL (0.65 mMol) diisopropylethylamine. The reaction mixture was cooled to 0° C. and then 0.12 gm (0.62 mMol) 1-(3-dimethylaminopropyl)-3-ethylcarbodiimide hydrochloride. The reaction mixture was then stirred for 3 hours at which point 0.03 mL (0.77 mMol) ammonium hydroxide were added. After stirring about 20 hours at room temperature the reaction mixture was concentrated under reduced pressure. The residue was diluted with 300 mL ethyl acetate and washed with sequentially with 100 mL 2 N sodium hydroxide, 200 mL saturated aqueous ammonium chloride, 100 mL water, and 100 mL saturated aqueous sodium chloride, dried over magnesium sulfate and concentrated under reduced pressure. The residue was subjected to silica gel chromatography, eluting with 1:1 hexane:ethyl acetate. Fractions containing product were combined and concentrated under reduced pressure to provide 0.055 gm (28%) of the desired compound.

Deprotection

Beginning with 0.05 gm (0.149 mMol) N-tert-butoxycarbonyl 1-(2-carboxamido-5-fluorobenzofur-7-yl)-2-aminopropane, the title compound was prepared essentially as described in EXAMPLE 10.

High Resolution MS: Calculated for $C_{12}H_{13}N_2O_2F$: Theory: 237.1039. Found: 237.1036.

EXAMPLE 26

1-(2-formyl-5-fluorobenzofur-7-yl)-2-aminopropane hydrochloride

N-tert-butoxycarbonyl 1-(2-formyl-5-fluorobenzofur-7-yl)-2-aminopropane

A solution of 0.50 gm (1.7 mMol) N-tert-butoxycarbonyl 1-(5-fluorobenzofur-7-yl)-2-aminopropane in 75 mL tetrahydrofuran was cooled to −78° C. under a nitrogen atmosphere. To this solution were then added 2.4 mL (3.81 mMoL) n-butyllithium (1.6 M in hexane) dropwise, resulting in an orange solution. After 5 minutes 0.66 mL (8.52 mMol) dimethylformamide were added dropwise. After stirring 18 hours at room temperature the reaction mixture was quenched by addition of 20 mL saturated aqueous ammonium chloride. The reaction mixture was partitioned between 300 mL ethyl acetate and 300 mL water. The phases were separated and the aqueous phase was extracted twice with 200 mL ethyl acetate. The organic phases were combined and washed sequentially with two 200 mL portions of water and one 200 mL portion of saturated aqueous sodium chloride, dried over magnesium sulfate and concentrated under reduced pressure. The residue was subjected to silica gel chromatography, eluting with hexane containing 20% ethyl acetate. Fractions containing product were combined and concentrated under reduced pressure to provide 0.38 gm (69%) of the desired compound as a yellow solid.

Deprotection

Beginning with 0.20 gm (0.62 mMol) N-tert-butoxycarbonyl 1-(2-formyl-5-fluorobenzofur-7-yl)-2-aminopropane, the title compound was prepared essentially as described in EXAMPLE 10.

EXAMPLE 27

1-(2-trimethylsilyl-5-fluorobenzofur-7-yl)-2-aminopropane hydrochloride

N-tert-butoxycarbonyl 1-(2-trimethylsilyl-5-fluorobenzofur-7-yl)-2-aminopropane

A solution of 0.20 gm (0.68 mMol) N-tert-butoxycarbonyl 1-(5-fluorobenzofur-7-yl)-2-aminopropane in 10 mL tetrahydrofuran was cooled to −78° C. under a nitrogen atmosphere. To this solution were then added 0.96 mL (1.53 mMoL) n-butyllithium (1.6 M in hexane) dropwise, resulting in an orange solution. After 50 minutes 0.14 mL (1.02 mMol) trimethylsilylisocyanate were added dropwise. After 15 minutes the reaction mixture was quenched by addition of 2 mL saturated aqueous ammonium chloride and was then allowed to warm to room temperature. The reaction mixture was partitioned between 150 mL ethyl acetate and 150 mL water. The phases were separated and the organic phase was washed sequentially with 150 mL water and 150 mL saturated aqueous sodium chloride, dried over magnesium sulfate and concentrated under reduced pressure. The residue was subjected to silica gel chromatography, eluting with 10:1 hexane:ethyl acetate. Fractions containing product were combined and concentrated under reduced pressure to provide the desired compound.

MS(FD): m/e=365 (M+)
EA: Calculated for $C_{19}H_{28}NO_3FSi$: C, 62.43; H, 7.72; N, 3.83. Found: C, 62.68; H, 7.65; N, 3.83.

Deprotection

Beginning with 0.13 gm (0.34 mMol) N-tert-butoxycarbonyl 1-(2-trimethylsilyl-5-fluorobenzofur-7-yl)-2-aminopropane, the title compound was prepared essentially as described in EXAMPLE 10.

EXAMPLE 28

1-(2-[N'-phenyl]carboxamido-5-fluorobenzofur-7-yl)-2-aminopropane hydrochloride

N-tert-butoxycarbonyl 1-(2-[N'-phenyl]carboxamido-5-fluorobenzofur-7-yl)-2-aminopropane A solution of 0.20 gm (0.68 mMol) N-tert-butoxycarbonyl 1-(5-fluorobenzofur-7-yl)-2-aminopropane in 10 mL tetrahydrofuran was cooled to −78° C. under a nitrogen atmosphere. To this solution were then added 0.96 mL (1.53 mMoL) n-butyllithium (1.6 M in hexane) dropwise, resulting in an orange solution. After 30 minutes 0.11 mL (1.02 mMol) phenylisocyanate were added dropwise. After about 1.5 hours the reaction mixture was quenched by addition of 2 mL saturated aqueous ammonium chloride and was then allowed to warm to room temperature. The reaction mixture was diluted with dichloromethane and then silica gel was added. The volatiles were removed under reduced pressure and the dry silica gel was added to the top of silica gel column. The column was then eluted with 6:1 hexane:ethyl acetate. Fractions containing product were combined and concentrated under reduced pressure to provide 0.096 gm (34%) of the desired compound as a white solid.
m.p.=154–156° C.

Deprotection

Beginning with 0.80 gm (0.19 mMol) N-tert-butoxycarbonyl 1-(2-[N'-phenyl]carboxamido-5-fluorobenzofur-7-yl)-2-aminopropane, 0.055 gm (81%) of the title compound were prepared as a white solid essentially as described in EXAMPLE 10.
m.p.>260° C.
EA: Calculated for $C_{18}H_{17}N_2O_2F$—HCl: C, 61.98; H, 5.20; N, 8.03. Found: C, 61.83; H, 5.28; N, 7.90.

EXAMPLE 29

1-(5-fluorobenzofur-7-yl)-3-aminobutane hydrochloride

Nitrogen was bubbled through a mixture of 1.0 gm (4.65 mMol) 5-fluoro-7-bromobenzofuran, 0.61 mL (6.98 mMol) 3-buten-2-ol, 0.057 gm (0.186 mMol) tri(o-tolyl)phosphine, and 0.47 gm (5.58 mmol) sodium bicarbonate in 35 mL N-methylpyrrolidinone for 10 minutes. To the mixture were then added 0.021 gm (0.093 mMol) palladium(II) acetate and the reaction mixture was heated to 140° C. for 3 hours. The reaction mixture was cooled to room temperature and diluted with 500 mL ethyl acetate. The organic phase was washed sequentially with three 500 mL portions of water and 500 mL saturated aqueous sodium chloride, dried over magnesium sulfate and concentrated under reduced pressure. The residue was subjected to silica gel chromatography, eluting with a gradient of hexane containing from 0–20% ethyl acetate. Fractions containing product were combined and concentrated under reduced pressure to provide 0.73 gm (76%) 4-(5-fluorobenzofur-7-yl)-2-butanone as a yellow oil.
EA: Calculated for $C_{12}H_{11}O_2F$: C, 69.89; H, 5.38. Found: C, 69.76; H, 5.29.

Beginning with 0.63 gm (3.05 mMol) 4-(5-fluorobenzofur-7-yl)-2-butanone, 1-(5-fluorobenzofur-7-yl)-3-aminobutane was prepared essentially as described in EXAMPLE 1. 0.36 gm (1.73 mMol) of this amine were treated with hydrogen chloride to prepare 0.32 gm (76%) of the title compound as a white solid.
EA: Calculated for $C_{12}H_{14}NOF$—HCl: C, 59.14; H, 6.20; N, 5.75. Found: C, 59.36; H, 6.18; N, 5.79.

EXAMPLE 30

1-(5-nitrobenzofur-7-yl)-2-aminopropane hydrochloride

Beginning with 3.8 gm (15.7 mMol) 5-nitro-7-bromobenzofuran, 2.4 gm (70%) 1-(5-nitrobenzofur-7-yl)-2-propanone were prepared as a pale yellow solid essentially as described in Example 1.

Beginning with 0.28 gm (1.28 mMol) 1-(5-nitrobenzofur-7-yl)-2-propanone, 0.15 gm (53%) of 1-(5-nitrobenzofur-7-yl)-2-aminopropane were prepared as a light yellow, waxy solid essentially as described in Example 1. This amine was converted to the hydrochloride salt to provide the title compound.
m.p.=216–217° C. (dec.)
MS(FD): m/e=221 (M+1)
EA: Calculated for $C_{11}H_{12}N_2O$—HCl-0.1H$_2$O: C, 51.11; H, 5.11; N, 10.84. Found: C, 50.95; H, 4.93; N, 10.67.

EXAMPLE 31

1-(5-aminobenzofur-7-yl)-2-aminopropane dihydrochloride

N-tert-butoxycarbonyl 1-(5-nitrobenzofur-7-yl)-2-aminopropane

A mixture of 1.60 gm (7.27 mMol) 1-(5-nitrobenzofur-7-yl)-2-aminopropane, 1.01 mL (7.27 mMol) triethylamine, and 1.59 gm (7.27 mMol) di-tert-butyl dicarbonate in 60 mL dichloromethane was stirred at room temperature for 18 hours. The reaction mixture was diluted with 60 ml dichloromethane and was then washed sequentially with two 50 mL portions of 0.1 N hydrochloric acid, 50 mL 2.5 N sodium hydroxide, and 25 mL saturated aqueous sodium chloride. The remaining organic phase was then dried over sodium sulfate and concentrated under reduced pressure. The residue was crystallized from diethyl ether to provide 1.72 gm (74%) of the desired compound as a white crystalline solid.

m.p.=131–132° C.

EA: Calculated for $C_{16}H_{20}N_2O_5$: C, 59.99; H, 6.29; N, 8.75. Found: C, 60.15; H, 6.35; N, 8.83.

N-tert-butoxycarbonyl 1-(5-[N'-tert-butoxycarbonyl]aminobenzofur-7-yl)-2-aminopropane A mixture of 0.43 gm (1.34 mMol) crude N-tert-butoxycarbonyl 1-(5-nitrobenzofur-7-yl)-2-aminopropane and 0.89 gm (13.4 mMol) zinc dust in 20 mL glacial acetic acid was stirred at room temperature for 75 minutes. The reaction mixture was filtered through a pad of celite and the filter pad was washed with four 40 mL portions of dichloromethane. The combined filtrates were neutralized by the addition of 100 mL ice cold 5 N sodium hydroxide. The phases were separated and the aqueous phase was extracted with 40 mL dichloromethane. The organic phases were combined, washed with 40 mL of 3:1 saturated aqueous sodium chloride:5 N sodium hydroxide, dried over sodium sulfate, and concentrated under reduced pressure. The residue was subjected to silica gel chromatography, eluting with 1:1 hexane:ethyl acetate. Fractions containing product were combined and concentrated under reduced pressure to provide 0.20 gm of the desired compound as a pale yellow oil.

MS(ion spray): m/e=391 (M+1)

Deprotection

Beginning with 0.20 gm (0.51 mMol) N-tert-butoxycarbonyl 1-(5-[N'-tert-butoxycarbonyl]aminobenzofur-7-yl)-2-aminopropane, 0.10 gm (74%) of the title compound were prepared as an off-white solid essentially as described in EXAMPLE 10.

High Resolution MS: Calculated for $C_{11}H_{15}N_2O$: Theory: 191.1184. Found: 191.1182.

EXAMPLE 32

1-(5-[N'-acetyl]aminobenzofur-7-yl)-2-aminopropane hydrochloride

N-tert-butoxycarbonyl 1-(5-aminobenzofur-7-yl)-2-aminopropane

A mixture of 0.23 gm (0.78 mMol) N-tert-butoxycarbonyl-1-(5-aminobenzofur-7-yl)-2-aminopropane, 163 μL (1.17 mMol) triethylamine, and 88 μL (0.93 mMol) acetic anhydride in 5 mL dichloromethane was stirred at room temperature under a nitrogen atmosphere for 18 hours. The reaction mixture was diluted with 35 mL dichloromethane and was washed sequentially with 15 mL 0.5 N hydrochloric acid, 15 mL 1.0 N sodium hydroxide, and 5 mL saturated aqueous sodium chloride. The remaining organic phase was dried over sodium sulfate and concentrated under reduced pressure. The residue was subjected to silica gel chromatography, eluting with 6:4 ethyl acetate:hexane. Fractions containing product were combined and concentrated under reduced pressure to provide 0.21 gm (80%) of the desired compound as a pale yellow foam.

High Resolution MS: Calculated for $C_{18}H_{25}N_2O_4$: Theory: 333.1814. Found: 333.1811.

Deprotection

Beginning with 0.049 gm (0.15 mmol) N-tert-butoxycarbonyl 1-(5-[N'-acetyl]aminobenzofur-7-yl)-2-aminopropane, 0.027 gm (68%) of the title compound were prepared as a pale yellow solid essentially as described in EXAMPLE 10.

m.p.=229–233° C. (dec.)

EA: Calculated for $C_{13}H_{16}N_2O_2$—HCl-0.5H$_2$O C, 56.22; H, 6.53; N, 10.09. Found: C, 56.23; H, 6.27; N, 9.94.

EXAMPLE 33

1-(5-[N'-acetyl N'-methyl]aminobenzofur-7-yl)-2-aminopropane hydrochloride

N-tert-butoxycarbonyl 1-(5-[N'-acetyl N'-methyl]aminobenzofur-7-yl)-2-aminopropane To a solution of 0.15 gm (0.45 mMol) N-tert-butoxycarbonyl 1-(5-[N'-acetyl]aminobenzo-fur-7-yl)-2-aminopropane in 4 mL tetrahydrofuran were added 0.018 gm (0.45 mMol) sodium hydride (60% in mineral oil). The reaction mixture was stirred for 10 minutes at room temperature under a nitrogen atmosphere, at which point 0.15 mL iodomethane were added. The reaction mixture was stirred for 1.5 hour at room temperature and was then quenched with 1 mL saturated aqueous ammonium chloride. The reaction mixture was diluted with 25 mL ethyl acetate and stirred vigorously. The organic phase was decanted off and the process was repeated. The combined organic extracts were combined and concentrated under reduced pressure. The residual oily solid was subjected to flash silica gel chromatography eluting with dichloromethane containing 4% methanol. Fractions containing the desired product were combined and concentrated under reduced pressure to provide a yellow oil. The oil was dissolved in diethyl ether and the solution was then concentrated under reduced pressure to provide 0.121 gm (78%) of the desired compound as an off-white foam.

Deprotection

Beginning with 0.040 gm (0.12 mMol) N-tert-butoxycarbonyl 1-(5-[N'-acetyl N'-methyl]aminobenzo-fur-7-yl)-2-aminopropane, 0.019 gm (58%) of the title compound were prepared as a solid essentially as described in EXAMPLE 10.

MS(ion spray): m/e=247 (M$^+$)

EXAMPLE 34

1-(5-[N'-methyl]aminobenzofur-7-yl)-2-aminopropane hydrochloride

N-tert-butoxycarbonyl 1-(5-[N'-methyl]aminobenzo-fur-7-yl)-2-aminopropane

A mixture of 0.081 gm (0.23 mMol) N-tert-butoxycarbonyl 1-(5-[N'-acetyl N'-methyl]aminobenzo-fur-7-yl)-2-aminopropane, 0.065 gm (1.17 mMol) potassium hydroxide, 2 mL methanol and 2 mL tetrahydrofuran was stirred at reflux for 2.5 hour. The reaction mixture was then allowed to stir at room temperature for about 18 hours at which point it was heated at reflux for 9 hours followed by about 18 hours at room temperature. To this mixture were then added 0.5 mL 50% aqueous sodium hydroxide and 2 mL dioxane and the resulting mixture was stirred at room temperature for about 18 hours. The reaction mixture was then partitioned between 2 mL of water and 25 mL diethyl ether. The organic phase was separated, dried over sodium sulfate, and concentrated under reduced pressure. The residual oil was subjected to flash silica gel chromatography, eluting with hexane containing 30% ethyl acetate. Fractions containing the desired product were combined and concentrated under reduced pressure to provide 0.042 gm (60%) of the desired compound as a colorless oil.

High Resolution MS: Calculated for $C_{17}H_{25}N_2O_3$: Theory: 305.1865. Found: 305.1868.

Deprotection

Beginning with 0.039 gm (0.13 mMol) N-tert-butoxycarbonyl 1-(5-[N'-methyl]aminobenzo-fur-7-yl)-2-aminopropane, 0.014 gm (39%) of the title compound were prepared as an off-white solid essentially as described in EXAMPLE 10.

High Resolution MS: Calculated for $C_{12}H_{17}N_2O$: Theory: 205.1341. Found: 205.1340.

EXAMPLE 35

1-(5-[N',N'-dimethyl]aminobenzofur-7-yl)-2-aminopropane hydrochloride

N-tert-butoxycarbonyl 1-(5-[N',N'-dimethyl]aminobenzofur-7-yl)-2-aminopropane

To a stirring mixture of 0.14 gm (0.48 mMol) 1-(5-aminobenzofur-7-yl)-2-aminopropane, 0.38 mL (5 mmol) formaldehyde (37% aqueous), and 0.091 gm sodium cyanoborohydride in 2 mL acetonitrile were added dropwise 50 µL glacial acetic acid over 3 minutes. The mixture was stirred for 2 hours at room temperature at which point an additional 50 µL of glacial acetic acid were added. After stirring at room temperature for 1.5 hours an additional charge of 0.38 mL (5 mmol) formaldehyde (37% aqueous), and 0.091 gm sodium cyanoborohydride, 2 mL acetonitrile, and 50 µL glacial acetic acid were added. After stirring for 1 hour at room temperature an additional 50 µL of glacial acetic acid were added. After stirring for an additional 30 minutes, the reaction mixture was diluted with 50 mL of diethyl ether and was washed sequentially with 2×15 mL 1N sodium hydroxide and 1×15 mL saturated aqueous sodium chloride. The organic phase was separated, dried over sodium sulfate, and concentrated under reduced pressure. The residual oil was subjected to flash silica gel chromatography, eluting with 1:1 hexane:ethyl acetate. Fractions containing product were combined and concentrated under reduced pressure to provide 0.087 gm (62%) of the desired compound as a white foam.

High Resolution MS: Calculated for $C_{18}H_{27}N_2O_3$: Theory: 319.2022. Found: 319.2018.

Deprotection

Beginning with 0.040 gm (0.13 mMol) N-tert-butoxycarbonyl 1-(5-[N',N'-dimethyl]aminobenzofur-7-yl)-2-aminopropane, 0.011 gm (29%) of the title compound were prepared as an off-white solid essentially as described in EXAMPLE 10.

m.p.=222–225° C. (dec.)

High Resolution MS: Calculated for $C_{13}H_{19}N_2O$: Theory: 219.1497. Found: 219.1499.

EXAMPLE 36

N-benzyl N'-(7-(2-aminoprop-1-yl)benzofur-5-yl) urea hydrochloride

N-benzyl N'-(7-(N'''-tert-butoxycarbonyl-2-aminoprop-1-yl)benzofur-5-yl)urea

A mixture of 0.10 gm (0.34 mMol) 1-(5-aminobenzofur-7-yl)-2-aminopropane and 0.43 µL (0.34 mMol) benzyl isocyanate in 4 mL dichloromethane was stirred at room temperature for about 18 hours. The white suspension was diluted with 3 mL diethyl ether and was filtered. The collected solid was washed with 2×1 mL diethyl ether and was dried under reduced pressure to provide 0.101 gm (70%) of the desired compound as a white solid.

m.p.=167–168° C.

EA: Calculated for $C_{24}H_{29}N_3O_4$: C, 68.07; H, 6.90; N, 9.92. Found: C, 68.06; H, 7.01; N, 9.98.

Deprotection

Beginning with 0.082 gm (0.19 mMol) N-benzyl N'-(7-(N'-tert-butoxycarbonyl-2-aminoprop-1-yl)benzofur-5-yl) urea, 0.054 gm (79%) of the title compound were prepared as an white solid essentially as described in EXAMPLE 10.

m.p.=215–217° C. (dec.)

EA: Calculated for $C_{19}H_{21}N_3O_2$—HCl: C, 63.42; H, 6.16; N, 11.68. Found: C, 63.21; H, 6.33; N, 11.60.

EXAMPLE 37

1-(5-[N'-methoxyacetyl]aminobenzofur-7-yl)-2-aminopropane hydrochloride

N-tert-butoxycarbonyl 1-(5-[N'-methoxyacetyl]aminobenzofur-7-yl)-2-aminopropane

A solution of 24 µL (0.31 mMol) methoxyacetic acid and 0.050 gm (0.31 mMol) carbonyldiimidazole in 2 mL tetrahydrofuran was stirred at room temperature under a nitrogen atmosphere for 45 minutes. At this point a solution of 0.090 gm (0.31 mMol) 1-(5-aminobenzofur-7-yl)-2-aminopropane in 1 mL tetrahydrofuran was added and the reaction mixture was stirred at room temperature for about 18 hours. The reaction mixture was then heated at reflux for 5 hours and was then diluted with 50 mL dichloromethane. This solution was then washed sequentially with 1×15 mL 2 N sodium hydroxide, 2×15 mL 1 N hydrochloric acid, and 1×15 mL saturated aqueous sodium chloride. The remaining organics were dried over sodium sulfate and concentrated under reduced pressure. The residual oil was subjected to flash silica gel chromatography, eluting with 1:1 hexane: ethyl acetate. Fractions containing product were combined and concentrated under reduced pressure to provide 0.060 gm 5 (54%) of the desired compound as a yellow-orange foam.

High Resolution MS: Calculated for $C_{19}H_{27}N_2O_5$: Theory: 363.1920. Found: 363.1918.

Deprotection

Beginning with 0.058 gm (0.16 mMol) N-tert-butoxycarbonyl 1-(5-[N'-methoxyacetyl]aminobenzofur-7-yl)-2-aminopropane, 0.036 gm (75%) of the title compound were prepared as an white solid essentially as described in EXAMPLE 10.

m.p.=240° C. (dec.)

EA: Calculated for $C_{19}H_{21}N_3O_2$—HCl-0.5$H_2O$ C, 54.64; H, 6.55; N, 9.10. Found: C, 54.64; H, 6.38; N, 8.85.

EXAMPLE 38

1-(5-hydroxybenzofur-7-yl)-2-aminopropane hydrochloride

A mixture of 0.73 gm (2.38 mMol) N-tert-butoxycarbonyl 1-(5-methoxybenzofur-7-yl)-2-aminopropane and 3.30 gm (28.52 mMol) pyridine hydrochloride were heated at 170° C. in a sealed tube for 15 hours. The mixture was cooled and the residue was dissolved in dichloromethane containing 10% methanol and 1% ammonium hydroxide. The solution was concentrated under reduced pressure and the pyridine remaining in the residue was removed azeotropically by diluting the residue with water and concentrating three times. The residue was crystallized from ethanol:diethyl ether. The 1-(5-hydroxybenzofur-7-yl)-2-aminopropane was recovered in the second crop and the filtrate. 0.045 gm (0.24 mMol) was treated with hydrochloric acid in diethyl ether to provide the title compound.

MS: m/e=192 (M+1)

$^1$H-NMR(DMSO-d$_6$): δ 9.2 (s, 1H), 8.07 (br s, 3H), 7.86 (d, J=2 Hz, 1H), 6.84 (d, J=2.4 Hz, 1H), 6.78 (d, J=2.0 Hz, 1H), 6.6 (d, J=2.4 Hz, 1H), 3.5 (br m, 1H), 3.12 (dd, J=5.4, 13.7 Hz, 1H), 2.87 (dd, J=9.3, 13.2 Hz, 1H), 1.08 (d, J=6.4 Hz, 3H).

EXAMPLE 39

1-amino-2-(5-fluorobenzofur-7-yl)propane

Ethyl 2-oxo-2-(5-fluorobenzofur-7-yl)acetate

A mixture of 1.01 gm (4.72 mMol) 5-fluoro-7-bromobenzofuran, 0.15 gm (6.14 mMol) magnesium(0), and 2 drops of 1,2-dibromoethane in 1 mL diethyl ether was stirred at room temperature until initiation of the Grignard formation had occurred (about 5–10 minutes). The mixture was then diluted with 8 mL of diethyl ether and heated at reflux for 30 minutes. This mixture was then added dropwise to a solution of 1.38 gm (9.44 mMol) diethyl oxalate in 3 mL tetrahydrofuran at −10° C. Once the addition was complete the reaction mixture was allowed to warm to room temperature and was then stirred at room temperature for 30 minutes. The reaction mixture was diluted with 20 volumes of ethyl acetate and was washed sequentially with 1N hydrochloric acid, water, and saturated aqueous sodium chloride. The remaining organics were concentrated under reduced pressure. The residue was subjected to flash silica gel chromatography, eluting with hexane containing 30% ethyl acetate. Fractions containing the desired product were combined and concentrated under reduced pressure to provide 0.894 gm (80%) of the desired compound.

Ethyl 2-acetoxy-2-(5-fluorobenzofur-7-yl)acetate

A mixture of 0.894 gm (3.78 mMol) ethyl 2-oxo-2-(5-fluorobenzofur-7-yl)acetate and 0.143 gm (3.78 mMol) sodium borohydride in 5 mL ethanol was stirred at room temperature for 1 hour. The reaction was quenched by the dropwise addition of water and was then concentrated under reduced pressure. The residue was dissolved in ethyl acetate, washed with water, and the organic phase concentrated under reduced pressure. The residual oil was subjected to flash silica gel chromatography, eluting with chloroform containing 2% methanol. Fractions containing ethyl 2-hydroxy-2-(5-fluorobenzofur-7-yl)acetate were combined and concentrated under reduced pressure. This residue was dissolved in 2.5 mL of pyridine and 2.5 mL acetic anhydride and was stirred at room temperature for 1 hour. The reaction mixture was then diluted with 25 volumes of ethyl acetate, washed with water, and concentrated under reduced pressure to provide 0.675 gm (64%) of the desired compound.

MS: m/e=281 (M+1)

Ethyl 2-(5-fluorobenzofur-7-yl)acetate

A mixture of 1.43 gm (5.10 mMol) ethyl 2-acetoxy-2-(5-fluorobenzofur-7-yl)acetate, 7.31 gm (40.8 mMol) hexamethylphosphoramide, 0.20 gm (6.12 mMol) methanol, and 153 mL (15.3 mMol) samarium(II) iodide tetrahydrofuran complex (0.1 M in tetrahydrofuran) was stirred at room temperature under a nitrogen atmosphere for 15 minutes. The reaction mixture was then diluted 10 fold with ethyl acetate, washed with water, and concentrated under reduced pressure to provide 1.09 gm (96%) of the desired compound.

Ethyl 2-(5-fluorobenzofur-7-yl)propionate

A solution of 1.09 gm (4.90 mMol) ethyl 2-(5-fluorobenzofur-7-yl)acetate in 5 mL tetrahydrofuran was cooled to −78° C. To this solution were slowly added 6.1 mL (6.13 mMol) lithium diisopropylamide (1.0 M in tetrahydrofuran) and the mixture was stirred at −78° C. for 1 hour. To this solution were then added 0.76 mL (12.25 mMol) iodomethane and the mixture was allowed to warm to room temperature over 1 hour. The reaction mixture was then diluted with ethyl acetate and the resulting solution washed sequentially with water, saturated aqueous sodium bicarbonate, and saturated aqueous sodium chloride. The remaining organic phase was concentrated under reduced pressure and the residue subjected to flash silica gel chromatography, eluting with hexane containing 20% ethyl acetate. Fractions containing product were combined and concentrated under reduced pressure to provide 0.723 gm (62%) of the desired compound.

2-(5-fluorobenzofur-7-yl)propionamide

To a solution of 0.27 gm (1.15 mMol) ethyl 2-(5-fluorobenzofur-7-yl)propionate in 4 mL dimethylformamide were added sequentially 0.16 mL (3.91 mMol) freshly distilled formamide and 0.81 mL (0.80 mMol) sodium methoxide (1 M in methanol) dropwise and the resulting mixture was heated at 100° C. for 45 minutes. The reaction mixture was cooled to room temperature and was then diluted with 25 volumes of ethyl acetate. The mixture was then washed sequentially with water and saturated aqueous sodium chloride, and concentrated under reduced pressure. The residue was subjected to flash silica gel chromatography, eluting with 2:1 ethyl acetate:hexane. Fractions containing product were combined and concentrated under reduced pressure to provide 0.060 gm (25%) of the desired compound.

MS: m/e=208 (M+1)

Reduction of Amide

To a solution of 0.06 gm (0.29 mMol) ethyl 2-(5-fluorobenzofur-7-yl)propionamide in 1.5 mL tetrahydrofuran were added 0.87 mL (0.87 mMol) borane tetrahydrofuran complex (1.0 M in tetrahydrofuran). The reaction mixture was stirred at room temperature for 2 hours and was then heated at reflux for 2 hours. The reaction mixture was cooled to room temperature and was then concentrated under reduced pressure. The residue was treated with a 1:1 mixture of methanol and 1N hydrochloric acid for 1 hour and was again concentrated under reduced pressure. The residue was dissolved in water, made basic with 5N sodium hydroxide, and extracted well with ethyl acetate. The organic phases were combined and concentrated under reduced pressure. The residue was subjected to silica gel chromatography, eluting with ethyl acetate containing 5% methanol and 5% triethylamine. Fractions containing product were combined and concentrated under reduced pressure to provide the title compound.

MS: m/e=195 (M+2)

EXAMPLE 40

1-(3-trifluoromethyl-5-fluorobenzofur-7-yl)-2-aminopropane oxalate

Beginning with 0.10 gm (0.35 mMol) 3-trifluoromethyl-5-fluoro-7-bromobenzofuran, 1-(3-trifluoromethyl-5-fluorobenzofur-7-yl)-2-propanone were prepared essentially as described in Example 1.

This ketone (0.042 gm, 0.17 mMol) was converted to 0.018 gm (42%) of 1-(3-trifluoromethyl-5-fluorobenzofur-7-yl)-2-aminopropane essentially as described in Example 1. This amine was converted to the oxalate salt to provide the title compound.

MS: m/e=263 (M+2)

EXAMPLE 41

1-(5-methoxycarbonylbenzofur-7-yl)-2-aminopropane oxalate

Beginning with 1.00 gm (4.12 mMol) 5-methoxycarbonyl-7-bromobenzofuran, 0.50 gm (55%) 1-(5-(methoxycarbonyl)benzofur-7-yl)-2-propanone were prepared essentially as described in Example 1.

This ketone was converted to 0.38 gm (75%) of 1-(5-(methoxycarbonyl)benzofur-7-yl)-2-aminopropane essentially as described in Example 1. This amine was converted to the oxalate salt to provide the title compound.

Standard Procedure for Preparation of Amides

A mixture of 1 equivalent N-tert-butoxycarbonyl 1-(5-carboxybenzofur-7-yl)-2-aminopropane, 1.2 equivalents 1-(3-dimethylaminopropyl)-3-ethylcarbodiimide hydrochloride, and 1.2 equivalents of an appropriate amine in dichloromethane are stirred at room temperature for about 18 hours. The reaction mixture is then washed with water and concentrated under reduced pressure. The residue is then crystallized from a mixture of hexane and ethyl acetate to provide the N-tert-butoxycarbonyl 1-(N'-[substituted] 5-carboxamidobenzofur-7-yl)-2-aminopropane. This material is then treated with trifluoroacetic acid followed by 1N hydrochloric acid to deprotect the 2-amino group. Lyophilization provides the hydrochloride salts of the desired amides. This procedure was applied to the preparation of the compounds of EXAMPLES 42–45.

EXAMPLE 42

1-(N'-[butyl] 5-carboxamidobenzofur-7-yl)-2-aminopropane hydrochloride

Beginning with 0.050 gm (0.16 mMol) N-tert-butoxycarbonyl 1-(5-carboxybenzofur-7-yl)-2-aminopropane and 0.013 gm (0.17 mMol) butylamine, the title compound was prepared as previously described.

MS: m/e=276 (M+2)

EXAMPLE 43

1-(N'-[benzyl] 5-carboxamidobenzofur-7-yl)-2-aminopropane hydrochloride

Beginning with 0.050 gm (0.16 mMol) N-tert-butoxycarbonyl 1-(5-carboxybenzofur-7-yl)-2-aminopropane and 0.018 gm (0.17 mMol) benzylamine, the title compound was prepared as previously described.

MS: m/e=308 (M+2)

EXAMPLE 44

1-(N'-[1-phenyleth-2-yl] 5-carboxamidobenzofur-7-yl)-2-aminopropane hydrochloride Beginning with 0.050 gm (0.16 mMol) N-tert-butoxycarbonyl 1-(5-carboxybenzofur-7-yl)-2-aminopropane and 0.021 gm (0.17 mMol) phenethylamine, the title compound was prepared as previously described.

MS: m/e=322 (M+1)

EXAMPLE 45

1-(N'-[1-(pyridin-2-yl)eth-2-yl] 5-carboxamidobenzofur-7-yl)-2-aminopropane dihydrochloride Beginning with 0.050 gm (0.16 mMol) N-tert-butoxycarbonyl 1-(5-carboxybenzofur-7-yl)-2-aminopropane and 0.021 gm (0.17 mMol) 1-(pyridin-2-yl)eth-2-ylamine, the title compound was prepared as previously described.

MS: m/e=325 (M+1)

EXAMPLE 46

1-(N'-[1-(pyridin-2-yl)eth-2-yl] 5-carboxamidobenzofur-7-yl)-2-aminopropane oxalate N-tert-butoxycarbonyl 1-(N'-[1-(pyridin-2-yl)eth-2-yl] 5-carboxamidobenzofur-7-yl)-2-aminopropane A mixture of 0.175 gm (0.55 mMol) N-tert-butoxycarbonyl 5-carboxybenzofur-7-yl)-2-aminopropane, 0.116 gm (0.60 mMol) 1-(3-dimethylaminopropyl)-3-ethylcarbodiimide hydrochloride, 66 µL (0.55 mmol) 2-(2-ethylamino)pyridine, and a trace of dimethylaminopyridine in 5 mL dichloromethane was stirred at room temperature until all starting material was consumed. The reaction mixture was then washed sequentially with saturated aqueous sodium bicarbonate and saturated aqueous sodium chloride, dried over sodium sulfate and concentrated under reduced pressure. The residue was subjected to silica gel chromatography, eluting with dichloromethane containing 1% methanol saturated with ammonia. Fractions containing the desired product were combined and concentrated under reduced pressure to provide 0.164 gm (70%) of the desired compound as a white solid.

MS: m/e=424 (M+1)

Deprotection

A mixture of 0.153 gm (0.36 mMol) N-tert-butoxycarbonyl 1-(N'-[1-(pyridin-2-yl)eth-2-yl] 5-carboxamidobenzofur-7-yl)-2-aminopropane and 3 mL trifluoroacetic acid was stirred at room temperature for about 1.5 hours. The reaction mixture was concentrated under reduced pressure and the residue taken up in water. This aqueous solution was made basic by the addition of aqueous sodium hydroxide. This solution was extracted well with ethyl acetate. This solution was treated with a solution of oxalic acid in ethyl acetate and the solid collected to provide the title compound.

MS: m/e=324 (M+)

EXAMPLE 47

1-(N'-[1-(pyridin-3-yl)eth-2-yl] 5-carboxamidobenzofur-7-yl)-2-aminopropane dihydrochloride Beginning with N-tert-butoxycarbonyl 5-carboxybenzofur-7-yl)-2-aminopropane and 3-(2-ethylamino)pyridine, the title compound was prepared essentially as described in EXAMPLE 46.
MS: m/e=324 (M+)

EXAMPLE 48

1-(N'-[1-(pyridin-4-yl)eth-2-yl] 5-carboxamidobenzofur-7-yl)-2-aminopropane dihydrochloride Beginning with N-tert-butoxycarbonyl 5-carboxybenzofur-7-yl)-2-aminopropane and 4-(2-ethylamino)pyridine, the title compound was prepared essentially as described in EXAMPLE 46.
MS: m/e=324 (M+)

EXAMPLE 49

1-(N'-[carboxymethyl] 5-carboxamidobenzofur-7-yl)-2-aminopropane trifluoroacetate Beginning with N-tert-butoxycarbonyl 5-carboxybenzofur-7-yl)-2-aminopropane and glycine tert-butyl ester hydrochloride, the title compound was prepared essentially as described in EXAMPLE 46.

EXAMPLE 50

1-(5-carboxamidobenzofur-7-yl)-2-aminopropane hydrochloride

Beginning with N-tert-butoxycarbonyl 5-carboxybenzofur-7-yl)-2-aminopropane and ammonium hydroxide, the title compound was prepared essentially as described in EXAMPLE 46.
MS: m/e=219 (M+1)

EXAMPLE 51

1-(N'-[methyl] 5-carboxamidobenzofur-7-yl)-2-aminopropane hydrochloride

Beginning with N-tert-butoxycarbonyl 5-carboxybenzofur-7-yl)-2-aminopropane and methylamine hydrochloride, the title compound was prepared essentially as described in EXAMPLE 46.
MS: m/e=233 (M+)
EA: Calculated for $C_{13}H_{17}N_2O_2$—HCl-0.2$H_2O$ C, 57.33; H, 6.44; N, 10.29. Found: C, 57.20; H, 6.34; N, 9.97.

EXAMPLE 52

1-(N'-[isopropyl] 5-carboxamidobenzofur-7-yl)-2-aminopropane hydrochloride

Beginning with N-tert-butoxycarbonyl 5-carboxybenzofur-7-yl)-2-aminopropane and isopropylamine, the title compound was prepared essentially as described in EXAMPLE 46.
MS: m/e=261 (M+)
EA: Calculated for $C_{15}H_{21}N_2O_2$—HCl-0.5$H_2O$ C, 58.91; H, 7.25; N, 9.16. Found: C, 58.88; H, 7.46; N, 9.13.

EXAMPLE 53

1-(5-isopropylbenzofur-7-yl)-2-aminopropane hydrochloride

Beginning with 0.33 gm (1.5 mMol) 1-(5-isopropylbenzofur-7-yl)-2-propanone, 0.22 gm (66%) of 1-(5-isopropylbenzofur-7-yl)-2-aminopropane was prepared essentially as described in Example 1. This amine was converted to the hydrochloride salt to provide the title compound.
MS(FD): m/e=218 (M+1)
EA: Calculated for $C_{14}H_{19}NO$—HCl: C, 66.26; H, 7.94; N, 5.52. Found: C, 66.29; H, 8.04; N, 5.77.

EXAMPLE 54

1-(5-sec-butylbenzofur-7-yl)-2-aminopropane hydrochloride

Beginning with 0.32 gm (1.4 mMol) 1-(5-sec-butylbenzofur-7-yl)-2-propanone, 1-(5-sec-butylbenzofur-7-yl)-2-aminopropane was prepared essentially as described in Example 1. This amine was converted to the hydrochloride salt to provide the title compound.
MS(FD): m/e=232 (M+1)

EXAMPLE 55

1-(5-tert-butylbenzofur-7-yl)-2-aminopropane hydrochloride

Beginning with 2.0 mMol 1-(5-tert-butylbenzofur-7-yl)-2-propanone, 0.19 gm (39%) of 1-(5-tert-butylbenzofur-7-yl)-2-aminopropane was prepared essentially as described in Example 1. This amine was converted to the hydrochloride salt to provide the title compound.
MS(FD): m/e=232 (M+1)
EA: Calculated for $C_{14}H_{19}NO$—HCl-0.12$H_2O$: C, 66.74; H, 8.30; N, 5.19. Found: C, 66.75; H, 8.36; N, 5.63.

EXAMPLE 56

1-(5-cyanobenzofur-7-yl)-2-aminopropane hydrochloride

Beginning with 0.142 gm (0.71 mMol) 1-(5-cyanobenzofur-7-yl)-2-propanone, 0.077 gm (54%) 1-(5-cyanobenzofur-7-yl)-2-aminopropane was prepared essentially as described in Example 1. This amine was converted to the hydrochloride salt to provide the title compound.
MS(FD): m/e=201 (M+1)

EXAMPLE 57

1-(4-trifluoromethylbenzofur-7-yl)-2-aminopropane hydrochloride

Beginning with 0.47 gm (1.77 mMol) 4-trifluoromethyl-7-bromobenzofuran, 0.28 gm (66%) 1-(4-trifluoromethylbenzofur- 7-yl)-2-propanone were prepared essentially as described in Example 1.
This ketone was converted to 1-(4-trifluoromethylbenzofur-7-yl)-2-aminopropane essentially as described in Example 1. This amine was converted to the hydrochloride salt to provide 0.13 gm (39%) of the title compound.

EXAMPLE 58

1-(5-trifluoromethylbenzofur-7-yl)-2-aminopropane hydrochloride

Beginning with 0.47 gm (1.77 mMol) 5-trifluoromethyl-7-bromobenzofuran, 0.20 gm (48%) 1-(5-trifluoromethylbenzofur-7-yl)-2-propanone were prepared essentially as described in Example 1.

This ketone was converted to 1-(5-trifluoromethylbenzofur-7-yl)-2-aminopropane essentially as described in Example 1. This amine was converted to the hydrochloride salt to provide 0.12 gm (51%) of the title compound.

EA: Calculated for $C_{12}H_{12}NOF_3$—HCl: C, 51.53; H, 4.69; N, 5.01. Found: C, 51.68; H, 4.64; N, 5.01.

EXAMPLE 59

(R)-1-(5-trifluoromethylbenzofur-7-yl)-2-aminopropane hydrochloride (R)-N-tert-butoxycarbonyl 1-(5-trifluoromethylbenzofur-7-yl)-2-aminopropane Beginning with 0.256 gm (0.97 mMol) 5-trifluoromethyl-7-bromobenzofuran and 0.142 gm (0.90 mMol) (R)-(−)-N-tert-butoxycarbon-yl-2-methylaziridine, 0.077 gm (23%) of the desired compound were prepared essentially as described in Example 10.

Deprotection

Beginning with 0.077 gm (0.22 mMol) (R)-N-tert-butoxycarbonyl 1-(5-trifluoromethylbenzofur-7-yl)-2-aminopropane, 0.018 gm (28%) of the title compound were prepared essentially as described in Example 10.

EXAMPLE 60

1-(5-hydroxymethylbenzofur-7-yl)-2-aminopropane hydrochloride

A mixture of 0.12 gm (0.52 mmol) 5-hydroxymethyl-7-bromobenzofuran 0.070 gm (1.03 mMol) imidazole, and 0.078 gm (0.52 mMol), 0.070 gm (1.03 mMol) imidazole, and 0.078 gm (0.52 mMol) tert-butyldimethylsilyl chloride in 1 mL dimethylformamide was stirred at room temperature for 18 hours. The reaction mixture was diluted with hexane and washed well with water. The remaining organics were dried over magnesium sulfate and concentrated under reduced pressure to provide 0.41 gm (82%) of 5-tert-butyldimethylsilyloxymethyl-7-bromobenzofuran. This material was reacted essentially as described in EXAMPLE 1 to provide 0.085 gm (24%) 1-(5-tert-butyldimethylsilyloxymethylbenzofur-7-yl)-2-aminopropane. This material was treated with tetrabutylammonium fluoride in tetrahydrofuran for 1 hour at room temperature. The reaction mixture was partitioned between ethyl acetate and water. The phases were separated and the organic phase washed well with water. The remaining organics were concentrated under reduced pressure and the residue subjected to silica gel chromatography, eluting with dichloromethane containing 2% methanol saturated with ammonia. Fractions containing product were combined and concentrated under reduced pressure to provide 0.028 gm (50%) of 1-(5-hydroxymethylbenzofur-7-yl)-2-aminopropane. The title compound was prepared by reacting this amine with hydrochloric acid.

MS(FD): m/e=207 (M+2)

EXAMPLE 61

1-(5-methoxymethylbenzofur-7-yl)-2-aminopropane hydrochloride

Beginning with 0.40 gm (1.64 mMol) 5-methoxymethyl-7-bromobenzofuran, 0.18 gm (51%) 1-(5-methoxymethylbenzofur-7-yl)-2-propanone were prepared essentially as described in Example 1.

This ketone was converted to 1-(5-methoxymethylbenzofur-7-yl)-2-aminopropane essentially as described in Example 1. This amine was converted to the hydrochloride salt to provide the title compound.

MS(FD): m/e=220 (M+1)

EXAMPLE 62

1-(5-[N,N-dimethyl]carboxamidobenzofur-7-yl)-2-aminopropane hydrochloride

Beginning with 0.10 gm (0.37 mMol) 5-[N,N-dimethyl]carboxamido-7-bromobenzofuran, 0.077 gm (85%) 1-(5-[N,N-dimethyl]carboxamidobenzofur-7-yl)-2-propanone were prepared essentially as described in Example 1.

This ketone was converted to 1-(5-[N,N-dimethyl]-carboxamidobenzofur-7-yl)-2-aminopropane essentially as described in Example 1. This amine was converted to the hydrochloride salt to provide the title compound as a white solid.

MS(FD): m/e=247 (M+1)

EXAMPLE 63

1-(4,6-dichlorobenzofur-7-yl)-2-aminopropane hydrochloride

Beginning with 4,6-dichloro-7-bromobenzofuran, the title compound was prepared essentially as described in EXAMPLE 1.

MS(FD): m/e=244 (M⁺)

EA: Calculated for $C_{11}H_{10}NOCl_2$—HCl: C, 47.09; H, 4.31; N, 4.99. Found: C, 47.29; H, 4.01; N, 4.91.

EXAMPLE 64

1-(5-[4-chloro-5-fluorobenzofur-7-yl)-2-aminopropane hydrochloride

Beginning with 0.24 gm (0.95 mMol) 4-chloro-5-fluoro-7-bromobenzofuran, 0.14 gm (65%) 1-(4-chloro-5-fluorobenzofur-7-yl)-2-propanone were prepared essentially as described in Example 1.

This ketone was converted to 1-(4-chloro-5-fluorobenzofur-7-yl)-2-aminopropane essentially as described in Example 1. This amine was converted to the hydrochloride salt to provide 0.080 gm (49%) of the title compound as a white solid.

EXAMPLE 65

1-(4,5,6-trifluorobenzofur-7-yl)-2-aminopropane oxalate

Beginning with 4,5,6-trifluoro-7-bromobenzofuran, the title compound was prepared essentially as described in EXAMPLE 1.

MS(FD): m/e=229 (M⁺)

EXAMPLE 66

1-(3-methylbenzofur-7-yl)-2-aminopropane oxalate

Beginning with 3-methyl-7-bromobenzofuran, the title compound was prepared essentially as described in EXAMPLE 1.
MS(FD): m/e=190 (M+1)

EXAMPLE 67

1-(3-ethyl-5-fluorobenzofur-7-yl)-2-aminopropane oxalate

Beginning with 3-ethyl-5-fluoro-7-bromobenzofuran, the title compound was prepared essentially as described in EXAMPLE 1.
MS(FD): m/e=222 (M+1)

EXAMPLE 68

1-(3-isopropyl-5-fluorobenzofur-7-yl)-2-aminopropane oxalate

Beginning with 3-isopropyl-5-fluoro-7-bromobenzofuran, the title compound was prepared essentially as described in EXAMPLE 1.
MS(FD): m/e=236 (M+1)

EXAMPLE 69

1-(3-phenyl-5-fluorobenzofur-7-yl)-2-aminopropane oxalate

Beginning with 3-phenyl-5-fluoro-7-bromobenzofuran, the title compound was prepared essentially as described in EXAMPLE 1.
MS(FD) m/e=252 (M+1)

EXAMPLE 70

1-(3,4-dimethyl-5-fluorobenzofur-7-yl)-2-aminopropane oxalate

Beginning with 3,4-dimethyl-5-fluoro-7-bromobenzofuran, the title compound was prepared essentially as described in EXAMPLE 1.
MS(FD): m/e=222 (M+1)

EXAMPLE 71

1-(4,5,6-trimethylbenzofur-7-yl)-2-aminopropane oxalate

Beginning with 4,5,6-trimethyl-7-bromobenzofuran, the title compound was prepared essentially as described in EXAMPLE 1.
MS(FD): m/e=218 (M+1)

EXAMPLE 72

1-(4,6-dimethyl-5-chlorobenzofur-7-yl)-2-aminopropane oxalate

Beginning with 4,6-dimethyl-5-chloro-7-bromobenzofuran, the title compound was prepared essentially as described in EXAMPLE 1.

EXAMPLE 73

2-(5-fluorobenzofur-7-yl)-1-aminoethane oxalate

Beginning with 2-(5-fluorobenzofur-7-yl)propionamide (EXAMPLE 39), 2-(5-fluorobenzofur-7-yl)-1-aminoethane was prepared by borane reduction essentially as described in EXAMPLE 39. This amine was treated with oxalic acid to provide the title compound.
MS: m/e=181 (M+2)

EXAMPLE 74

2-(5-fluorobenzofur-7-yl)-1-aminobutane oxalate

Beginning with 5-fluoro-7-bromobenzofuran, 2-(5-fluorobenzofur-7-yl)-1-aminobutane was prepared essentially as described in EXAMPLE 39. This amine was treated with oxalic acid to provide the title compound.

EXAMPLE 75

2-(5-fluorobenzofur-7-yl)-3-phenylprop-1-ylamine oxalate

Beginning with 5-fluoro-7-bromobenzofuran, 2-(5-fluorobenzofur-7-yl)-3-phenylprop-1-ylamine was prepared essentially as described in EXAMPLE 39. This amine was treated with oxalic acid to provide the title compound.
MS: m/e=270 (M+1)

EXAMPLE 76

2-methyl-2-(5-fluorobenzofur-7-yl)-1-aminopropane hydrochloride

Ethyl 2-methyl-2-(5-fluorobenzofur-7-yl)propionate

A solution of 0.17 gm (0.71 mMol) ethyl 2-(5-fluorobenzofur-7-yl)propionate (EXAMPLE 39) in 2.5 mL tetrahydrofuran was cooled to −78° C. To this solution were added 0.89 mL (0.89 mmol) lithium bis(trimethylsilyl)amide (1.0 M in hexane). After stirring at −78° C. for 1 hour, the reaction mixture was quenched by the addition of 0.13 mL (2.13 mMol) iodomethane. The reaction mixture was allowed to warm to room temperature and was diluted with ethyl acetate. This mixture was then washed sequentially with water, saturated aqueous sodium bicarbonate, and saturated aqueous sodium chloride. The remaining organics were concentrated under reduced pressure. The residue was subjected to silica gel chromatography, eluting with hexane containing 20% ethyl acetate. Fractions containing product were combined and concentrated under reduced pressure to provide 0.16 gm (90%) of the desired compound.

2-methyl-2-(5-fluorobenzofur-7-yl)propionamide

A mixture of 0.156 gm (0.62 mMol) ethyl 2-methyl-2-(5-fluorobenzofur-7-yl)propionate, 0.095 gm (2.12 mMol) formamide, and 0.44 mL (0.44 mMol) sodium methoxide (1.0 M in methanol) in 3 mL dimethylformamide was heated at 100° C. for 45 minutes. The reaction mixture was diluted with ethyl acetate and the organics washed sequentially with water and saturated aqueous sodium chloride. The organics were then concentrated under reduced pressure and the residue subjected to silica gel chromatography, eluting with 2:1 hexane:ethyl acetate. Fractions containing product were combined and concentrated under reduced pressure to provide 0.060 gm (25%) of the desired compound.

Reduction

A mixture of 0.11 gm (0.49 mMol) 2-methyl-2-(5-fluorobenzofur-7-yl)propionamide and 0.02 gm (0.49 mMol) lithium aluminium hydride in 2 mL tetrahydrofuran was stirred at room temperature for 1 hour. The reaction mixture was then treated sequentially with 38 μL water, 38 μL 15% sodium hydroxide, and 0.11 μL water. The reaction mixture was stirred vigorously for 1 hour and was then filtered. The filtrate was concentrated under reduced pressure to provide 0.018 gm (18%) 2-methyl-2-(5-fluorobenzofur-7-yl)-1-aminopropane. The hydrochloride salt was prepared to provide the title compound.

EXAMPLE 77 syn-3-(5-trifluoromethylbenzofur-7-yl)-2-aminobutane oxalate 3-(5-trifluoromethylbenzofur-7-yl)-2-butanone A mixture of 0.27 gm (1.03 mMol) 5-trifluoromethyl-7-bromobenzofuran, 0.50 gm (1.55 mMol) methoxy(tri-n-butyl)tin, 0.18 gm (1.55 mMol) 2-acetoxy-2-butene, and 0.08 gm (0.10 mmol) bis[tri-o-tolylphosphine]palladium(II) chloride in 2.5 mL toluene was heated at 100° C. for 1 hour. The reaction mixture was cooled to room temperature and filtered through a pad of celite. The filtrate was concentrated under reduced pressure and the residue subjected to silica gel chromatography, eluting with 10% ethyl acetate in hexane. Fractions containing product were combined and concentrated under reduced pressure to provide 0.090 gm (34%) of the desired compound.

3-(5-trifluoromethylbenzofur-7-yl)-2-butanol

A solution of 0.09 gm (0.35 mMol) 3-(5-trifluoromethylbenzofur-7-yl)-2-butanone in ethanol was cooled to 0° C. To this solution was added 0.013 gm (0.35 mMol) sodium borohydride and the resulting mixture stirred for 30 minutes. The reaction mixture was then allowed to warm to room temperature and was concentrated under reduced pressure. The residue was taken up in ethyl acetate and washed sequentially with 0.1 N hydrochloric acid, water, and saturated aqueous sodium chloride. The remaining organic phase was concentrated under reduced pressure and the residue subjected to silica gel chromatography, eluting with 30% ethyl acetate in hexane. Fractions containing product were combined and concentrated under reduced pressure to provide 0.041 gm (45%) of the desired compound.

syn-3-(5-trifluoromethylbenzofur-7-yl)-2-azidobutane

To a solution of 0.103 gm (0.40 mMol) 3-(5-trifluoromethylbenzofur-7-yl)-2-butanol and 0.21 gm (0.80 mMol) triphenylphosphine in 2 mL toluene were added 0.092 gm (0.299 mMol) ZnN$_6$-(pyridine)$_2$ followed by the dropwise addition of 0.16 gm (0.80 mMol) diisopropyl azodicarboxylate. The reaction mixture was stirred for 2 hours at room temperature and was then filtered through a pad of celite. The filtrate was concentrated under reduced pressure and subjected to silica gel chromatography, eluting with hexane. Fractions containing product were combined and concentrated under reduced pressure to provide 0.040 gm (35%) of the desired compound.

Reduction

Beginning with 0.040 gm (0.14 mMol) syn-3-(5-trifluoromethylbenzofur-7-yl)-2-azidobutane, the reduction is performed essentially as described in EXAMPLE 76 to provide the title compound.

EXAMPLE 78

1-(5-fluorobenzofur-6-yl)-2-aminopropane fumarate

Beginning with 5-fluoro-6-bromobenzofuran, the title compound was prepared as a white crystalline solid essentially as described in EXAMPLE 1.

MS: m/e=194(M+1)

EXAMPLE 79

1-(5-fluorobenzofur-4-yl)-2-aminopropane fumarate

Beginning with 5-fluoro-4-bromobenzofuran, the title compound was prepared as a white crystalline solid essentially as described in EXAMPLE 1.

MS: m/e=194(M+1)

EXAMPLE 80

2-amino-3-methyl-4-(5-fluorobenzofur-7-yl)butane hydrochloride 3-methyl-4-(5-fluorobenzofur-7-yl)pentan-2-one A mixture of 1 gm (4.65 mMol) 5-fluoro-7-bromobenzofuran, 0.54 ml (5.23 mMol) 2-methyl-3-hydroxybut-1-ene, 9 mg (0.04 mMol) palladium(II) acetate, 0.021 gm (0.08 mMol) triphenylphosphine, and 0.44 gm (5.23 mMol) sodium bicarbonate in 5 mL hexamethylphosphoramide was heated at 130° C. for 3.5 hours. The reaction mixture was cooled to room temperature and was then diluted with 100 mL diethyl ether. The organic phase was washed sequentially with 2×20 mL water followed by 2×20 mL saturated aqueous sodium chloride. The remaining organics were dried over sodium sulfate and concentrated under reduced pressure. The residue was subjected to silica gel chromatography, eluting with 10:1 hexane:diethyl ether. Fractions containing the desired product were combined and concentrated under reduced pressure to provide the desired product in 81% yield as a colorless oil.

Reductive Amination

Beginning with 0.34 gm (1.55 mMol) 3-methyl-4-(5-fluorobenzofur-7-yl)pentan-2-one, the title compound was prepared essentially as described in EXAMPLE 1.

MS: m/e=222 (M$^+$)

EXAMPLE 81

2-amino-4-(5-fluorobenzofur-7-yl)pentane fumarate

Beginning with 2 gm (9.3 mMol) 5-fluoro-7-bromobenzofuran and 1.07 mL (10.47 mMol) 4-hydroxypent-2-ene, the title compound was prepared as a white crystalline solid essentially as described in EXAMPLE 80.

MS: m/e=222 (M+1)

EA: Calculated for $C_{13}H_{16}NOF$—$C_4H_4O_4$: C, 60.53; H, 5.98; N, 4.15. Found: C, 60.30; H, 6.14; N, 4.00.

EXAMPLE 82

2-amino-3-methyl-4-(5-fluorobenzofur-6-yl)butane fumarate

Beginning with 0.50 gm (2.3 mMol) 5-fluoro-6-bromobenzofuran and 0.27 mL (2.62 mMol) 2-methyl-3-hydroxybut-1-ene, the title compound was prepared as a white crystalline solid essentially as described in EXAMPLE 80.
MS: m/e=222 (M+)

EXAMPLE 83

2-amino-4-(5-fluorobenzofur-6-yl)pentane fumarate

Beginning with 0.33 gm (1.53 mmol) 5-fluoro-7-bromobenzofuran and 0.18 mL (1.73 mMol) 4-hydroxypent-2-ene, the title compound was prepared as a white crystalline solid essentially as described in EXAMPLE 80.

EXAMPLE 84

1-(4,6-difluorobenzofur-7-yl)-2-aminopropane hydrochloride

Beginning with 4,6-difluoro-7-bromobenzofuran, the title compound was prepared essentially as described in EXAMPLE 1.
MS: m/e=212.1 (M+1)

EXAMPLE 85

1-(4,6-difluorobenzofur-7-yl)-2-methyl-3-aminobutane hydrochloride

Beginning with 4,6-difluoro-7-bromobenzofuran, the title compound was prepared essentially as described in EXAMPLE 29.
MS: m/e=240.3 (M+1)

EXAMPLE 86 cis- and trans-2-(5-fluorobenzofur-7-yl)-3-aminobutane oxalate

Beginning with 5-fluoro-7-bromobenzofuran and 2-acetoxybut-2-ene, the title compound was prepared essentially as described in EXAMPLE 1.

EXAMPLE 87 trans-2-(5-fluorobenzofur-7-yl)-3-aminobutane hydrochloride

A mixture of cis- and trans-2-(5-fluorobenzofur-7-yl)-3-aminobutane was subjected to high pressure liquid chromatography to provide the title compound.
ISMS: m/e=208.1 (M+1)

EXAMPLE 88 cis-2-(5-fluorobenzofur-7-yl)-3-aminobutane hydrochloride

Beginning with 5-fluoro-7-bromobenzofuran and 2-acetoxy-2-butene, the title compound was prepared essentially as described in EXAMPLE 77.
ISMS: m/e=208 (M+1)

EXAMPLE 89

1-(3-ethyl-4,6-dimethyl-5-chlorobenzofur-7-yl)-2-aminopropane hydrochloride

Beginning with 3-ethyl-4,6-dimethyl-5-chloro-7-bromobenzofuran, the title compound was prepared essentially as described in EXAMPLE 1.
ISMS: m/e=266.1 (M+1)

EXAMPLE 90

1-(3-pentyl-5-fluorobenzofur-7-yl)-2-aminopropane oxalate

Beginning with 3-pentyl-5-fluoro-7-bromobenzofuran, the title compound was prepared essentially as described in EXAMPLE 1.
ISMS: m/e=264.1 (M+1)

EXAMPLE 91

1-(4-chloro-5-methoxycarbonylbenzofur-7-yl)-2-aminopropane oxalate

Beginning with 4-chloro-5-methoxycarbonyl-7-bromobenzofuran, the title compound was prepared essentially as described in EXAMPLE 1.
ISMS: m/e=268 (M+1)

EXAMPLE 92

1-(5-fluoro-6-methylbenzofur-7-yl)-2-aminopropane

Beginning with 5-fluoro-6-methyl-7-bromobenzofuran, the title compound was prepared essentially as described in EXAMPLE 1.
MS: m/e=208 (M+1)

EXAMPLE 93

1-(3-methylbenzofur-4-yl)-2-aminopropane

Beginning with 3-methyl-4-bromobenzofuran, the title compound was prepared essentially as described in EXAMPLE 1.
MS: m/e=190 (M+1)

The ability of the compounds of this invention to bind to the 5-HT$_{2c}$ receptor subtype was measure essentially as described by Wainscott (Wainscott, et al., *Journal of Pharmacology and Experimental Therapeutics*, 276, 720–727 (1996)).

Membrane Preparation

AV12 cells stably transfected with the human 5-HT$_{2c}$ receptors were grown in suspension and harvested by centrifugation, resuspended in 50 mM tris-HCl, pH 7.4, and frozen at −70° C. On the day of assay, an aliquot of cells was thawed, resuspended in 40 mL of 50 mM tris-HCl, pH 7.4, and centrifuged at 39,800×g for 10 minutes at 4° C. The resulting pellet was resuspended, incubated at 37° C. for 10 minutes to remove endogenous serotonin, then centrifuged twice more.

[$^{125}$I]-DOI Binding for Determination of 5-HT$_{2c}$ Receptor Affinity

Briefly, prepared cell membranes were added to dilutions of compounds in a final solution containing 50 mm tris-HCl, pH 7.4, 9.75 mM $MgCl_2$, 0.5 mM EDTA, 10 µM pargyline, 0.1% sodium ascorbate, and 0.1 nM [$^{125}$I]-DOI, with 10 µM mianserin for defining non-specific binding. All incubations (800 µL) were performed at 37° C. for 30 minutes before harvesting onto GF/C filters prewet with 0.5% polyethyleneimine, with four 1 mL washes of ice-cold 50 mM tris-HCl, pH 7.4, and counting in a gamma counter. Non-linear regression analysis was performed on the concentration response curves using a four parameter logistic equation described by DeLean (DeLean, et al., *Molecular Pharmacology*, 21, 5–16 (1982)). $IC_{50}$ values were converted to $K_i$ values using the Cheng-Prusoff equation (Cheng, et al., *Biochem. Pharmacol.*, 22, 3099–3108 (1973)).

Representative compounds of the present invention were found to have affinity for the 5-$HT_{2c}$ receptor as measured essentially by the procedure described supra.

The 5-$HT_{2c}$ receptor is functionally coupled to a G-protein. Agonist activation of G-protein-coupled receptors results in the release of GDP from the α-subunit of the G-protein and the subsequent binding of GTP. The binding of the stable analog [$^{35}$S]-GTPγS is an indicator of this receptor's activation.

[$^{35}$S]-GTPγS Binding

The [$^{35}$S]-GTPγS binding assay was modified from published conditions (Wainscott, et al., *European Journal of Pharmacology*, 352, 117–124 (1998)). All incubations were performed in triplicate in a total volume of 800 µL. Compounds were diluted in 200 µL of water and were added to 400 µL of 50 mM Tris-HCl, pH 7.4, containing 10 mM $MgCl_2$, 100 mM NaCl, 0.2 mM EGTA, 1 µM GDP, and 0.1 nM [$^{35}$S]-GTPγS. Membrane homogenates from AV12 cells stably transfected with the human 5-$HT_{2c}$ receptors (200 µL) were added and the tubes were incubated for 60 minutes at 30° C. Incubations were terminated by vacuum filtration through precooled GF/B filters which were prewet with 20 mM $Na_4P_2O_7$. The filters were rapidly washed with 4 mL ice-cold 50 mM tris-HCl, pH 7.4. [$^{35}$S]-GTPγS captured on the filters were determined by liquid scintillation spectrometry. Data analysis was performed as previously described, using 10 µM 5-HT to define maximally stimulated binding levels.

Representative compounds of the present invention were tested in the [$^{35}$S]-GTPγS assay and were found to be agonists of the 5-$HT_{2c}$ receptor.

The ability of agonists of the 5-$HT_{2c}$ receptor in general, and the compounds of the present invention in particular, to treat obesity is demonstrated by testing in a feeding assay.

Fasted Feeding Assay

Male rats were fasted for 18 hours prior to testing. Rats were first assigned to either a treatment or control group (N=8), then weighed, administered drug or vehicle orally, and returned to their home cage. Thirty minutes later, food was made available to the animals. The the food and the food hopper was weighed before, one hour, two hours, and four hours after food was made available to the test animals. Weight of food consumed plus spillage by the treatment animals was compared to food consumed plus spillage by control animals using a one-way ANOVA, with a Dunnett's post-hoc test.

Representative compounds of the present invention were tested in the feeding assay and were found to reduce food consumed by fasting rats.

While it is possible to administer a compound employed in the methods of this invention directly without any formulation, the compounds are usually administered in the form of pharmaceutical compositions comprising a pharmaceutically acceptable excipient and at least one active ingredient. These compositions can be administered by a variety of routes including oral, rectal, transdermal, subcutaneous, intravenous, intramuscular, and intranasal. Many of the compounds employed in the methods of this invention are effective as both injectable and oral compositions. Such compositions are prepared in a manner well known in the pharmaceutical art and comprise at least one active compound. See, e.g., REMINGTON'S PHARMACEUTICAL SCIENCES, (16th ed. 1980).

In making the compositions employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are generally effective over a wide dosage range. For examples, dosages per day normally fall within the range of about 0.01 to about 30 mg/kg. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

FORMULATION EXAMPLE 1

Hard gelatin capsules containing the following ingredients are prepared:

| Ingredient | Quantity (mg/capsule) |
|---|---|
| Compound of Example 10 | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/tablet) |
|---|---|
| Compound of Example 11 | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation is prepared containing the following components:

| Ingredient | Weight % |
|---|---|
| Compound of Example 12 | 5 |
| Lactose | 95 |

The active mixture is mixed with the lactose and the mixture is added to a dry powder inhaling appliance.

FORMULATION EXAMPLE 4

Tablets, each containing 30 mg of active ingredient, are prepared as follows:

| Ingredient | Quantity (mg/tablet) |
|---|---|
| Compound of Example 76 | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

FORMULATION EXAMPLE 5

Capsules, each containing 40 mg of medicament are made as follows:

| Ingredient | Quantity (mg/capsule) |
|---|---|
| Compound of Example 50 | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount |
|---|---|
| Compound of Example 59 | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 ml dose are made as follows:

| Ingredient | Amount |
| --- | --- |
| Compound of Example 74 | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

Capsules, each containing 15 mg of medicament, are made as follows:

| Ingredient | Quantity (mg/capsule) |
| --- | --- |
| Compound of Example 17 | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

FORMULATION EXAMPLE 9

An intravenous formulation may be prepared as follows:

| Ingredient | Quantity |
| --- | --- |
| Compound of Example 39 | 250.0 mg |
| Isotonic saline | 1000 ml |

FORMULATION EXAMPLE 10

A topical formulation may be prepared as follows:

| Ingredient | Quantity |
| --- | --- |
| Compound of Example 42 | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

FORMULATION EXAMPLE 11

Sublingual or buccal tablets, each containing 10 mg of active ingredient, may be prepared as follows:

| Ingredient | Quantity Per Tablet |
| --- | --- |
| Compound of Example 57 | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The type of formulation employed for the administration of the compounds employed in the methods of the present invention may be dictated by the particular compounds employed, the type of pharmacokinetic profile desired from the route of administration and the compound(s), and the state of the patient.

We claim:

1. The compounds of Formula I:

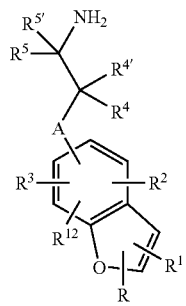

where:
- A is —CHR$^{13}$— or a bond and is attached at the 7-position of the benzofuran ring;
- R is hydrogen, halo, cyano, —C(O)NR$^6$R$^7$, $C_1$–$C_6$ alkyl, $C_1$–$C_4$ alkoxycarbonyl, carboxy, or phenyl optionally substituted with one or two substituents selected from the group consisting of halo, $C_1$–$C_4$ alkyl, and $C_1$–$C_4$ alkoxy;
- R$^1$ is hydrogen;
- R$^2$ and R$^3$ are independently hydrogen, halo, amino, nitro, $C_1$–$C_4$ alkoxy, cyano, carboxamido, —C(O)NR$^8$R$^9$, —NR$^{10}$R$^{11}$, —NHC(O)NHR$^{14}$, $C_1$–$C_4$ alkoxycarbonyl, carboxyl, trifluoromethyl, or $C_1$–$C_6$ alkyl optionally substituted with a substituent selected from the group consisting of $C_1$–$C_4$ alkoxy, hydroxy, phenoxy, and phenyl;
- R$^4$ and R$^{4'}$ are independently hydrogen, $C_1$–$C_4$ alkyl, or benzyl; or R$^4$ and R$^{4'}$ together with the carbon atom to which they are attached form a cyclopropyl moiety;
- R$^5$ is hydrogen, $C_1$–$C_4$ alkyl, or benzyl;
- R$^{5'}$ is hydrogen, or R$^5$ and R$^{5'}$ together with the carbon atom to which they are attached form a cyclopropyl moiety;
- R$^6$ and R$^7$ are independently hydrogen or $C_1$–$C_4$ alkyl;
- R$^8$ is hydrogen or $C_1$–$C_4$ alkyl;
- R$^9$ is $C_1$–$C_8$ alkyl where the alkyl chain is optionally substituted with a substituent selected from the group consisting of carboxy, phenyl, or pyridyl, said phenyl or pyridyl substituent optionally substituted with one or two substituents selected from the group consisting of halo, $C_1$–$C_4$ alkyl, or $C_1$–$C_4$ alkoxy;
- R$^{10}$ is hydrogen or $C_1$–$C_4$ alkyl;
- R$^{11}$ is $C_1$–$C_4$ alkyl or $C_1$–$C_4$ acyl;
- R$^{12}$ is hydrogen, halo, or $C_1$–$C_4$ alkyl;
- R$^{13}$ is hydrogen, $C_1$–$C_4$ alkyl, or benzyl;
- R$^{14}$ is hydrogen, $C_1$–$C_4$ alkyl, or phenyl optionally substituted with a substituent selected from the group consisting of halo, $C_1$–$C_4$ alkyl, and $C_1$–$C_4$ alkoxy;

or pharmaceutically acceptable acid addition salts thereof.

2. A pharmaceutical formulation which comprises, in association with a pharmaceutically acceptable carrier, diluent or excipient, a therapeutically effective amount of a compound of Formula I:

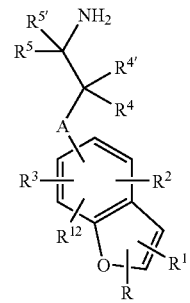

where:
- A is —CHR$^{13}$— or a bond;
- R is hydrogen, halo, cyano, —C(O)NR$^6$R$^7$, $C_1$–$C_6$ alkyl, $C_1$–$C_4$ alkoxycarbonyl, carboxy, or phenyl optionally substituted with one or two substituents selected from the group consisting of halo, $C_1$–$C_4$ alkyl, and $C_1$–$C_4$ alkoxy;
- R$^1$ is hydrogen, halo, cyano, carboxamido, formyl, trimethylsilyl, trifluoromethyl, pentafluoroethyl, or $C_1$–$C_6$ alkyl;
- R$^2$ and R$^3$ at independently hydrogen, halo, amino, nitro, $C_1C_4$ alkoxy, cyano, carboxamido, —C(O)NR$^8$R$^9$, —NR$^{10}$R$^{11}$, —NHC(O)NHR$^{14}$, $C_1$–$C_4$ alkoxycarbonyl, carboxyl, trifluoromethyl, or $C_1$–$C_6$ alkyl optionally substituted with a substituent selected from the group consisting of $C_1$–$C_4$ alkoxy, hydroxy, phenoxy, and phenyl;
- R$^4$ and R$^{4'}$ are independently hydrogen, $C_1$–$C_4$ alkyl, or benzyl; or R$^4$ and R$^{4'}$ together with the carbon atom to which they are attached form a cyclopropyl moiety;
- R$^5$ is hydrogen, $C_1$–$C_4$ alkyl, or benzyl;
- R$^{5'}$ is hydrogen, or R$^5$ and R$^{5'}$ together with the carbon atom to which they are attached form a cyclopropyl moiety;
- R$^6$ and R$^7$ are independently hydrogen or $C_1$–$C_4$ alkyl;
- R$^8$ is hydrogen or $C_1$–$C_4$ alkyl;
- R$^9$ is $C_1$–$C_8$ alkyl where the alkyl chain is optionally substituted with a substituent selected from the group consisting of carboxy, phenyl, or pyridyl, said phenyl or pyridyl substituent optionally substituted with one or two substituents selected from the group consisting of halo, $C_1$–$C_4$ allyl, or $C_1$–$C_4$ alkoxy;
- R$^{10}$ is hydrogen or $C_1$–$C_4$ alkyl;
- R$^{11}$ is $C_1$–$C_4$ alkyl or $C_1$–$C_4$ acyl;
- R$^{12}$ is hydrogen, halo, or $C_1$–$C_4$ alkyl;
- R$^{13}$ is hydrogen, $C_1$–$C_4$ alkyl, or benzyl;
- R$^{14}$ is hydrogen, $C_1$–$C_4$ alkyl, or phenyl optionally substituted with a substituent selected from the group consisting of halo, $C_1$–$C_4$ alkyl, and $C_1$–$C_4$ alkoxy;

or pharmaceutically acceptable acid addition salts thereof.

3. A method for the treatment of obesity in mammals, comprising administering to a mammal in need of such treatment an effective amount of a compound of Formula I:

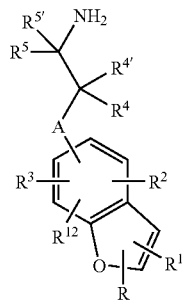

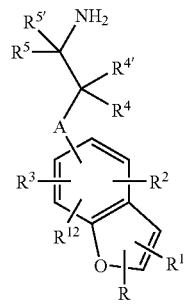

where:
- A is —CHR$^{13}$— or a bond;
- R is hydrogen, halo, cyano, —C(O)NR$^6$R$^7$, C$_1$–C$_6$ alkyl, C$_1$–C$_4$ alkoxycarbonyl, carboxy, or phenyl optionally substituted with one or two substituents selected from the group consisting of halo, C$_1$–C$_4$ alkyl, and C$_1$–C$_4$ alkoxy;
- R$^1$ is hydrogen, halo, cyano, carboxamido, formyl, trimethylsilyl, trifluoromethyl, pentafluoroethyl, or C$_1$–C$_6$ alkyl;
- R$^2$ and R$^3$ are independently hydrogen, halo, amino, nitro, C$_1$–C$_4$ alkoxy, cyano, carboxamido, —C(O)NR$^8$R$^9$, —NR$^{10}$R$^{11}$, —NHC(O)NHR$^{14}$, C$_1$–C$_4$ alkoxycarbonyl, carboxyl, trifluoromethyl, or C$_1$–C$_6$ alkyl optionally substituted with a substituent selected from the group consisting of C$_1$–C$_4$ alkoxy, hydroxy, phenoxy, and phenyl;
- R$^4$ and R$^{4'}$ are independently hydrogen, C$_1$–C$_4$ alkyl, or benzyl; or R$^4$ and R$^{4'}$ together with the carbon atom to which they are attached form a cyclopropyl moiety;
- R$^5$ is hydrogen, C$_1$–C$_4$ alkyl, or benzyl;
- R$^{5'}$ is hydrogen, or R$^5$ and R$^{5'}$ together with the carbon atom to which they are attached form a cyclopropyl moiety;
- R$^6$ and R$^7$ are independently hydrogen or C$_1$–C$_4$ alkyl;
- R$^8$ is hydrogen or C$_1$–C$_4$ alkyl;
- R$^9$ is C$_1$–C$_8$ alkyl where the alkyl chain is optionally substituted with a substituent selected from the group consisting of carboxy, phenyl, or pyridyl, said phenyl or pyridyl substituent optionally substituted with one or two substituents selected from the group consisting of halo, C$_1$–C$_4$ alkyl, or C$_1$–C$_4$ alkoxy;
- R$^{10}$ is hydrogen or C$_1$–C$_4$ alkyl;
- R$^{11}$ is C$_1$–C$_4$ alkyl or C$_1$–C$_4$ acyl;
- R$^{12}$ is hydrogen, halo, or C$_1$–C$_4$ alkyl;
- R$^{13}$ is hydrogen, C$_1$–C$_4$ alkyl, or benzyl;
- R$^{14}$ is hydrogen, C$_1$–C$_4$ alkyl, or phenyl optionally substituted with a substituent selected from the group consisting of halo, C$_1$–C$_4$ alkyl, and C$_1$–C$_4$ alkoxy, or pharmaceutically acceptable acid addition salts thereof.

4. A method for the treatment of depression in mammals, comprising administering to a mammal in need of such treatment an effective amount of a compound of Formula I:

where:
- A is —CHR$^{13}$— or a bond;
- R is hydrogen, halo, cyano, —C(O)NR$^6$R$^7$, C$_1$–C$_6$ alkyl, C$_1$–C$_4$ alkoxycarbonyl, carboxy, or phenyl optionally substituted with one or two substituents selected from the group consisting of halo, C$_1$–C$_4$ alkyl, and C$_1$–C$_4$ alkoxy;
- R$^1$ is hydrogen, halo, cyano, carboxamido, formyl trimethylsilyl, trifluoromethyl, pentafluoroethyl, or C$_1$–C$_6$ alkyl;
- R$^2$ and R$^3$ are independently hydrogen, halo, amino, nitro, C$_1$–C$_4$ alkoxy, cyano, carboxamido, —C(O)NR$^8$R$^9$, —NR$^{10}$R$^{11}$, —NHC(O)NHR$^{14}$, C$_1$–C$_4$ alkoxycarbonyl, carboxyl, trifluoromethyl, or C$_1$–C$_6$ allyl optionally substituted with a substituent selected from the group consisting of C$_1$–C$_4$ alkoxy, hydroxy, phenoxy, and phenyl;
- R$^4$ and R$^{4'}$ are independently hydrogen, C$_1$–C$_4$ alkyl, or benzyl; or R$^4$ and R$^{4'}$ together with the carbon atom to which they are attached form a cyclopropyl moiety;
- R$^5$ is hydrogen, C$_1$–C$_4$ alkyl, or benzyl;
- R$^{5'}$ is hydrogen, or R$^5$ and R$^{5'}$ together with the carbon atom to which they are attached form a cyclopropyl moiety;
- R$^6$ and R$^7$ are independently hydrogen or C$_1$–C$_4$ alkyl;
- R$^8$ is hydrogen or C$_1$–C$_4$ alkyl;
- R$^9$ is C$_1$–C$_8$ alkyl where the alkyl chain is optionally substituted with a substituent selected from the group consisting of carboxy, phenyl, or pyridyl, said phenyl or pyridyl substituent optionally substituted with one or two substituents selected from the group consisting of halo, C$_1$–C$_4$ alkyl, or C$_1$–C$_4$ alkoxy;
- R$^{10}$ is hydrogen or C$_1$–C$_4$ alkyl;
- R$^{11}$ is C$_1$–C$_4$ alkyl or C$_1$–C$_4$ acyl;
- R$^{12}$ is hydrogen, halo, or C$_1$–C$_4$ alkyl;
- R$^{13}$ is hydrogen, C$_1$–C$_4$ alkyl, or benzyl;
- R$^{14}$ is hydrogen, C$_1$–C$_4$ alkyl, or phenyl optionally substituted with a substituent selected from the group consisting of halo, C$_1$–C$_4$ alkyl, and C$_1$–C$_4$ alkoxy;

or pharmaceutically acceptable acid addition salts thereof.

5. A method of claim 3 where the mammal is human.

6. A method of claim 4 where the mammal is human.

* * * * *